US010466245B2

(12) United States Patent
Sutton et al.

(10) Patent No.: US 10,466,245 B2
(45) Date of Patent: Nov. 5, 2019

(54) COVALENTLY LINKED THERMOSTABLE KINASE FOR DECONTAMINATION PROCESS VALIDATION

(71) Applicant: The Secretary of State for Health, London (GB)

(72) Inventors: J. Mark Sutton, Salisbury (GB); J. Richard Hesp, Salisbury (GB); Michael Ungurs, Salisbury (GB)

(73) Assignee: The Secretary of State for Health, London (GB)

( * ) Notice: Subject to any disclaimer, the term of this patent is extended or adjusted under 35 U.S.C. 154(b) by 517 days.

(21) Appl. No.: 15/205,841

(22) Filed: Jul. 8, 2016

(65) Prior Publication Data

US 2017/0052190 A1 Feb. 23, 2017

Related U.S. Application Data

(62) Division of application No. 12/918,628, filed as application No. PCT/GB2009/050158 on Feb. 18, 2009, now Pat. No. 9,416,396.

(30) Foreign Application Priority Data

Feb. 20, 2008 (GB) .................................. 0803068.6

(51) Int. Cl.
*G01N 33/58* (2006.01)
*C12Q 1/48* (2006.01)

(52) U.S. Cl.
CPC ........... *G01N 33/581* (2013.01); *C12Q 1/485* (2013.01); *G01N 2333/9121* (2013.01)

(58) Field of Classification Search
CPC ......... B01L 2300/042; B01L 2300/047; B01L 2300/069; B01L 2400/0409; B01L 3/5021; B01L 2300/0681; G01N 15/042; G01N 1/4077; G01N 2001/4083; G01N 2001/4088; G01N 33/6872; G01N 15/04; G01N 2333/9121; G01N 33/581; C07K 14/705; C12N 15/86; C12N 2770/24223; C12N 2770/24243; C12N 2770/24252; C12N 7/00; C12N 15/90; C12N 9/0071; C12Q 1/04; C12Q 1/06; C12Q 1/485; C12Q 1/68; C12Q 1/6897; C12Y 114/14003
See application file for complete search history.

(56) References Cited

U.S. PATENT DOCUMENTS

| | | | | |
|---|---|---|---|---|
| 6,348,641 | B1 | 2/2002 | Stiles et al. | |
| 8,389,208 | B2 * | 3/2013 | Sutton | C12Q 1/485 435/5 |
| 9,416,396 | B2 * | 8/2016 | Sutton | C12Q 1/485 |
| 2002/0015697 | A1 | 2/2002 | Beckman et al. | |
| 2005/0031648 | A1 | 2/2005 | Brin et al. | |
| 2008/0161543 | A1 | 7/2008 | Steward et al. | |
| 2009/0317794 | A1 | 12/2009 | Sutton et al. | |

FOREIGN PATENT DOCUMENTS

| | | | |
|---|---|---|---|
| EP | 0781848 | A2 | 7/1997 |
| JP | 2003-509476 | A | 3/2003 |
| JP | 2007-505094 | A | 3/2007 |
| JP | 2008-511627 | A | 4/2008 |
| JP | 2008-521428 | A | 6/2008 |
| WO | WO 2000/046357 | A1 | 8/2000 |
| WO | WO 2000/065344 | A2 | 11/2000 |
| WO | WO 2001/021213 | A2 | 3/2001 |
| WO | WO 2002/009743 | A1 | 2/2002 |
| WO | WO 2002/094743 | A2 | 11/2002 |
| WO | WO 2004/076634 | A2 | 9/2004 |
| WO | WO 2005/023309 | A2 | 3/2005 |
| WO | WO 2005/093085 | A1 | 10/2005 |
| WO | WO 2005/123764 | A1 | 12/2005 |
| WO | WO 2006/026780 | A1 | 3/2006 |
| WO | WO 2006/059113 | A2 | 6/2006 |
| WO | WO 2006/094539 | A1 | 9/2006 |
| WO | WO 2007/106799 | A2 | 9/2007 |
| WO | WO 2008/105901 | A2 | 9/2008 |
| WO | WO 2009/104013 | A1 | 8/2009 |
| WO | WO 2009/150469 | A2 | 12/2009 |
| WO | WO 2009/150470 | A2 | 12/2009 |

OTHER PUBLICATIONS

Hess, et al., "The 3-Phosphoglycerate Kinase of the Hyperthermophilic Archaeum Coli: Loss of Heat Resistance Due to Internal translation Initiation and its Restoration by Site-Directed Mutagenesis," Gene, 172(1), Jun. 12, 1996, pp. 121-124.
O'Brien, et al., "P. 148 Development of a Novel Immunoassay for Ultra-Sensitive Oral Diagnosis of Hepatitis C Virus," Journal of Clinical Virology, 36, Jan. 1, 2006, p. S106.
PCT International Application No. PCT/GB2009/050158: International Search Report dated May 8, 2009, 5 pages.

(Continued)

*Primary Examiner* — Aaron J Kosar
(74) *Attorney, Agent, or Firm* — BakerHostetler

(57) ABSTRACT

A biological process indicator is provided for validating a treatment process in which the amount or activity of a contaminant in a sample is reduced. The indicator comprises a thermostable kinase covalently linked to a biological component, with the proviso that the biological component is not an antibody. Methods of preparing the indicator, and methods of using the indicator, are also provided.

21 Claims, 11 Drawing Sheets

Specification includes a Sequence Listing.

(56) References Cited

OTHER PUBLICATIONS

PCT International Application No. PCT/GB2009/050158: International Preliminary Report on Patentability dated Dec. 17, 2009, 13 pages.
IUBMB "Adenylate Kinase [EC 2.7.4.3]" IUBMB Enzyme Nomenclature, <http://www.chem.qmul.ac.uk/iubmb/enzyme/EC2/7/4/3.html>, archived May 21, 2002, retrieved online Jul. 11, 2014, 1 page.
NC-IUBMB, "EC 2.7.4.3: Adenylate Kinase" IUBMB Enzyme Nomenclature, <http://www.chem.qmul.ac.uk/iubmb/ enzyme/EC2/7/4/3.html> May 21, 2002 (accessed online Sep. 29, 2013), 1 page.

* cited by examiner

FIG. 2A
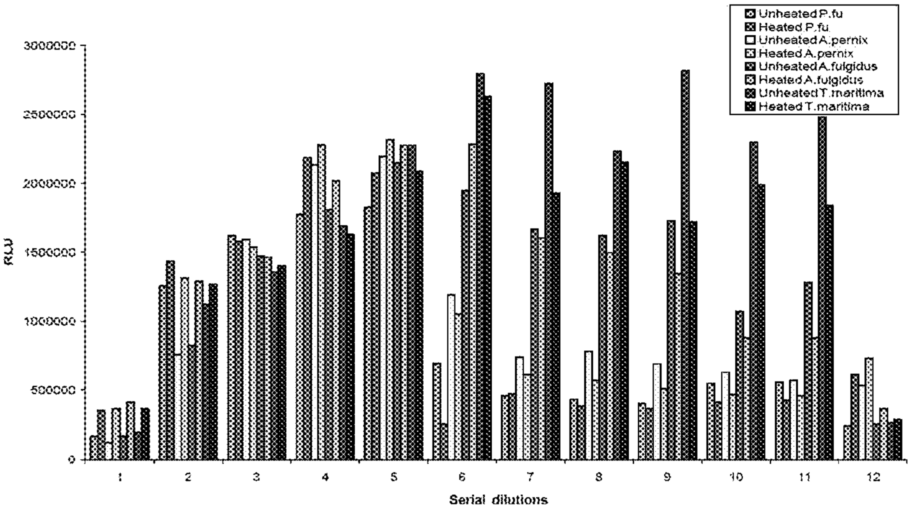
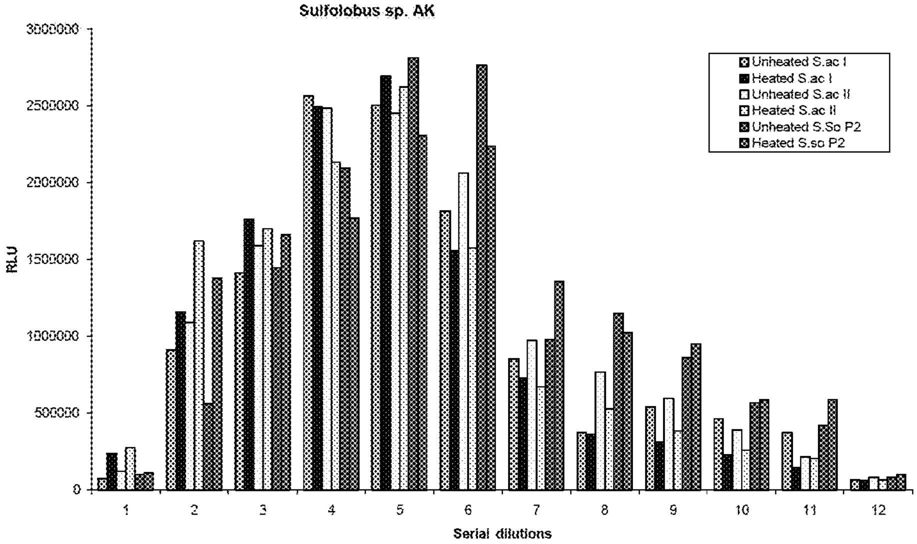
FIG. 2B

COVALENTLY LINKED THERMOSTABLE KINASE FOR DECONTAMINATION PROCESS VALIDATION

CROSS REFERENCE TO RELATED APPLICATIONS

This Application is a divisional of U.S. patent application Ser. No. 12/918,628, filed on Apr. 6, 2011, now U.S. Pat. No. 9,416,396, issued on Aug. 16, 2016, which is the National Stage of International Application No. PCT/GB2009/050158, filed Feb. 18, 2009, which claims benefit of Patent Application No. 0803068.6, filed Feb. 20, 2008, in Great Britain, the disclosure of which are incorporated herein by reference in their entirety.

BACKGROUND

The invention relates to the field of biological indicators, and in particular to biological indicators for the validation of treatment processes designed to reduce the amount or activity of a contaminant in a sample. The invention further relates to methods of preparing these indicators, and to the uses thereof.

A wide variety of biological indicators are known for validating cleaning and decontamination processes. These range from relatively basic indicators, such as those that use a simple "visual score" to assess whether a process has been effective, to more sophisticated indicators that rely on thermostable kinases as reporter enzymes (WO2005/093085). These kinase-based indicators have been an important development in the biological indicator field, providing a rapid and sensitive means of process validation.

WO2005/093085 describes in detail the production and use of the kinase-based indicators referred to above. In summary, a typical indicator is prepared by adsorbing a thermostable kinase onto a solid support such as an indicator strip or dipstick. The indicator is then included with a sample (containing a contaminant) to be treated, and the indicator plus sample are subjected to a treatment process. The reduction in activity of the indicator kinase by the treatment is then correlated with the reduction in amount or activity of the contaminant. When a level of activity is determined that is known to correlate with an acceptable reduction in the contaminant, the treatment is then regarded as validated.

It has now been found that the performance of these kinase-based indicators can be significantly improved by covalently cross-linking the thermostable kinase to a biological component, wherein the biological component is a mimetic/surrogate of the contaminant. This allows the indicator to more accurately reflect the reaction of the contaminant to the treatment process, which in turn leads to improved indicator accuracy/sensitivity, and thus fewer "false" process validations.

Advantageously, the biological component may be part of a biological matrix or mixture, such as a commercially available test soil (Browne soil, Edinburgh soil etc.), blood, neurological tissue, food, culled animal material, serum, egg, mucus, or a test soil made up to meet the specific requirements of the user. In this way, the reduction in the amount/activity of the kinase is a function of the diverse properties of the matrix, which further improves the accuracy/sensitivity of the indicator.

An indicator of this type is also able to monitor the removal/inactivation of a specific component of the matrix or mixture. Advantageously, an indicator can be designed so that the thermostable kinase is linked to the most "difficult" component of the matrix to remove/inactivate (e.g., in a matrix of blood, fibrin is much more difficult to remove than haemoglobin). This provides for an extremely stringent validation of the treatment process.

The indicators described above also have the advantage of providing rapid, single step, process validations. This is in contrast to certain known validation indicators, which require multiple steps for validation and therefore require a much greater investment of time and effort. By way of example, WO00/65344, describes the use of a yeast prion as a biological indicator for a prion decontamination process. At the end of the process, the operator must, in a further step, assay the destruction of the yeast prion in order to validate the process. In contrast, the indicators described above are designed to have an indicator kinase linked directly to a biological component that mimics the relevant contaminant (e.g., prion) so that the destruction of this component is intimately linked to the loss of kinase activity. As such, these indicators are able to provide for a rapid single-step indication of process efficacy.

The invention therefore addresses the problem of providing an alternative/improved kinase-based biological indicator.

Biological Process Indicator

In a first aspect of the invention, there is provided a biological process indicator for validating a treatment process in which the amount or activity of a contaminant in a sample is reduced, wherein the indicator comprises a thermostable kinase covalently linked to a biological component, with the proviso that the biological component is not an antibody.

In one embodiment, the biological component is a mimetic or surrogate of the contaminant, and therefore reacts to the treatment process in substantially the same way as the contaminant. In another embodiment, the biological component may be the same as, but physically distinct from, the contaminant in the sample that is to be subjected to the treatment process, e.g., if the contaminant is a protein, then the biological component is also a protein; if the contaminant is a blood protein, the biological component is also blood protein; if the contaminant is a DNA molecule, then the biological component is also a DNA molecule; if the contaminant is an RNA molecule then the biological component is also an RNA molecule, etc. for each of the contaminants and biological components disclosed in this specification. In a further embodiment, the biological component may be different from the contaminant.

Examples of biological components that can be used in the indicators of the invention include proteins, nucleic acids, carbohydrates and lipids.

In one embodiment, the biological component comprises a protein selected from the group consisting of a blood protein, a bacterial protein, a viral protein, a fungal protein, and a self-aggregating or amyloid forming protein.

In a further embodiment, the blood protein is selected from the group consisting of blood clotting proteins (e.g., fibrinogen, fibrin peptides, fibrin, transglutaminase substrates, thrombin), serum proteins (e.g., albumin and globulin), platelet proteins, blood cell glycoproteins, and haemoglobin.

In another embodiment, the bacterial protein is selected from the group consisting of a bacterial fimbrial protein (e.g CgsA from *E. coli* and AgfA from *Salmonella*), a bacterial toxin protein (e.g., toxins from *Bacillus anthracis, Corynebacterium diphtheriae, Clostridium botulium*), a bacterial cell surface protein (e.g., peptidoglycan, lipoproteins), and a bacterial spore protein (e.g., from Gram positive bacteria and having a similar sequence or overall structure to the proteins forming ribbon appendages in *Clostridum taeniosporum*, chaplin proteins, rodlin proteins).

In yet another embodiment, the viral protein is selected from the group consisting of a viral envelope protein, a viral capsid protein, and a viral core protein. Suitably, the viral proteins are from a bacteriophage virus (e.g., the MS2 and PP7 proteins), norwalk virus (e.g., capsid protein), rotavirus (e.g., VP2, VP6 and VP7 proteins), coronavirus (e.g., SARS S, E and M proteins), bluetongue virus (e.g., VP2 protein), human papillomavirus (e.g., viral major structural protein, L1), hepatitis B (e.g., small envelope protein HBsAg), Hepatitis C virus (e.g., core, E1 and E2 proteins), influenza virus (e.g., neuraminidase and haemagglutinin and matrix proteins), poliovirus (e.g., capsid VP0, 1 and 3 proteins), HIV (e.g., Pr55gag, envelope proteins) and dengue B virus (e.g., envelope (e) and pre-membrane/membrane (prM/M).

In another embodiment, the fungal protein is selected from the group consisting of hydrophobin proteins (e.g., SC3 from *Schizophyllum commune*, RodA/B from *Aspergillus* fumigates, and equivalent proteins from yeast), fungal spore proteins, hyphal proteins, mycotoxins, and fungal prions (e.g., Sup35, Het S, URE 2, Rnq1, New 1).

In yet another embodiment, the self-aggregating protein is selected from the group consisting of prions (e.g., $PrP^{Sc}$ and $PrP^{c}$, Sup35, Het S, Ure 2, Rnq1, New 1), prion mimetic proteins, amyloid fibrils, cell surface adhesins from floc forming and filamentous bacteria in activated sludge, beta amyloid protein, tau protein, polyadenine binding protein, herpes simplex virus glycoprotein B, lung surfactant protein C, CsgA protein from *E. coli*, AgfA protein from *Salmonella* species, bacterial fimbrial proteins, apolipoproteins (e.g., apolipoprotein A1), hydrophobins from fungal species (e.g., SC3 from *Schizophyllum commune*, RodA/B from *Aspergillus* fumigates), chaplins (e.g., Chps A-H from *Streptomyces* spp), rodlins (e.g., Rd1A and Rd1B from *streptomyces* spp), gram positive spore coat proteins (e.g., P29a, P29b, GP85 and a SpoVM analogue), and barnacle cement-like proteins (e.g., the 19 kDa protein from *Balanus albicostatus*, and the 20 kDa protein from *Megabalanus rosa*, and the novel calcite-dependent cement-like protein from *Balanus albicostatus*).

In another embodiment, the nucleic acid is selected from a DNA molecule and an RNA molecule. In a further embodiment, the nucleic acid is selected from single-stranded DNA (ssDNA), single-stranded RNA (ssRNA), double-stranded DNA (dsDNA) or double-stranded RNA (dsRNA). In one embodiment, the nucleic acid is derived from neurological tissue.

In another embodiment, the carbohydrate is selected from the group consisting of exopolysaccharide, lipopolysaccharide (EPS/LPS, sometimes known as endotoxin) (e.g., from *Legionella* species, *E. coli, Staphylococcus* species, *Streptococcus* species, *Pseudomonas* species, *Acinetobactor* species, *Campylobactor* species, and *Bacillus* species), peptidoglycan, cell wall components of plants, fungi and yeast (e.g., chitin, lignin, glucan), mucin preparations, glycolipids (especially brain derived glycolipids), glycoproteins (e.g., cell surface glycoproteins, Eap1p), spore extracts (e.g., from *Bacillus* spp, *Clostridal* spp and other spore-formers), polysaccharides from yeast capsules, and invertebrate secretions (e.g., from molluscan gels).

In another embodiment, the lipid is selected from the group consisting of glycolipids (e.g., brain-derived glycolipids), gangliosides (e.g., neuronal cell gangliosides such as $GT_{1b}$, $GT_{1a}$ and gangliosides of more general cell origin such as $GM_1$), and plant oils and lipids.

In a further embodiment, the biological component is part of a biological matrix. In one embodiment, the indicator is covalently linked to the biological matrix. The biological matrix may be a mimetic of the sample that is to be treated. In one embodiment, the biological matrix comprises one or more components selected from the group consisting of proteins, lipids, nucleic acids, and carbohydrates, or fragments or derivatives thereof. In another embodiment, the biological matrix may comprise a mixture of proteins. In a further embodiment, the biological matrix may comprise one or more components selected from the group consisting of blood, serum, albumin, mucus, egg, neurological tissue, food, culled animal material, and a commercially available test soil. In yet another embodiment of the invention, the biological matrix comprises one or more components selected from the group consisting of fibrinogen, thrombin, factor VIII, $CaCl_2$, and, optionally, albumin and/or haemoglobin.

In one embodiment of the invention, the thermostable kinase is covalently linked to the biological component. In another embodiment, the thermostable kinase is genetically or chemically cross-linked to the biological component. In a further embodiment, the biological component is linked to the thermostable kinase in the form of a fusion protein.

The indicators of the invention may be used to validate treatment processes designed to remove/inactivate a contaminant selected from the group consisting of a protein, a lipid, a carbohydrate and a nucleic acid.

The biological process indicator of the invention may further comprise an agent to stabilise the kinase, such as metal ions, sugars, sugar alcohols or gel-forming agents.

The indicator of the invention (including any biological matrix) may also be “fixed” by treatment with 70% ethanol or isopropanol. To achieve this, the indicator/matrix is incubated in 70% isopropanol for 30 minutes at room temperature. This mimics one of the commonly encountered processes which may increase the resistance of contaminating materials on surgical instruments, and therefore provides the indicator with an effective way of monitoring the removal of such materials.

The biological process indicator of the invention may be immobilised in or immobilised on a solid support. In one embodiment, the biological process indicator is immobilised in the solid support, or is immobilised on the solid support by chemical cross-linking or adsorption. The indicator may be attached to the solid support via the thermostable kinase, or via the biological component.

In one embodiment, the solid support is an indicator strip, a dip-stick or a bead, and, optionally, further comprises means to attach the solid support to a surface (such as a projection, recess or aperture for attachment of the solid support to a surface by means of a screw, nut and bolt, or clamp). In a further embodiment, the solid support is a matrix and the indicator is dispersed within the matrix.

In one embodiment of the invention, the enzyme used to form the biological process indicator is not a lichenase, a xylanase, a xylosidase, a formiltransferase, a Taq polymerase, an alpha-amylase, or a beta-glucosidase.

In yet another embodiment of the invention, there is provided a test soil comprising an indicator as described above.

Preparation of the Biological Indicator

The biological indicator of the invention may be prepared by covalently linking a thermostable kinase to an appropriate biological component. Any suitable method of covalent attachment known in the art may be used. In one embodiment, the thermostable kinase is genetically or chemically cross-linked to the biological component, and in one embodiment, the indicator is prepared as a fusion protein.

Chemical cross-linking may be achieved using a range of homo- and hetero-bifunctional reagents commonly used for cross-linking of proteins for the generation of enzyme conjugates or other related purposes. For example, in an indicator comprising fibrin as the biological component, the fibrin and the thermostable kinase may be derivatised with the addition of SPDP (Perbio) to primary amine groups. The thermostable kinase can then be reduced to generate a reactive thiol group and this is then mixed with the fibrin to produce covalent fibrin-thermostable kinase linkages.

The kinases can also be chemically cross-linked to carbohydrates, lipids or other glycoconjugates using heterobifunctional agents following treatment of the target carbohydrate with meta-periodate. The cross-linking may be achieved using a variety of chemistries as outlined in Example 23.

Alternatively, the indicator may be prepared as a fusion protein. This is achieved by fusing a synthetic gene encoding an appropriate thermostable kinase (e.g., the gene encoding AK from *Sulfolobus acidocaldarius* or *Thermatoga neopolitana*) to a gene encoding an appropriate biological component. Detailed protocols for the preparation of fusion protein indicators are given in the Examples (see e.g., Examples 10 & 13).

Kinase Enzymes for Use in the Biological Indicator

The kinase enzymes used in the indicators of the invention are capable of generating a signal that is detectable over an extremely wide range. Generally, the kinase is detected using a substrate comprising ADP which is converted to ATP, itself used to generate light, eg. using luciferin/luciferase, detected using a luminometer. The wide range makes the indicator particularly suitable for validation as the kinase remains detectable even after many logs reduction in amount/activity. For sterility, most national institutes regard a 6 log reduction in the amount or activity of a contaminant as required before sterility can be validated. The kinases used in the indicators of the invention offer the potential of validating reduction in the amount or activity of contaminants well beyond 6 logs, to 8 logs and more.

Any suitable kinase enzyme may be used as the reporter kinase in the present invention. In one embodiment, the reporter kinase is an adenylate kinase, acetate kinase or pyruvate kinase, or a combination thereof.

The reporter kinases used in the invention may have a variety of recognized tertiary structures, e.g., the kinase may be a trimeric or monomeric kinase. These tertiary structures may be associated with an improved stability of the kinase to conditions such as e.g., temperature, pH, chemical denaturants, or proteases.

In one embodiment, the reporter kinase is a microbial kinase derived from an organism selected from the group consisting of *Pyrococcus furiousus, P. abyssi, P. horikoshii, P. woesii, Sulfolobus solfataricus, Sacidocaldarius, S. shibatae, Rhodothermus marinus, Thermococcus litoralis, Thermatoga maritima, Thermatoga neapolitana* and *Methanococcus* spp. In another embodiment, the kinase is a *Sulfolobus* sp. kinase or a *Thermotoga* sp. kinase. In yet another embodiment, the kinase is a *A. acidocaldarius* kinase, *A. fulgidus* kinase, *A. pernix* kinase, *A. pyrophilus* kinase, *B. caldotenax* BT1 kinase, *Bacillus* species PS3 kinase, *B. stearothermophilus* 11057 kinase, *B. stearothermophilus* 12001 kinase, *B. thermocatenulatus* kinase, *C. stercocorarium* kinase, *Methanococcus* spp. Kinase, *M. ruber* kinase, *P. abyssi* kinase, *P. furiosus* kinase, *P. horikoshii* kinase, *P. woesii* kinase, *R. marinus* kinase, *S. acidocaldarius* kinase, *S. shibatae* kinase, *S. solfataricus* kinase, *T. ethanolicus* kinase, *T. thermosulfurogenes* kinase, *T. celere* kinase, *T. litoralis* kinase, *T. aquaticus* YT1 kinase, *T. caldophilus* GK24 kinase, *T. thermophilus* HB8 kinase, *T. maritima* kinase or a *T. neapolitana* kinase. In yet a further embodiment, the kinase is a *T. litoralis* kinase, *T. maritima* kinase, or a *T. neapolitana* kinase.

In one embodiment, the reporter kinase is thermostable. As well as being resistant to high temperatures, thermostable kinases are also found to be resistant to other biochemical and physical processes that routinely damage or destroy proteins or render them inactive, such as exposure to certain chemicals e.g., chaotropes, free-radical damage, detergents, extremes of pH, exposure to proteases, protein cross-linking, encapsulation within non-permeable or semi-permeable membranes or polymers, or irreversible immobilisation onto surfaces. (See for example: Daniel R M, Cowan D A, Morgan H W, Curran M P, "A correlation between protein thermostability and resistance to proteolysis", Biochem J. 1982 207:641-4; Rees D C, Robertson A D, "Some thermodynamic implications for the thermostability of proteins", Protein Sci. 2001 10:1187-94; Burdette D S, Tchernajencko V V, Zeikus J G. "Effect of thermal and chemical denaturants on *Thermoanaerobacter* ethanolicus secondary-alcohol dehydrogenase stability and activity", Enzyme Microb Technol. 2000 27:11-18; Scandurra R, Consalvi V, Chiaraluce R, Politi L, Engel P C., "Protein thermostability in extremophiles", Biochimie. 1998 November; 80(11):933-41; and Liao H H., "Thermostable mutants of kanamycin nucleotidyltransferase are also more stable to proteinase K, urea, detergents, and water-miscible organic solvents", Enzyme Microb Technol. 1993 April; 15(4):286-92, all of which are hereby incorporated by reference in their entirety).

Examples of kinases suitable for use in the invention are set out in SEQ ID NO.s 1-32 below. In one embodiment, the kinases used in the invention have at least 70%, 80%, 85%, 90%, 95%, 99% or 100% identity to SEQ ID Nos: 1-32.

Other examples of suitable reporter kinases may be found in WO00/46357 and WO2005/093085, which are hereby incorporated by reference in their entirety.

In one embodiment of the invention, kinase activity is detected using an ATP bioluminescent detection system. A standard luciferin-luciferase assay method can detect as little as $10^{-15}$ moles of ATP. By coupling an enzymatic amplification to the bioluminescent detection methods it is possible to detect as few as $10^{-20}$ moles of kinase.

Stabilisation of the Biological Indicator

A number of additives and changes to formulation that increase the stability of an enzyme, e.g., a kinase, to heat inactivation will be known to those familiar with the art.

The addition of stabilising agents such as sorbitol up to a concentration of 4M, or other polyols such as ethylene glycol, glycerol, or mannitol at a concentration of up to 2M may improve the thermostability of the enzyme. Other additives such as xylan, trehalose, gelatin may also provide additional stabilisation effects either individually or in combination. Addition of a range of divalent metal ions, most notably $Ca^{2+}$, $Mg^{2+}$ or $Mn^{2+}$ may also improve stability of the enzyme.

Chemical modification of the enzymes can also be used to improve their thermal stability. Reductive alkylation of surface exposed amino groups by glyoxylic acid (e.g Melik-Nubarov (1987) Biotech lefts 9:725-730), addition of carbohydrates to the protein surface (e.g., Klibanov (1979) Anal. Biochem. 93:1-25) and amidation (e.g., Klibanov (1983) Adv. Appl. Microbiol. 29:1-28) may all increase the stability of the enzyme. Further methods including the use of chemical cross-linking agents and the use of various polymeric supports for enzyme immobilisation are also relevant methods for increasing the thermostability of enzymes (reviewed in Gupta (1991) Biotech. Appl. Biochem. 14:1-11).

Similar modifications are also relevant to the stabilisation of the indicator against other sterilisation processes such as hydrogen peroxide or ozone. In particular, processes where the access of the gaseous phase sterilant to the enzyme is restricted, for example by encapsulation in a suitable polymer or formulation with an additive to reduce penetration of the gas, will provide useful methods for increasing the stability of the enzyme if required.

Many of the treatments that are effective at increasing the thermal stability of enzymes are also relevant to the stabilisation against protease treatments, e.g., for the development of an indicator for the effective inactivation of TSE agents by protease treatment. In general, a protein that shows high levels of thermostability is likely to also show a high degree of stability for degradative processes such as denaturation or protease treatment (See for example: Daniel R M, Cowan D A, Morgan H W, Curran M P, "A correlation between protein thermostability and resistance to proteolysis", Biochem J. 1982 207:641-4; Rees D C, Robertson A D, "Some thermodynamic implications for the thermostability of proteins", Protein Sci. 2001 10:1187-94; Burdette D S, Tchemajencko V V, Zeikus J G. "Effect of thermal and chemical denaturants on *Thermoanaerobacter ethanolicus* secondary-alcohol dehydrogenase stability and activity", Enzyme Microb Technol. 2000 27:11-18; Scandurra R, Consalvi V, Chiaraluce R, Politi L, Engel P C., "Protein thermostability in extremophiles", Biochimie. 1998 November; 80(11):933-41; and Liao H H., "Thermostable mutants of kanamycin nucleotidyltransferase are also more stable to proteinase K, urea, detergents, and water-miscible organic solvents", Enzyme Microb Technol. 1993 April; 15(4):286-92). Thermostable kinases therefore generally show a higher degree of stability to the actions of the protease treatments designed to inactivate TSE agents than might equivalent mesophilic kinases. Depending on the type of process used, a kinase can also be selected to favour other characteristics of the process. Thus for a protease treatment at alkaline pH the protocol tends towards the use of a thermostable kinase from a moderately alkalophilic organism such as *P. furiosus*, whereas a protease treatment at acidic pH might use a kinase from an acidophile such as *S. acidocaldarius* or *S. solfotaricus*.

If required to improve the stability of the kinase indicator to protease treatment a number of other options exist. A number of these are the same as those described above for the stabilisation of the enzyme against heat treatment. For example, formulations containing sorbitol, mannitol or other complex polymers reduce the levels of inactivation of the enzyme on the indicator surface. In addition, treatments that specifically reduce the rate at which a protease substrate is degraded are particularly relevant to this application. For example, the formulation of the kinase in a solution containing up to around 10 mg/ml (a 10-fold excess compared to the preferred concentration of the indicator) of a suitable carrier protein such as casein or albumin, that acts as alternative substrate for the protease, will specifically reduce the rate of digestion of the kinase indicator. Similarly, the addition of free amino acids such as glycine, tyrosine, tryptophan or dipeptides to the formulation would provide a means of substrate level inhibition of the enzyme and reduce local inactivation of the kinase indicator.

Thermostable kinases produced by recombinant expression in bacteria can also be used in the present invention. The genetic modification of enzymes has been shown to provide significant increases in thermal stability and by analogy such mutations are also likely to significantly enhance the stability of the indicator enzymes in other processes such as protease treatment or gaseous phase "sterilisation". The comparison of the thermostability of the kinase enzymes taken with the defined 3-D structure of the trimeric (archaeal) AKs (Vonrhein et al. (1998) J. Mol. Biol. 282:167-179 and Criswell et al. (2003) J. Mol. Biol. 330: 1087-1099) has identified amino acids that influence the stability of the enzyme.

Genetically engineered variants of kinases showing improved thermostability are also used in the invention, and can be generated in a number of ways. Essentially these involve the specific site-directed mutagenesis of amino acids believed to form part of the central core packing region of the trimeric molecule and random "directed evolution" methods where the whole molecule is subjected to subsequent rounds of mutagenesis and selection/screening of molecules with improved properties. Specific modified enzymes are set out in SEQ ID NOs: 17-19 (several variants are embraced by each reference). These modifications outlined are based on a hybrid approach using a consensus based approach to define regions likely to influence the thermostability of the enzymes based on observed differences between structurally related molecules. This is followed by either defined changes to incorporate the amino acids that correlate with the best thermostability or a random replacement to incorporate every available amino acid at the positions defined as being essential for thermostability.

The stability/resistance of the indicators that bind to biological components that are part of a matrix may be improved by increasing the concentration of the biological component in the matrix, or by increasing the degree of cross-linking. By way of example, one of the indicators of the invention employs a fibrin-reactive peptide-kinase indicator to effect cross-linking into a biological matrix containing fibrin, e.g., a fibrin film. By altering the fibrin film, e.g., by increasing the concentration of fibrin, or by increasing its degree of cross linking, it is possible to significantly increase the resistance of the indicator to specific processes.

The resistance of indicators containing biological components such as Sup35 can be increased by promoting the fibrilisation of the indicators. This provides a molecule with greater physical stability, and may be relevant to monitoring the inactivation of agents such as prion proteins, which are believed to be multimeric in nature.

In one embodiment, the indicator is formulated in a carrier selected from the group consisting of sucrose (e.g., at up to 1% w/v), mucin (e.g., at up to 0.5% w/v), and albumin (e.g., at up to 1 mg/ml).

Solid Supports

The biological indicator of the invention may be attached to a variety of solid supports. The supports may be with or without chemical modifications and may comprise one or more indicators in a variety of formulations, depending e.g., on the requirements of the process to be validated. In one form the support is a plastic, wood, ceramic, glass, textile, steel or other metallic or polymer surface onto which the indicator is dried/cross-linked as a means of immobilisation. The support can be a polycarbonate, polystyrene or polypropylene strip or dipstick, optionally with a flattened surface, onto which the indicator is applied. An additional type of support with a porous surface for attachment of indicator is also particularly useful as an indicator for gaseous processes. Plastic, wooden, metallic or ceramic beads may also provide a valuable format for the solid support, again with specific relevance to monitoring gaseous processes. Such supports have advantages for certain applications, as they provide a significantly increased surface area for the attachment of the indicator. In a further embodiment, the solid support is a matrix and the indicator is dispersed within the matrix. In yet another embodiment, the matrix is a complex biological matrix.

Immobilisation of the Biological Indicator onto the Solid Support

The indicators of the invention may be bound onto the solid support using any of a wide variety of methods known in the art.

In one embodiment of the invention, the indicator is bound onto the solid support via standard protein adsorption methods as outlined below.

Binding of the indicator onto the solid support may be achieved by methods routinely used to link protein to surfaces, e.g., incubation of protein in 0.1M sodium bicarbonate buffer at about pH 9.6 at room temperature for about 1 hour. Alternatively, the protein is covalently coupled to the surface using any of a wide range of coupling chemistries known to those familiar with the art. For example, an adenylate kinase fusion protein (e.g., to Sup35) derivatised with SPDP (Pierce chemicals; using manufacturer's instructions), reduced with DTT to provide free sulfhydryl groups for cross-linking, is covalently attached to a polystyrene support with a maleimide surface. Plastic surfaces with such sulfhydryl-binding surfaces are well described in the literature. An added benefit of this method of coupling is that, if required, the enzyme can be cleaved from the support, e.g., by reduction with DTT or MESNA, to allow the assay to be carried out separately to any indicator support. The indicators described in this application have the property that their activity is retained upon derivatisation and cross-linking to such supports.

Alternatively, an amine reactive surface on a polystyrene or polycarbonate support is used, with a bifunctional cross-linking agent such as monomeric glutaraldehyde, to provide direct non-cleavable cross-linking of the kinase indicator via free amine groups on the protein. UV treatment can also be used to directly link the indicator to a suitable support. Steel surfaces can be treated in a similar way to plastic surfaces to mediate covalent attachment of the indicator.

A wide variety of protein cross-linking reagents are available from companies such as Pierce chemical company (Perbio). Reagents reactive to sulfhydryl, amino, hydroxyl and carboxyl groups are designed for coupling proteins but they can equally be used for cross-linking proteins to either naturally reactive or coated solid supports such as plastics, other polymers, glass and metals. Reactive chemistries are also available for cross-linking the enzymes to carbohydrates. For example, the reagents BMPH ((N-[ß-maleimidopropionic acid]hydrazide.TFA), KMUH ((N-[k-maleimidoundecanoic acid]hydrazide), and MPBH (4-(4-N-maleimidophenyl)butyric acid hydrazide hydrochloride) can be used to cross link the indicator containing either a free sulfhydryl in the form of a cysteine residue or a chemically derivatised protein reduced to generate a sulfhydryl reactive group, to carbohydrates. This may be particularly important for a solid support which is either a complex carbohydrate (e.g., paper, cellulose-based membranes, gels or resins) or can be coated or treated with a carbohydrate solution to generate a suitably reactive surface.

For each type of support, the indicator may be formulated in a solution that enhances binding and/or stabilises the bound protein. Such formulations include solutions containing up to 10% (w/v) sucrose, sorbitol, mannitol, cellulose, or polyethylene glycol (PEG). In addition, the indicator can be formulated as part of a gel that is applied to the surface or lumen of a suitable support. Examples include alginate, agar or polyacrylamide matrices.

The indicator may also comprise an agent to stabilise the indicator, and suitable stabilising agents are selected from metal ions, sugars, sugar alcohols and gel-forming agents.

To facilitate use of the indicator, the indicator may further comprise means to attach the solid support to a surface, such as a projection, recess or aperture for attachment of the support to a surface by means of a screw, nut and bolt or clamp.

Kits Comprising the Biological Indicator

In a second aspect of the invention, there is provided a kit for use in validating a treatment process in which the amount or activity of a contaminant in a sample is reduced, comprising:

(i) a biological process indicator according to the first aspect of the invention, and (ii) a substrate for the thermostable kinase.

To carry out measurement of the kinase amount/activity, the kit can include means for detecting ATP, e.g., luciferin/luciferase and optionally a luminometer. In one embodiment, the substrate for the thermostable kinase is ADP.

From previous testing with known contaminants, data correlating the reduction in the amount or activity of the contaminant with kinase activity can be prepared, and the kit therefore can also include one or more look-up tables correlating kinase activity with the reduction in amount or activity of a list of specified contaminants. In one embodiment, the kit is for monitoring TSE inactivation. In a further embodiment, the kit is used for monitoring norovirus inactivation.

Use of the Biological Indicator

In a third aspect, the invention provides for the use of a thermostable kinase covalently linked to a biological component as a biological process indicator for validating a treatment process for reducing the amount or activity of a contaminant in a sample.

In one embodiment, the biological process indicator is formulated according to the first aspect of the invention.

In a particular use of the invention, an indicator according to the first aspect of the invention is the reporter in a method of indicating the possible presence of a contaminant (e.g., an infectious agent) following a cleaning or inactivation procedure. First, a sample containing the indicator is exposed to a cleaning/inactivation procedure (e.g., one or more of a selected temperature, pH or protease concentration). The next step is to remove any contaminating enzymatic activity by heat treatment, e.g., at from 60° C. to 80° C. for at least 10 minutes (i.e. under conditions that do not significantly affect the thermostable kinase). The indicator is then reacted at a temperature of between 30° C. and 70° C. with a substrate (e.g., ADP) to allow the generation of ATP. The formation of ATP can be measured by bioluminescent detection using luciferin/luciferase and a suitable luminometer at 20° C.-30° C. for 10 minutes to 1 hour. The light output reading from the luminometer gives a reading of the residual kinase activity, i.e. the activity of the kinase following exposure to the cleaning/inactivation treatment. Based on data that have been previously derived from separate experiments, the method is completed by correlating the residual kinase activity with the possible presence of a contaminant within the treated sample.

In one embodiment, contaminating enzymatic activity or ATP in a sample may be removed by an initial treatment step (e.g., a selected temperature, pH or protease concentration), prior to addition of the indicator.

The use of the indicator of the invention to monitor/validate a variety of processes is now described.

In one embodiment, the indicator is used to validate the performance of a biological washing preparation in a wash cycle. Whilst validation of a wash cycle would potentially be of use in a domestic setting, its most advantageous use would be within a healthcare, pharmaceutical or food preparation setting, e.g., for validating decontamination of bedclothes, gowns or other items associated with patients suffering or exposed to infectious agents (e.g., an outbreak of methicillin resistant *Staphylococcus aureus* (MRSA) or Norwalk/Norwalk-like virus). In this context, the indicator of the invention has the advantage that it is relevant to biological material such as blood or other bodily fluids.

For the validation of a wash cycle, the indicator may be cross-linked onto a flexible wand, strip of cloth or other material suitable for inclusion within the cycle. The indicator is put into the washer with the remainder of the load. In one embodiment, the indicator may be fixed within a suitable holder on the inside of the washer to facilitate its recovery.

The wash cycle is then performed and the indicator removed and assessed prior to any further handling or processing of the load, using a "reader" which has been calibrated to indicate an acceptable level of residual kinase activity within the indicator—the acceptable level having been derived from previous calibration and assessment of suitable wash performance within the process. Such assessment might include the overall levels of soiling and the viable count of micro-organisms as assessed using suitable model organisms known to those familiar with the art. Based on the calibrated read-out, the load is passed for further processing or the wash cycle is repeated.

In a second embodiment, the indicator is used to validate processes for the inactivation of viruses. The detection of live viral isolates in the environment is problematic, particularly when associated with an emergency situation where speed and accuracy may be critical. The present invention provides the possibility of developing indicator systems that allow the monitoring of decontamination procedures essentially in real time. This would be particularly valuable for surface decontamination in healthcare and related facilities following either an outbreak (e.g., of Norwalk-like viruses) or a deliberate release of a viral agent (such as small pox).

An indicator for validating a viral inactivation process can take a variety of different forms, e.g., a wand or dipstick for monitoring an area sprayed or immersed with virucide, or a suspended indicator for monitoring a gaseous phase decontamination process. Alternatively, the indicator can be sprayed onto a surface prior to decontamination and the levels of residual kinase activity subsequently assessed by swabbing of the surface.

In a further embodiment of the invention, the indicator is used for validating protease degradation of bacterial protein toxins, plant toxins such as ricin, and other toxic proteins, peptides, or peptide analogues.

Proteases show significant potential for the degradation of a wide range of protein toxins that are potential biowarfare/bioterror threat agents including botulinum toxin, anthrax toxins and ricin. They also have the potential to inactivate a wide range of other potentially toxic or harmful protein or peptide agents to enable decontamination of surfaces/facilities or the safe disposal of materials. In this context, the indicator of the invention, together with the surface/material to be decontaminated, is subjected to the protease decontamination procedure. At the end of the procedure, the residual kinase activity of the indicator is assessed according to the method of the invention. The level of residual kinase activity is then correlated with inactivation indices for the particular protein toxin, or group of toxins. Assuming the level activity is equal to or below the defined index value then the material can be safely disposed of or the surface/facility returned to use.

In one embodiment, a suitable safety margin is built into the calibration of the inactivation indices to allow for any variability of the process performance. The additional stability of the enzymes used in this invention allow for this to be done with more certainty and greater dynamic range than a wide range of other enzymatic indicators, including those from "thermostable" organisms such as *Bacillus stearothermophilus*, as shown by the data showing the relative thermal stability of AKs from thermophilic organisms (FIGS. 1A, 1B, and 1C).

The indicator may also be used to validate protease decontamination procedures for cleaning down pharmaceutical production apparatus. A wide variety of pharmaceutical products use materials from either humans, or animals that might be contaminated with a wide variety of agents including prion (TSE) agents and viruses (e.g., West Nile virus, hepatitis, HIV). The risks may be exacerbated when the source of the material is of animal origin (e.g foetal calf serum, horse immunoglobulins) and where an intermediate processing stage may carry the risk of increasing the concentration of unidentified pathogens in a particular sample. The possibility of using a protease to clean down manufacturing facilities and apparatus (e.g., chromatography columns, vessels, pipework) between manufacturing batches has the potential to reduce or eliminate such risks, even when the contaminant has not been formally identified. This is particularly true for prion agents in, for example, blood fractionation apparatus where there is a significant risk of accumulation and of carrying an infection risk into the final product.

For validating this type of procedure, the indicator of the invention is ideally formulated as a dipstick to be immersed in the protease treatment solution, or as a cartridge to be attached in line with the apparatus to be cleaned. By assessing the levels of residual kinase activity in the indicator device following the treatment, and correlating this with the acceptable levels of cleaning, a rapid and reliable monitor of performance can be developed.

In another embodiment of the invention, the indicator is used for validating gas phase inactivation of contaminants, such as TSE.

The potential of ozone or other gas phase sterilants to inactivate such contaminants is suggested by a wide range of publications and articles, however, as yet, no method has explicitly been shown to be effective. To support the development and introduction of this gas phase technology into healthcare, a means of validating the performance of the technology will be required. As agents such as TSE have already been shown to be far more resistant to this form of inactivation than conventional viral or bacterial agents, the methods currently available for validating gas phase inactivation are unlikely to be suitable. The present invention addresses this problem.

For this type of validation, the indicator is attached onto a solid support by any suitable method, e.g., general adsorption and chemical cross-linking via amide, peptide, carbonyl, or cysteine bonds. For example, for ozone sterilisation, a rigid polyvinyl chloride (PVC), glass, steel, polyamide or polypropylene support may be used, with the indicator coupled to the support by any one of the methods previously described. The indicator is then included in the batch of material/instruments to be sterilised, exposed to the ozone, and assessed against a suitably calibrated inactivation index designed for assessing corresponding inactivation of the agent in question. Successful inactivation allows onward processing or use of the material/instruments.

The indicator may optionally be attached to the internal face of a tube or equivalent internal space, such that the penetration of the gas is restricted. This provides for a monitor that is suitable for assessing the penetration of the gas into equivalent spaces in instruments with lumens, or through packed loads of material. Alternatively, the indicator may be attached to porous materials such as polystyrene beads, or may be immobilised within a gel or resin.

In a further embodiment of the invention, the indicator is used for validating liquid chemical sterilisation systems (e.g., ENDOCLENS-NSX™) as used for processing of endoscopes and related equipment.

A wide range of endoscopes are routinely used in medicine and are an important part of medical diagnosis and treatment. These instruments are extremely sensitive and have posed a very significant problem for routine cleaning and disinfection. Traditionally, and remaining in current practice, endoscopes are cleaned by hand before being decontaminated using a low temperature method. A range of chemical disinfectants and automated re-processing apparatus has been developed to address the specific issues of decontaminating sensitive pieces of equipment such as endoscopes, where traditional autoclaving is not possible. These methods have helped to reduce the levels of contamination on difficult to clean instruments, which have been associated with the iatrogenic transmission of a wide range of viral and bacterial pathogens. The current method of validating such processes is to monitor the flow rate and temperature of the washing solution. The indicator of the invention provides for a further means of validation that provides a read-out of actual cleaning effectiveness within the endoscope lumen.

For this type of validation, the indicator is attached to the internal surface of a tube designed to be of a similar overall internal diameter to the endoscope tube. This indicator apparatus is connected in series to the endoscope on the automatic reprocessing apparatus. The endoscope is then processed in the normal way. At the end of the process, preferably before the endoscope is removed from the apparatus, the indicator is detached and assessed for the level of kinase activity remaining. The level of activity may be correlated with previously defined thresholds for the acceptable performance of the process and, based on this assessment, the endoscope may be transferred for additional cleaning or decontamination or prepared for use. If the level of performance is not adequate then the instrument may be re-processed (using the same or more stringent conditions) with a new indicator attached as previously. The indicator apparatus is also suitable for validating the manual cleaning of endoscope and/or any other instrument with a lumen.

In a further embodiment of the invention, the indicator is used to monitor routine cleaning performance in washer-disinfectors, such as those used in hospitals.

In another embodiment of the invention, the indicator is used for monitoring glutaraldehyde or ortho-phthaldehyde (OPA) treatments. Glutaraldehyde and formaldehyde have been widely used as sterilants over many years. The chemical disinfectants work by multiply crosslinking proteins in a non-specific fashion to destroy their function. Ortho-phthaldehyde (OPA) has emerged recently as a new disinfectant in this family and is being widely used as it avoids some of the toxicity problems associated with glutaraldehyde. The indicator of the invention is suitable for the monitoring of all of this class of chemical disinfectants as the kinases are sensitive to non-specific cross-linking of this kind. The indicator may be covalently attached to a suitable surface and exposed to the chemical sterilant along with the other items to be sterilised. The effectiveness of the process is assessed by measuring the residual enzyme activity of the indicator. This activity is compared to defined threshold values that indicate the correct performance of the process.

The use of different types of kinase may provide additional sensitivity or susceptibility to the process as may be required for different applications. The thermostable adenylate kinases described in this specification can be broadly classified into two groups based on their molecular architecture. Thus, the enzymes from *Sulfolobus* species are examples of enzymes that have a trimeric structure with a central hydrophobic core that is the principle determinant in maintaining their activity at high temperatures. The second group of enzymes are monomeric, exemplified by the adenylate kinases from *Thermatoga* species, but have a slightly longer polypeptide chain with an additional "lid" domain that affects the active site. These different types of thermostable enzymes will show differential sensitivity to this type of chemical sterilant due to the variable flexibility of their peptide chains during enzyme action. For any particular sterilant and/or concentration an empirical screen will identify enzymes with suitable susceptibilities for monitoring and validating these types of chemicals.

In a further embodiment of the invention, the indicator is used as an ultra-rapid read-out monitor for ethylene oxide, hydrogen peroxide or other gas phase processes.

A wide range of gas phase sterilants are currently being used by a variety of manufacturers for routine disinfection of bacterial and viral agents. The current methods exploit the oxidative properties of the gases to destroy peptide linkages. As such, the kinases of the present invention, with their robust physicochemical properties, are ideal for providing a very rapid read-out of inactivation. The indicator in this example is similar to those described previously, e.g., in relation to the ozone inactivation of agents such as TSE.

A particularly challenging issue for sterilisation and decontamination processes is the ability to validate sterility of large bulk liquids, as might be required in the manufacture of various medicines or other pharmaceutical products. Whilst current methods monitor the temperature, time, and/or pressure parameters of a particular process (depending on its precise nature), there are few, if any, available methods for validating actual sterilisation within the bulk liquid. This is difficult even within volumes of around 1 liter, but is almost impossible at larger volumes.

The present invention provides a number of possible solutions to address this problem. In its simplest form, the indicator may be added to the liquid to be sterilised at a concentration suitable for measuring defined levels of kinase inactivation at the end of the process and equating this to levels of sterilisation. Whilst this might not be desirable in certain types of processes, the inert nature of the kinase and the ubiquitous presence of equivalent enzyme activities in all organisms, may make it acceptable. The acceptability may be improved by the fact that many thermostable enzymes are highly condensed and thus have very low immunogenicity following inoculation into animals.

Where such direct additions are not acceptable, the indicator may be added to the bulk liquid in a dialysis sack, porous container or immobilised to a suitable support such that no part of the indicator is released into the bulk liquid, but the sterilising conditions work on the indicator in the same way as for the whole sample. A wide variety of possible ways of containing or immobilising proteins, to allow general diffusion of the liquid sample but to restrict the movement of the indicator sample, will be known to those familiar with the art. Possible examples include, but are not limited to dialysis membranes, Visking tubing, porous membranes, protein-binding resins, rigid gels or solid supports as described for the other indicators discussed. The indicator may be attached to the surface by any one of the methods discussed previously, or simply encased within a suitable membrane without attachment, such that the indicator may be simply removed from the bulk liquid at completion of the process.

Method of Validating a Treatment Process

In a fourth aspect, the invention provides a method of validating a treatment process for reducing the amount or activity of a contaminant in a sample, comprising the steps of:

(a) obtaining a sample that contains or is suspected to contain a contaminant;
(b) subjecting the sample to a treatment process in the presence of a defined amount of a thermostable kinase covalently linked to a biological component;
(c) measuring residual kinase activity and optionally calculating the reduction in kinase activity; and
(d) comparing said residual kinase activity to a predetermined kinase activity, or comparing said reduction in kinase activity to a pre-determined reduction in kinase activity, wherein the pre-determined kinase activity or the pre-determined reduction in kinase activity corresponds to a confirmed reduction in the amount or activity of the contaminant under the same conditions.

It is possible that the sample in step (a) may not contain any contaminant at all. The point of the validation is that, after carrying out the treatment, it is confirmed that any agent that might have been present has been removed/inactivated to an acceptable degree. In general, however, the sample is known to contain, or suspected to contain, the contaminant.

In one embodiment, the thermostable kinase used in step (b) of the method is formulated as an indicator according to the first aspect of the invention.

In another embodiment, the residual kinase activity in step (c) is measured by adding a substrate comprising ADP to the residual kinase and measuring the formation of ATP. ATP formation can be measured by bioluminescent detection using luciferin/luciferase and a suitable luminometer.

Typically, an operator measures kinase activity before and after treating the sample. It is also possible that contaminating, usually mesophilic, kinase can get into the sample prior to assaying for kinase activity. Thus, in one embodiment of the invention, the assay includes the step of inactivating mesophilic kinase, such as by treating the sample at 70° C. for at least 30 minutes, or at 80° C. for at least 10 minutes, prior to measuring residual kinase activity.

In one embodiment, the kinase, prior to the treatment, has an activity of at least 10,000,000 Relative Light Units (RLU) per mg kinase, or at least 8,000,000 RLU per mg kinase, or at least 5,000,000 RLU per mg kinase, or at least 3,000,000 per mg kinase, or at least 1,000,000 RLU per mg kinase, or at least 500,000 RLU per mg kinase, when measured in the presence of luciferin/luciferase by a luminometer.

In another embodiment of the invention, the predetermined kinase activity is less than 10,000 RLU per mg kinase, or less than 1000 RLU per mg kinase, or less than 500 RLU per mg kinase, or less than 250 RLU per mg kinase, or less than 100 RLU per mg kinase, or less than 10 RLU per mg kinase, or less than 1 RLU per mg kinase, or is 0 RLU per mg kinase.

In a further embodiment of the invention, the predetermined reduction in kinase activity is equal to or greater than a 1 log reduction, or a 2 log reduction, or a 3 log reduction, or a 4 log reduction, or a 5 log reduction, or a 6-log reduction, or a 7 log reduction, or an 8 log reduction or a 9 log reduction in kinase activity.

In another embodiment, the predetermined reduction in kinase activity corresponds to a 3 log reduction, or a 6 log reduction, or a 7 log reduction, or an 8 log reduction, or a 9 log reduction, in the amount or concentration of the kinase. In further embodiments, the predetermined reduction in kinase activity corresponds to a reduction in RLU of at least 800,000, or at least 900,000, or at least 950,000, or at least 990,000, or at least 999,000, or at least 999,900, or at least 999,990, or at least 999,999 RLU.

In yet another embodiment of the invention, the confirmed reduction in the amount or activity of the contaminant within the sample is at least 3 logs, at least 6 logs, ably at least 7 logs, more ably at least 8 logs, most ably at least 9 logs.

In another embodiment of the invention, the treatment is continued until the residual kinase activity or the reduction in the kinase activity corresponds to a confirmed reduction in the amount or activity of the contaminant of at least 3 logs, at least 6 logs, or at least 7 logs, or at least 8 logs, or at least 9 logs.

In one embodiment of the invention, the method further comprises the step of recording the data obtained in step (c) on a suitable data carrier.

Method of Correlating

In a fifth aspect, the invention provides a method of correlating the reduction in the amount or activity of a contaminant in a sample with the kinase activity of a biological process indicator as described in connection with the first aspect of the invention. This method comprises:

(i) preparing a sample containing a defined amount of the contaminant and a sample containing a defined amount of the indicator according to the first aspect of the invention, or preparing a single sample containing both a defined amount of the contaminant and a defined amount of the indicator according to the first aspect of the invention;
(ii) subjecting the sample or samples to a treatment;
(iii) measuring the residual activity of the indicator kinase and optionally calculating the reduction in kinase activity;
(iv) measuring residual amount or activity of the contaminant and optionally calculating the reduction in the amount or activity of the contaminant;
(v) repeating steps (i) to (v), wherein at least one of the treatment parameters is changed.

In one embodiment, the treatment parameter comprises one or more of time, temperature, pH, pressure, protease concentration, and concentration of sterilant or detergent.

In a particular embodiment, the treatment comprises heating the sample(s) at 50-140° C., or 80-100° C., or 134-138° C.; the treatment parameter is time; and steps (i) to (iv) are repeated by subjecting the sample(s) to said treatment for periods of 1, 5, 10, 20, 40 and 60 minutes.

In a further embodiment, the treatment comprises exposing the sample(s) to a pH of 9-14, or pH 12 or above, or about pH 12; the treatment parameter is time; and steps (i)

to (iv) are repeated by subjecting the sample(s) to said treatment for periods of 1, 5, 10, 20, 40 and 60 minutes.

In another embodiment, the treatment comprises exposing the sample(s) to a protease at a concentration of 0.5-2 mg/ml, or about 1 mg/ml, or about 2 mg/ml; the treatment parameter is time; and steps (i) to (iv) are repeated by subjecting the sample(s) to said treatment for periods of 1, 5, 10, 20, 40 and 60 minutes.

The above method enables preparation of calibration data for future use of the indicator for validation of a treatment on samples containing, or suspected of containing contaminant. The calibration of a number of treatment processes is described in WO2005/093085.

Definitions Section

The term "contaminant" encompasses both infectious and non-infectious agents derived from a biological source. Examples of contaminants include bacteria, viruses, fungi, prions, toxins, allergens, spores, any of the agents listed above as biological components, and fragments and derivatives of any of the foregoing. In the context of the invention, a contaminant can also be referred to as a contaminating biological agent.

The term "cross-linked" refers to the attachment of two entities via one or more covalent bonds. Cross-linking may be chemical or genetic. Genetic cross-linking encompasses indicators prepared as fusion proteins.

The term "sample" encompasses any item, instrument, surface, fluid or material. Examples include, but are not limited to clinical samples (such as whole blood, serum, oral samples such as saliva, pus, vaginal samples, stool samples, vomitus), environmental samples (such a water, soil, air samples), surgical and medical instruments, microtitre plates, dipsticks, lateral flow devices, hospital gowns, bedclothes, bulk liquids, culled animal material, pharmaceuticals, workbenches, walls and floors, biological matrices.

The term "treatment" or "treatment process" encompasses any process that is designed to reduce the amount or activity of a contaminant in a sample. Suitable treatments include one or more of: a selected pH (e.g., below pH 1, 2, 3, 4, 5, 6 or 7, or above pH 7, 8, 9, 10 or 11, or about pH 12), temperature (e.g., at least 40 C, 50 C, 60 C, 70 C, 80 C, 90 C, 100 C, 110 C, 120 C, 130 C, 140 C, 150 C, or 160 C, or between 50-120 C) or pressure (e.g., at least 50 kPa, 70 kPa, 100 kPa, 150 kPa, 200 kPa, or 250 kPa), exposing the sample to a protease or other lytic enzyme, exposing the sample to a detergent, a chemical sterilant, radiation, free radicals, or a gas-phase sterilant. In one embodiment, the treatment is designed to reduce the infectious activity (also known as the infectivity) of an infectious biological contaminant, such as TSE. The term "treatment" or "treatment process" also encompasses cleaning and inactivation processes such as high temperature autoclaving with wet or dry steam, ozone sterilisation, $H_2O_2$ sterilisation, rendering or other method designed to eliminate or inactivate the contaminant. In another embodiment of the invention, both the indicator and the contaminant are directly exposed to the treatment process, i.e. there is no seal or barrier between the indicator/contaminant and the treatment process. The indicator and the contaminant are therefore both in direct contact with the treatment process, and are subject to the same treatment conditions.

The term "biological component" encompasses any biological molecule that can be covalently linked to a kinase enzyme. The biological component may be selected from a protein, a nucleic acid, a lipid or a carbohydrate. The biological component is suitably a mimetic or surrogate of the contaminant in the sample to be treated, and therefore reacts to the treatment process in substantially the same way as the contaminant. In one embodiment, the biological component may be the same as, but physically distinct from, the contaminant in the sample that is to be subjected to the treatment process, e.g., if the contaminant is a protein, then the biological component is also a protein; if the contaminant is a blood protein, the biological component is also blood protein; if the contaminant is a DNA molecule, then the biological component is also a DNA molecule; if the contaminant is an RNA molecule then the biological component is also an RNA molecule, etc. for each of the contaminants and biological components disclosed in this specification. In another embodiment, the biological component is different from the contaminant. In one embodiment of the invention, the biological component is not a peptide, protein or polypeptide. In a further embodiment of the invention, the biological component is not an oligonucleotide (e.g., an oligonucleotide probe specific for HPV16). In yet a further embodiment of the invention, the biological component is not a lectin, growth factor, DNA/RNA aptamer, bacteriophage, or a binding agent specific for an analyte.

The term "protein" encompasses any protein- or peptide-containing molecule. The terms "protein", "peptide", and "polypeptide" are used interchangeably in the present specification.

The term "blood protein" encompasses any protein that is present in blood. Specific examples include blood clotting proteins (e.g., fibrinogen, fibrin peptides, fibrin, transglutaminase substrates, thrombin), serum proteins (e.g., albumin and globulin), platelets, blood cell glycoproteins, and haemoglobin.

The term "bacterial protein" encompasses any protein that is derived from a bacterium. Specific examples include a bacterial fimbrial protein (e.g CgsA from *E. coli* and AgfA from *Salmonella*), a bacterial toxin protein (e.g., toxins from *Bacillus anthracis, Corynebacterium diphtheriae, Clostridium botulinum*), a bacterial cell surface protein (e.g., cell surface adhesins from floc forming and filamentous bacteria in activated sludge, peptidoglycan, lipoproteins), and a bacterial spore protein (e.g., from Gram positive bacteria and having a similar sequence or overall structure to the proteins forming ribbon appendages in *Clostridum taeniosporum*, chaplin proteins A-H and rodlin proteins Rd1A and Rd1B from *Streptomyces* spp.)

The term "viral protein" encompasses any protein that is derived from a virus. Specific examples include a viral coat protein, a viral envelope protein, a viral capsid protein, and a viral core protein. In one embodiment, the viral proteins are from a bacteriophage virus (e.g., the MS2 and PP7 coat proteins), norwalk virus (e.g., capsid protein), rotavirus (e.g., VP2, VP6 and VP7 proteins), coronavirus (e.g., SARS S, E and M proteins), bluetongue (e.g., VP2 protein), human papillomavirus (e.g., viral major structural protein, L1), hepatitis B (e.g., small envelope protein HBsAg), Hepatitis C (e.g., core, E1 and E2 proteins), influenza (e.g., neuraminidase and haemagglutinin and matrix proteins), poliovirus (e.g., capsid VP0, 1 and 3 proteins), HIV (e.g., Pr55gag, envelope proteins) and dengue B (e.g., envelope (e) and pre-membrane/membrane (prM/M).

The term "fungal protein" encompasses any protein that is derived from a fungus. Specific examples include hydrophobin proteins (e.g., SC3 from *Schizophyllum commune*, RodA/B from *Aspergillus* fumigates, and equivalent proteins from yeast), fungal spore proteins, hyphal proteins, mycotoxins, and fungal prions (e.g., Sup35, Het S, Ure 2, Rnq1, New 1).

The term "self-aggregating protein" encompasses any protein that is capable of self-aggregating or self-assembling into amyloid fibrils or surface reactive biofilms. Specific examples include prions (e.g., $PrP^{Sc}$ and $PrP^{c}$, Het S, Ure 2, Rnq1, New 1), prion mimetic proteins, amyloid fibrils, cell surface adhesins from floc-forming and filamentous bacteria in activated sludge, beta amyloid protein, tau protein, poly-adenine binding protein, lung surfactant protein C, CsgA protein from *E. coli*, AgfA protein from *Salmonella* species, bacterial fimbrial proteins, apolipoproteins (e.g., apolipoprotein A1), hydrophobins from fungal species (e.g., SC3 from *Schizophyllum commune*, RodA/B from *Aspergillus* fumigates), chaplins (e.g., Chps A-H from *Streptomyces* spp), rodlins (e.g., Rd1A and Rd1B from *streptomyces* spp), gram positive spore coat proteins (e.g., P29a, P29b, GP85 and a SpoVM analogue), and barnacle cement-like proteins (e.g., the 19 kDa protein from *Balanus albicostatus*, and the 20 kDa protein from *Megabalanus rosa*, and the novel calcite-dependent cement-like protein from *Balanus albicostatus*).

The term "nucleic acid" encompasses nucleotide polymers of any length or composition. Specific examples include a DNA molecule and an RNA molecule. In one embodiment, the nucleic acid is selected from single-stranded DNA (ssDNA), single-stranded RNA (ssRNA), double-stranded DNA (dsDNA) or double-stranded RNA (dsRNA). In another embodiment, said molecules are derived from neurological tissue.

The term "carbohydrate" encompasses any carbohydrate-containing molecule. Specific examples include exopolysaccharide, lipopolysaccharide, (EPS/LPS, sometimes known as endotoxin) (e.g., from *Legionella, E. coli, Staphylococcus* species, *Streptococcus* species, *Pseudomonas* species, *Acinetobactor* species, *Campylobactor* species, and *Bacillus* species,) peptidoglycan, cell wall components of plants, fungi and yeast (e.g., chitin, lignin, glucan), mucin preparations, glycolipids (especially brain derived glycolipids), glycoproteins (e.g., cell surface glycoproteins, Eap1p), spore extracts (e.g., from *Bacillus* spp, *Clostridal* spp and other spore-formers), polysaccharides from yeast capsules, and invertebrate secretions (e.g., from molluscan gels).

The term "lipid" encompasses any lipid-containing molecule. Specific examples include glycolipids (e.g., brain-derived glycolipids), gangliosides (e.g., $GT_{1b}$, $GT_{1a}$ and $GM_1$), and plant oils and lipids.

A "transglutaminase substrate" is any molecule that is a substrate for a transglutaminase enzyme. Transglutaminases are a family of enzymes (EC 2.3.2.13) that catalyze the formation of a covalent bond between a free amine group (e.g., protein- or peptide-bound lysine) and the gamma-carboxamid group of protein- or peptide-bound glutamine. Examples of such enzymes include Factor VIII, keratinocyte transglutaminase and tissue transglutaminase. Fibrin, which is acted upon by Factor VIII, is an example of a transglutaminase substrate.

A "biological matrix or mixture" may comprise one or more components selected from the group consisting of proteins, lipids, nucleic acids and carbohydrates. In one embodiment, it may be a mixture of proteins, or may comprise one or more of blood, serum, mucus, egg, neurological tissue, food, or culled animal material. The biological matrix or mixture may also be a commercially available test soil, such as Browne soil or Edinburgh soil. In one embodiment, the biological matrix/mixture has a similar composition to the matrix/mixture in which the contaminant is present. In the context of the invention, a biological matrix can also be referred to as a test soil.

A biological component that is a "mimetic" or "surrogate" of the contaminant is a component that will react to the treatment process in a very similar (or substantially the same) way to the contaminant. Similarly, a biological matrix that is a "mimetic" or "surrogate" of the sample is a matrix that has a similar composition to the sample, and that will react to the treatment process in substantially the same way.

The term "antibody" embraces full length immunoglobulins, and all fragments and derivatives thereof, e.g., a heavy chain, a light chain, a constant domain, a variable domain, an Fab region, an Fc region etc. of an immunoglobulin.

The term "fibrin" embraces all fibrin-derived peptides. This includes full length fibrin peptides and all fragments and derivatives thereof. It embraces all peptides having a fibrin reactivity, e.g., peptides that are acted upon by Factor VIII to form a clot. The term fibrin or fibrin peptide may be used interchangeably with the term "transglutaminase substrate" throughout this specification.

The term "light output" means the light that is emitted by the reaction of ATP with the bioluminescent reagent. This light output can be detected using entirely conventional technology, such as a standard luminometer (e.g., a Berthold Orion 96-well microplate luminometer, or a hand-held luminometer).

The term "reporter kinase" refers to a kinase enzyme that is not inherently present in the sample being tested, i.e. the kinase is exogenous to the sample. Reporter kinase is added to the sample as a separate reagent, e.g as an isolated kinase. In one embodiment, reporter kinases are thermostable.

The term "thermostable kinase" refers to a kinase that retains activity after exposure to heat, i.e. that is relatively unaffected by high temperatures. In one embodiment of the invention, thermostable kinases retain at least 70% activity (or 80% activity, 90% activity, 95% activity, or 100% activity) after exposure to a temperature of between 50-120 C. In another embodiment, thermostable kinases retain at least 70% activity (or 80% activity, 90% activity, 95% activity, or 100% activity) after exposure to 40 C for 30 minutes, or after exposure to 50 C for 30 minutes, or after exposure to 60 C for 30 minutes, or after exposure to 70 C for 30 minutes, or after exposure to 80 C for 20 minutes, or after exposure to 90 C for 10 minutes, or after exposure to 120 C for 3 minutes. Thermostable kinases may also be more resistant than non-thermostable kinases to a range of other biochemical and physical processes that routinely damage or destroy proteins or render them inactive, such as exposure to certain chemicals e.g., chaotropes, free-radical damage, detergents, extremes of pH, exposure to proteases, protein cross-linking, encapsulation within non-permeable or semi-permeable membranes or polymers, or irreversible immobilisation onto surfaces. In a particular embodiment, thermostable kinases may retain at least 70% activity (or 80% activity, 90% activity, 95% activity, or 100% activity) after exposure to one or more of the biochemical and physical processes described above. In all cases, this "retained activity" can be readily confirmed using conventional tests. In brief, the kinase is incubated with ADP under the given treatment conditions for a given amount of time, and then analysed for residual activity by detecting the generation of ATP using luciferin/luciferase and a luminometer. From this, the % of kinase activity retained after the treatment can be determined.

The terms "kinase" and "kinase activity" are used interchangeably throughout this specification.

The term "bioluminescent reagent" refers to any substance or mixture of substances able to react with ATP to generate light, e.g., a mixture of luciferin and luciferase.

The term "RLU" means Relative Light Unit. Relative Light Units are a relative, not absolute, measurement. The figures given in the specification relate to measurements taken using a Berthold Orion 96-well microplate luminometer with injector system using a "flash" method of light measurement for 2 seconds immediately after the addition of the luciferase/luciferin reagents (technical specification photomultiplier measuring light emitted at a wavelength of 300-650 nm). To address this issue, manufacturers have generated data for RLU "factors", which allow the data generated by a given luminometer to be normalised to a calibrated standard. Thus, comparisons can be made between different instruments. The RLU factor for the Berthold Orion 96-well microplate luminometer is 1. Accordingly, the RLU values given in the specification can be regarded as standardised/normalised RLU values.

In terms of absolute values, an RLU value can be related to the concentration of ATP required to give said value with the reagents as described in the method. As an approximate conversion, and given the linear relationship between RLU values and ATP concentration, the following values can be used:

| RLU | Approximate concentration of ATP/μM |
|---|---|
| 12,000,000 | 1000 |
| 1,200,000 | 100 |
| 120,000 | 10 |
| 12,000 | 1 |
| 1,200 | 0.1 |
| 120 | 0.01 |

All references cited in this application are hereby incorporated by reference in their entirety.

BRIEF DESCRIPTION OF THE DRAWINGS

The invention is now described in specific embodiments in the following examples and with reference to the accompanying drawings in which:

(FIG. 1A), 80° C. (FIG. 1B) and 90° C. (FIG. 1C);

FIGS. 2A and 2B show the thermal stability of a range of AK enzymes recombinantly expressed in *E. coli*. Genes encoding AK enzymes were cloned and expressed as described in Example 3. All genes were expressed from the vector pET28a except for *Sacidocaldarius* clone I which was expressed from pET3a as described previously. Expression levels were similar for each clone but a proportion of the *Pyrococcus furiosus* (P.fu) enzyme was in the insoluble fraction and this is likely to have reduced the amount of this enzyme being assayed. The thermal stability of the recombinant enzymes was measured following incubation at 80° C. for 30 minutes in a crude *E. coli* lysate at 10-fold serial dilutions from 1 mg/ml total cellular protein (such that column 12 is equivalent to 1 fg/ml total protein). Enzymes from *Thermotoga maritima* and *Archaeoglobus fulgidus* showed significantly greater stability than the other enzymes tested, although the remaining enzymes (*Sulfolobus solfataricus* (S. so P2), *Aeropyrum pernix* and P.fu) showed similar activity to the *S. acidocaldarius* enzyme used as the basis of previous assays (data labelled as Sac I);

Figure 8:
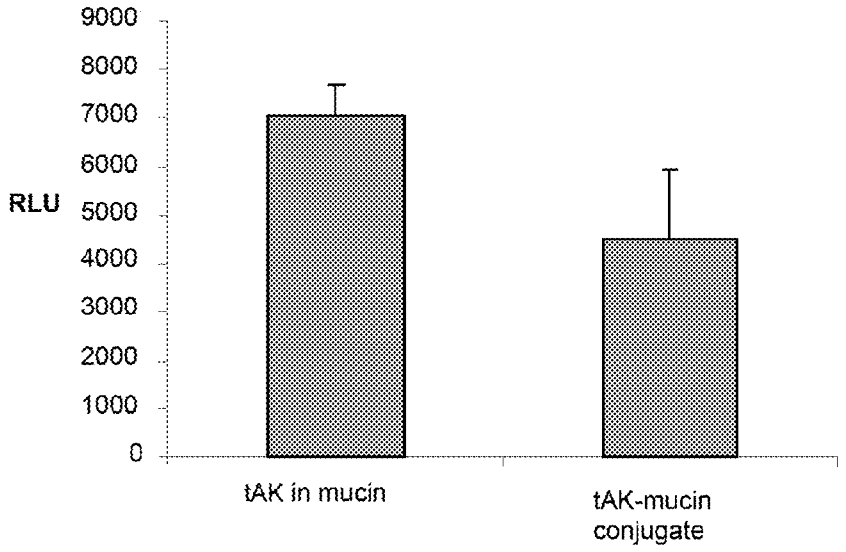
Figure 9:
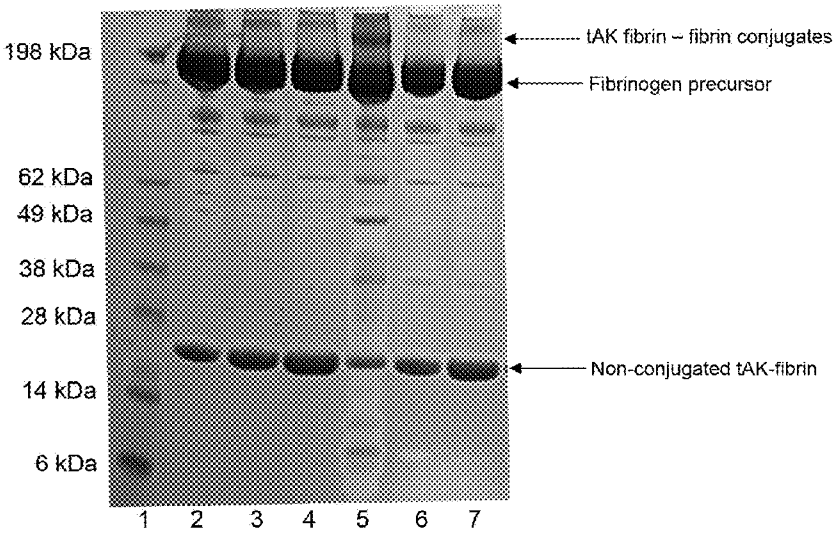

Lane 1, molecular weight markers; Lane 2, tAK conjugated to mucin; Lane 3, tAK-mucin conjugate reduced using DTT. Following SPDP derivatisation of tAK and mucin as described previously, high molecular weight conjugate species are formed <200 kDa. No non-conjugated tAK is present in Lane 2 demonstrating highly efficient cross-linking between the two protein species. Reduction of the conjugate breaks the cross-linking bonds resulting in the appearance of free tAK as indicated in Lane 3;

FIG. 8 shows processing of tAK mucin indicators in a washer-disinfector.

tAK in mucin was prepared by adding unmodified tAK to porcine mucin and allowing tAK to dry on the indicator surface. tAK-mucin conjugate was prepared as described previously using SPDP to cross-link tAK and mucin. The indicators were processed in a validated washer-disinfector using 3E-zyme as the detergent;

FIG. 9 shows SDS-PAGE analysis of the covalent attachment of tAK-fibrin fusion protein with fibrinogen to form a tAK-fibrin film. Lane 1, SeeBlue2 markers; Lane 2, 1:1000 ratio of tAK-fibrin to fibrinogen reaction—non-thrombin activated control; Lane 3, as Lane 2—ratio of 1:500 tAK-fibrin: fibrinogen; Lane 4, as Lane 2, ratio of 1:250 tAK-fibrin: fibrinogen; Lane 5, as Lane 2, thrombin-activated; Lane 6, as Lane 3 thrombin-activated; Lane 7, as Lane 4 thrombin-activated. Reactions were incubated at 37° C. for 1 hour in the presence or absence of 5 U of thrombin, as required. Optimum covalent incorporation was achieved at a ratio tAK-fibrin: fibrinogen of 1:1000 (Lane 5) with higher molecular weight species (<198 kDa) formed as indicated, with a concomitant decrease of non-conjugate tAK-fibrin species (22.1 kDa).

SEQ ID NOS

SEQ ID NO:1 Protein sequence of adenylate kinase from *Sulfolobus solfataricus*

SEQ ID NO:2 Protein sequence of adenylate kinase from *Sulfolobus acidocaldarius*

SEQ ID NO:3 Protein sequence of adenylate kinase from *Sulfolobus tokodaii*

SEQ ID NO:4 Protein sequence of adenylate kinase from *Pyrococcus furiosus*

SEQ ID NO:5 Protein sequence of adenylate kinase from *Pyrococcus horikoshii*

SEQ ID NO:6 Protein sequence of adenylate kinase from *Pyrococcus abyssi*

SEQ ID NO:7 Protein sequence of adenylate kinase from *Methanococcus thermolithotrophicus*

SEQ ID NO:8 Protein sequence of adenylate kinase from *Methanococcus voltae*

SEQ ID NO:9 Protein sequence of adenylate kinase from *Methanococcus jannaschii*

SEQ ID NO:10 Protein sequence of adenylate kinase from *Methanopyrus kandleri*

SEQ ID NO:11 Protein sequence of adenylate kinase from *Methanotorris igneus*

SEQ ID NO:12 Protein sequence of adenylate kinase from *Pyrobaculum aerophilum*

SEQ ID NO:13 Protein sequence of adenylate kinase from *Thermotoga maritima*

SEQ ID NO:14 Protein sequence of adenylate kinase from *Aeropyrum pernix*

SEQ ID NO:15 Protein sequence of adenylate kinase from *Archaeoglobus fulgidus*

SEQ ID NO:16 Protein sequence of adenylate kinase from *Pyrococcus abyssi* (monomeric adenylate kinase (AdkE))

SEQ ID NO:17 Protein sequence of adenylate kinase from *Pyrococcus furiosus* genetically engineered to provide improved stability SEQ ID NO:18 Protein sequence of adenylate kinase from *Pyrococcus horikoshii* genetically engineered to provide improved stability SEQ ID NO:19 Protein sequence of adenylate kinase from *Sulfolobus acidocaldarius* genetically engineered to provide improved stability SEQ ID NO:20 Protein sequence of Acetate kinase from *Thermatoga maritima*

SEQ ID NO:21 Protein sequence of Pyruvate kinase from *Pyrococcus horikoshii*

SEQ ID NO:22 Protein sequence of Pyruvate kinase from *Sulfolobus solfataricus*

SEQ ID NO:23 Protein sequence of Pyruvate kinase from *Thermotoga maritima*

SEQ ID NO:24 Protein sequence of Pyruvate kinase from *Pyrococcus furiosus*

SEQ ID NO:25 Protein sequence of Acetate kinase from *Methanosarcina thermophila*

SEQ ID NO:26 DNA sequence encoding the adenylate kinase from *Sulfolobus acidocaldarius*

SEQ ID NO:27 DNA sequence encoding the adenylate kinase from *Sulfolobus acidocaldarius*, wherein codon usage has been optimised for expression of the gene in *E. coli.*

SEQ ID NO:28 DNA sequence encoding the adenylate kinase from *Thermotoga maritima*

SEQ ID NO:29 DNA sequence encoding the adenylate kinase from, *Thermotoga maritima*, wherein codon usage has been optimised for expression of the gene in *E. coli.*

SEQ ID NO:30 DNA sequence encoding the adenylate kinase from *Archaeoglobus fulgidus*, wherein codon usage has been optimised for expression of the gene in *E. coli.*

SEQ ID NO:31 Protein sequence of adenylate kinase from *Sulfolobus acidocaldarius*, wherein codon usage has been optimised for expression of the gene in *E. coli* (SEQ ID NO:27).

SEQ ID NO:32 Protein sequence of adenylate kinase from *Thermotoga maritima*, wherein codon usage has been optimised for expression of the gene in *E. coli* (SEQ ID NO:29).

SEQ ID NO:33 Protein sequence of transglutaminase substrate

SEQ ID NO:34 Protein sequence of thermostable adenylate kinase from *Sulfolobus acidcaldarius* fused at the N-terminus with a transglutaminase (Factor XIII) substrate sequence SEQ ID NO:35 Protein sequence of thermostable adenylate kinase from *Sulfolobus acidcaldarius* fused at the C-terminus with a transglutaminase (Factor XIII) substrate sequence SEQ ID NO:36 Protein sequence of thermostable adenylate kinase from *Sulfolobus acidcaldarius* fused at the N-terminus and C-terminus with a transglutaminase (Factor XIII) substrate sequence SEQ ID NO:37 DNA sequence of transglutaminase (Factor XIII) substrate sequence fused to the 5' end of adenylate kinase from *Thermotoga maritima.*

SEQ ID NO:38 Protein sequence of adenylate kinase from *Thermotoga maritima* fused at the N-terminal with a transglutaminase (Factor XIII) substrate sequence.

SEQ ID NO:39 DNA sequence of transglutaminase (Factor XIII) substrate sequence fused to the 3' end of adenylate kinase from *Thermotoga maritima.*

SEQ ID NO:40 Protein sequence of adenylate kinase from *Thermotoga maritime* fused at the C-terminal with a transglutaminase (Factor XIII) substrate sequence.

SEQ ID NO:41 DNA sequence of transglutaminase (Factor XIII) substrate sequence fused to both the 5' and 3' ends of adenylate kinase from *Thermotoga maritima.*

SEQ ID NO:42 Protein sequence of adenylate kinase from *Thermotoga maritime* fused at the N- and C-terminal with a transglutaminase (Factor XIII) substrate sequence.

SEQ ID NO:43 DNA sequence of complete Sup35 gene construct from *Saccharomyces cerevisiae*

SEQ ID NO:44 Protein sequence of complete Sup35 from *Saccharomyces cerevisiae*

SEQ ID NO:45 DNA sequence of sup35N (N-terminal domain) codon-biased for optimal expression in *E. coli*

SEQ ID NO:46 Protein sequence of sup35N (N-terminal domain)

SEQ ID NO:47 DNA sequence of *E. coli* codon biased adenylate kinase from *Sulfolobus acidcaldarius* fused at the N-terminus with Sup35 N-terminal domain from *Saccharomyces cerevisiae*

SEQ ID NO:48 Protein sequence of adenylate kinase from *Sulfolobus acidcaldarius* fused at the N-terminus with Sup35 N-terminal domain from *Saccharomyces cerevisiae*

SEQ ID NO:49 DNA sequence of *E. coli* codon biased adenylate kinase from *Sulfolobus acidcaldarius* fused at the C-terminus with Sup35 N-terminal domain from *Saccharomyces cerevisiae*

SEQ ID NO:50 Protein sequence of adenylate kinase from *Sulfolobus acidcaldarius* fused at the C-terminus with Sup35 N-terminal domain from *Saccharomyces cerevisiae*

SEQ ID NO:51 DNA sequence of Sup35N fused at the 5' end of adenylate kinase from *Thermotoga maritima.*

SEQ ID NO:52 Protein sequence of adenylate kinase from *Thermotoga maritima* fused at the N-terminal with Sup35N.

SEQ ID NO:53 DNA sequence of Sup35N fused at the 3' end of adenylate kinase from *Thermotoga maritima.*

SEQ ID NO:54 Protein sequence of adenylate kinase from *Thermotoga maritima* fused at the C-terminal with Sup35N SEQ ID NO:55 DNA sequence encoding a short Sup35 peptide capable of aggregating to form amyloid fibrils; for use as a fusion peptide with tAK genes.

SEQ ID NO:56 Sup35 derived amyloid peptide

SEQ ID NO:57 DNA sequence encoding a Norovirus capsid protein (58 kDa)

SEQ ID NO:58 Protein sequence of Norovirus capsid protein (58 kDa)

SEQ ID NO:59 DNA sequence for a synthetic gene encoding a Norovirus capsid protein (58 kDa) optimised for expression in *E. coli*

SEQ ID NO:60 DNA sequence for a synthetic gene encoding a Norovirus capsid protein (58 kDa) optimised for expression in *E. coli* fused at the 5' end of a gene encoding the tAK from *Thermotoga maritima.*

SEQ ID NO:61 Protein sequence of a Norovirus capsid protein (58 kDa) fused at the N-terminus of the adenylate kinase from *Thermotoga maritima.*

SEQ ID NO:62 Protein sequence of a bacteriophage MS2 coat protein

SEQ ID NO:63 Protein sequence of a bacteriophage PP7 coat protein monomer

SEQ ID NO:64 Protein sequence of a bacteriophage PP7 coat protein dimer

SEQ ID NO:65 Protein sequence of *E. coli* CsgA

SEQ ID NO:66 Protein sequence of *Salmonella* AgfA

SEQ ID NO:67 Protein sequence of adenylate kinase from *Thermotoga maritima* fused to the N terminus of *E. coli* CsgA SEQ ID NO:68 Protein sequence of the hydrophobin 3 protein from *Fusarium* species SEQ ID NO:69 Protein sequence of the hydrophobin 5 protein from *Fusarium* species SEQ ID NO:70 Protein sequence of cement-like protein from *Balanus albicostatus* (19K)

SEQ ID NO:71 Protein sequence of cement-like protein from *Megabalanus rosa* (20 k)

SEQ ID NO:72 Protein sequence of fusion of the barnacle protein from *Balanus albicostatus* with the tAK from *Thermotoga maritima*; N-terminal fusion SEQ ID NO:73 Protein sequence of fusion of the barnacle protein from *Balanus albicostatus* with the tAK from *Thermotoga maritima*; C-terminal fusion SEQ ID NO:74 Protein sequence of *Balanus albicostatus* calcite-specific adsorbent SEQ ID NO:75 Protein sequence of a peptide derived from a barnacle cement protein SEQ ID NO:76 Protein sequence of a peptide derived from a barnacle cement protein SEQ ID NO:77 Protein sequence of a peptide derived from a barnacle cement protein

EXAMPLE 1

Purification of Native Adenylate Kinase Enzymes

Biomass was produced from twenty-four diverse thermophilic and hyperthermophilic microorganisms (Table 1).

Eight members of the archaea were represented along with sixteen diverse aerobic and anaerobic bacteria. AKs from each of these organisms was purified by affinity chromatography using selective absorption and desorption from Cibacron Blue 3A (Blue Sepharose). All enzymes were further characterised and purified by gel filtration (Superdex G200). This enabled identification of the major AK fraction and estimation of molecular mass.

TABLE 1

List of thermophilic organisms cultured to produce biomass for isolation of thermostable AKs.

| | Organism | Domain | Growth | $T_{opt}$ | $pH_{opt}$ |
|---|---|---|---|---|---|
| 1 | *Aeropyrum pernix* | Archaeon | Aerobe | 95° C. | 7.0 |
| 2 | *Alicyclobacillus acidocaldarius* | Bacterium | Aerobe | 65° C. | 3.5 |
| 3 | *Aquifex pyrophilus* | Bacterium | Microaerophileeberophile | 85° C. | 6.5 |
| 4 | *Bacillus caldotenax* BT1 | Bacterium | Aerobe | 65° C. | 7.0 |
| 5 | *Bacillus species* PS3 | Bacterium | Aerobe | 65° C. | 7.0 |
| 6 | *Bacillus stearothermophilus* 11057 | Bacterium | Aerobe | 65° C. | 7.0 |
| 7 | *Bacillus stearothermophilus* 12001 | Bacterium | Aerobe | 65° C. | 7.0 |
| 8 | *Bacillus thermocatenulatus* | Bacterium | Aerobe | 65° C. | 7.0 |
| 9 | *Clostridium stercocorarium* | Bacterium | Anaerobe | 55° C. | 7.0 |
| 10 | *Meiothermus ruber* | Bacterium | Aerobe | 60° C. | 6.5 |
| 11 | *Pyrococcus furiosus* | Archaeon | Anaerobe | 95° C. | 7.5 |
| 12 | *Pyrococcus horikoshii* | Archaeon | Anaerobe | 95° C. | 7.0 |
| 13 | *Pyrococcus woesei* | Archaeon | Anaerobe | 95° C. | 7.0 |
| 14 | *Rhodothermus marinus* | Bacterium | Aerobe | 70° C. | 6.5 |
| 15 | *Sulfolobus acidocaldarius* 98-3 | Archaeon | Aerobe | 75° C. | 2.5 |
| 16 | *Sulfolobus shibatae* B21 | Archaeon | Aerobe | 75° C. | 2.5 |
| 17 | *Sulfolobus solfataricus* P2 | Archaeon | Aerobe | 75° C. | 2.5 |
| 18 | *Thermoanaerobacter ethanolicus* | Bacterium | Anaerobe | 65° C. | 6.0 |
| 19 | *Thermoanaerobacter thermosulfurogenes* | Bacterium | Anaerobe | 65° C. | 6.5 |
| 20 | *Thermobrachium celere* | Bacterium | Anaerobe | 60° C. | 7.0 |
| 21 | *Thermococcus litoralis* | Archaeon | Anaerobe | 85° C. | 6.5 |
| 22 | *Thermus aquaticus* YT1 | Bacterium | Aerobe | 70° C. | 8.0 |
| 23 | *Thermus caldophilus* GK24 | Bacterium | Aerobe | 70° C. | 8.0 |
| 24 | *Thermus thermophilus* HB8 | Bacterium | Aerobe | 70° C. | 8.0 |

EXAMPLE 2

Analysis of Thermostability of Native Adenylate Kinases

Figure 1A:
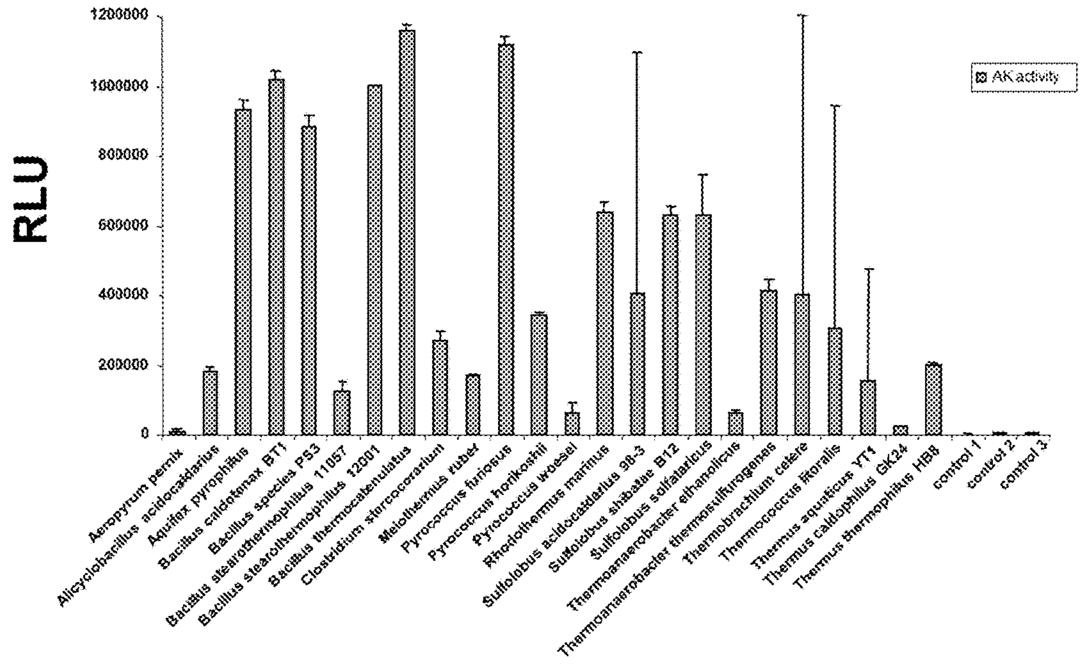
FIGS. 1A, 1B, and 1C show activity of adenylate kinase (AK) enzymes after treatment at 70° C.
Figure 1B:
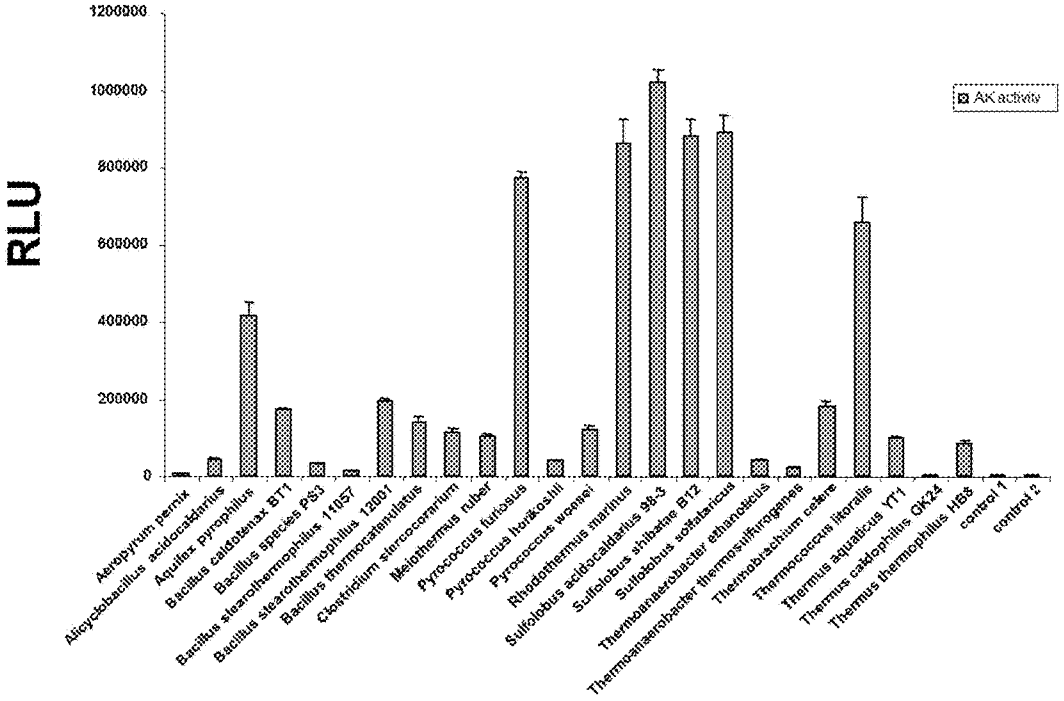
Figure 1C:
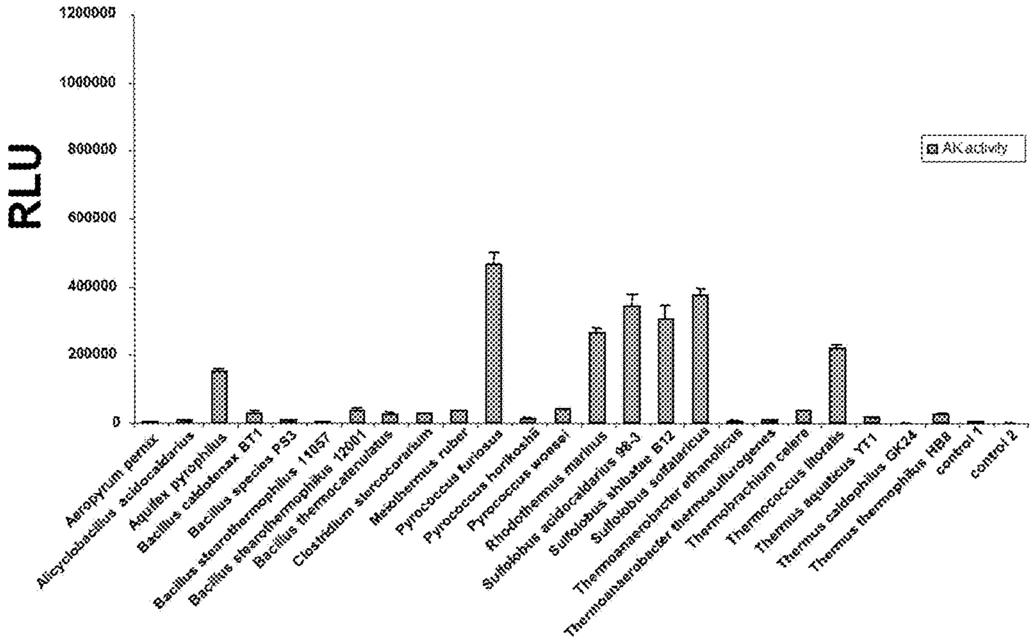

The thermostability at 70° C., 80° C., and 90° C. of adenylate kinases isolated from biomass from thermophilic organisms was assessed, and the results shown in FIG. 1A, 1B, 1C.

The adenylate kinases were isolated from the biomass by affinity chromatography using selective absorption and desorption from Cibacron Blue 3A (Blue Sepharose). The samples eluted from the columns were diluted 1:10 000 and then 10 μl of each added to a microtitre well. 2.5 μl of apyrase was added to each well to destroy the ATP present from the elution buffer, and incubated at 37° C. for 30 minutes. The apyrase was inactivated by heat treatment at 65° C. for 20 minutes.

ADP substrate was added and incubated at either 70 (panel A), 80 (panel B) or 90° C. (panel C) for 30 minutes and cooled to 25° C. before the addition of 10 μl of D-luciferin-luciferase reagent. The ATP produced was measured as RLU on a plate luminometer.

EXAMPLE 3

Expression and Purification of Recombinant Adenylate Kinases

Clones expressing representative thermostable AKs were secured and recombinant thermostable AKs from the thermoacidophilic archaeon *Sulfolobus acidocaldarius* and the thermophilic bacterium, *Bacillus stearothermophilus* produced. The plasmids were transformed into *E. coli* and the cell extracts shown to contain protein bands on electrophoresis corresponding to the expected molecular masses of the AKs. Thermostable AK activity was measured after incubation at the appropriate temperature (80° C. for the *Sulfolobus acidocaldarius* AK and 60° C. for the *Bacillus stearothermophilus* AK).

Purification methods for both thermostable AKs were established and included an initial heat treatment of incubation for 20 minutes at 80° C., to inactivate and aggregate proteins derived from *E. coli*, followed by affinity chromatography and gel filtration. The affinity chromatography involved adsorption of the enzyme to Blue Sepharose, followed by specific elution with a low concentration of AK co-factors (AMP+ATP and magnesium ions). The ATP and AMP (Sigma) in the elution buffer were degraded by incubation with mesophile apyrase, which is readily inactivated by subsequent heat treatment. Gel filtration chromatography was scaled up to utilise a preparation grade Superdex column to enable large quantities of both enzymes to be prepared.

Primers were designed for PCR amplification of the AK genes from the thermophilic organisms identified during the screening of candidate native enzymes.

The thermostable microorganisms were grown using individually defined growth conditions and genomic DNA isolated and used as templates for PCR amplification of the adenylate kinase genes from each organism. PCR amplified adenylate kinase genes from the thermophilic organisms, *Thermotoga maritima, Aeropyrum pernix, Sulfolobus acidocaldarius* and *Sulfolobus solfataricus* were sub-cloned into the vector, pET28a and transformed into a codon enhanced *E. coli* strain expressing rare tRNAs (Zdanovsky et al., 2000). This *E. coli* strain is suitable for enhancing expression levels of AT-rich genes.

The success of the transformation was assessed by a mini-expression study, and the results analysed by SDS-PAGE of the culture supernatants before and after induction with IPTG. SDS-PAGE was also used to analyse the supernatants after inclusion of a heat treatment step, which consisted of heating the sample to 80° C. for 20 minutes prior to running on the SDS-PAGE gel to remove heat labile proteins present in the sample.

Sequences:

adenylate kinase from *Sulfolobus solfataricus*

SEQ ID NO: 1

MKIGIVTGIP GVGKTTVLSF ADKILTEKGI SHKIVNYGDY MLNTALKEGY

VKSRDEIRKL QIEKQRELQA LAARRIVEDL SLLGDEGIGL IDTHAVIRTP

AGYLPGLPRH VIEVLSPKVI FLLEADPKII LERQKRDSSR ARTDYSDTAV

INEVIQFARY SAMASAVLVG ASVKVVVNQE GDPSIAASEI INSLM adenylate kinase from *Sulfolobus acidocaldarius*

SEQ ID NO: 2

MKIGIVTGIP GVGKSTVLAK VKEILDNQGI NNKIINYGDF MLATALKLGY

AKDRDEMRKL SVEKQKKLQI DAAKGIAEEA RAGGEGYLFI DTHAVIRTPS

GYLPGLPSYV ITEINPSVIF LLEADPKIIL SRQKRDTTRN RNDYSDESVI

LETINFARYA ATASAVLAGS TVKVIVNVEG DPSIAANEII RSMK adenylate kinase from *Sulfolobus tokodaii*

SEQ ID NO: 3

MSKMKIGIVT GIPGVGKTTV LSKVKEILEE KKINNKIVNY GDYMLMTAMK

LGYVNNRDEM RKLPVEKQKQ LQIEAARGIA NEAKEGGDGL LFIDTHAVIR

TPSGYLPGLP KYVIEEINPR VIFLLEADPK VILDRQKRDT SRSRSDYSDE

RIISETINFA RYAAMASAVL VGATVKIVIN VEGDPAVAAN EIINSML adenylate kinase from *Pyrococcus furiosus*

SEQ ID NO: 4

MPFVVIITGI PGVGKSTITR LALQRTKAKF RLINFGDLMF EEAVKAGLVK

HRDEMRKLPL KIQRELQMKA AKKITEMAKE HPILVDTHAT IKTPHGYMLG

LPYEVVKTLN PNFIVIIEAT PSEILGRRLR DLKRDRDVET EEQIQRHQDL

NRAAAIAYAM HSNALIKIIE NHEDKGLEEA VNELVKILDL AVNEYA adenylate kinase from *Pyrococcus horikoshii*

SEQ ID NO: 5

MPFVVIITGI PGVGKSTITK LALQRTRAKF KLINFGDLMF EEALKLKLVK

HRDEMRKLPL EVQRELQMNA AKKIAEMAKN YPILLDTHAT IKTPHGYLLG

LPYEVIKILN PNFIVIIEAT PSEILGRRLR DLKRDRDVET EEQIQRHQDL

NRAAAITYAM HSNALIKIIE NHEDKGLEEA VNELVKILDL AVKEYA adenylate kinase from *Pyrococcus abyssi*

SEQ ID NO: 6

MSFVVIITGI PGVGKSTITR LALQRTKAKF KLINFGDLMF EEAVKAGLVN

HRDEMRKLPL EIQRDLQMKV AKKISEMARQ QPILLDTHAT IKTPHGYLLG

LPYEVIKTLN PNFIVIIEAT PSEILGRRLR DLKRDRDVET EEQIQRHQDL

NRAAAIAYAM HSNALIKIIE NHEDKGLEEA VNELVEILDL AVKEYA adenylate kinase from *Methanococcus thermolithotrophicus*

SEQ ID NO: 7

MKNKLVVVTG VPGVGGTTIT QKAMEKLSEE GINYKMVNFG TVMFEVAQEE

NLVEDRDQMR KLDPDTQKRI QKLAGRKIAE MVKESPVVVD THSTIKTPKG

YLPGLPVWVL NELNPDIIIV VETSGDEILI RRLNDETRNR DLETTAGIEE

HQIMNRAAAM TYGVLTGATV KIIQNKNNLL DYAVEELISV LR adenylate kinase from *Methanococcus voltae*

SEQ ID NO: 8

MKNKVVVVTG VPGVGSTTSS QLAMDNLRKE GVNYKMVSFG SVMFEVAKEE

NLVSDRDQMR KMDPETQKRI QKMAGRKIAE MAKESPVAVD THSTVSTPKG

YLPGLPSWVL NELNPDLIIV VETTGDEILM RRMSDETRVR DLDTASTIEQ

-continued

HQFMNRCAAM SYGVLTGATV KIVQNRNGLL DQAVEELTNV LR adenylate kinase from *Methanococcus jannaschii*

SEQ ID NO: 9

MMMMKNKVVV IVGVPGVGST TVTNKAIEEL KKEGIEYKIV NFGTVMFEIA

KEEGLVEHRD QLRKLPPEEQ KRIQKLAGKK IAEMAKEFNI VVDTHSTIKT

PKGYLPGLPA WVLEELNPDI IVLVEAENDE ILMRRLKDET RQRDFESTED

IGEHIFMNRC AAMTYAVLTG ATVKIIKNRD FLLDKAVQEL IEVLK adenylate kinase from *Methanopyrus kandleri*

SEQ ID NO: 10

MGYVIVATGV PGVGATTVTT EAVKELEGYE HVNYGDVMLE IAKEEGLVEH

RDEIRKLPAE KQREIQRLAA RRIAKMAEEK EGIIVDTHCT IKTPAGYLPG

LPIWVLEELQ PDVIVLIEAD PDEIMMRRVK DSEERQRDYD RAHEIEEHQK

MNRMAAMAYA ALTGATVKII ENHDDRLEEA VREFVETVRS L adenylate kinase from *Methanotorris igneus*

SEQ ID NO: 11

MKNKVVVVTG VPGVGGTTLT QKTIEKLKEE GIEYKMVNFG TVMFEVAKEE

GLVEDRDQMR KLDPDTQKRI QKLAGRKIAE MAKESNVIVD THSTVKTPKG

YLAGLPIWVL EELNPDIIVI VETSSDEILM RRLGDATRNR DIELTSDIDE

HQFMNRCAAM AYGVLTGATV KIIKNRDGLL DKAVEELISV LK adenylate kinase from *Pyrobaculum aerophilum*

SEQ ID NO: 12

MKIVIVALPG SGKTTILNFV KQKLPDVKIV NYGDVMLEIA KKRFGIQHRD

EMRKKIPVDE YRKVQEEAAE YIASLTGDVI IDTHASIKIG GGYYPGLPDR

IISKLKPDVI LLLEYDPKVI LERRKKDPDR FRDLESEEEI EMHQQANRYY

AFAAANAGES TVHVLNFRGK PESRPFEHAE VAAEYIVNLI LRTRQKS adenylate kinase from *Thermotoga maritima*

SEQ ID NO: 13

MMAYLVFLGP PGAGKGTYAK RIQEKTGIPH ISTGDIFRDI VKKENDELGK

KIKEIMEKGE LVPDELVNEV VKRRLSEKDC EKGFILDGYP RTVAQAEFLD

SFLESQNKQL TAAVLFDVPE DVVVQRLTSR RICPKCGRIY NMISLPPKED

ELCDDCKVKL VQRDDDKEET VRHRYKVYLE KTQPVIDYYG KKGILKRVDG

TIGIDNVVAE VLKIIGWSDK adenylate kinase from *Aeropyrum pernix*

SEQ ID NO: 14

MKVRHPFKVV VVTGVPGVGK TTVIKELQGL AEKEGVKLHI VNFGSFMLDT

AVKLGLVEDR DKIRTLPLRR QLELQREAAK RIVAEASKAL GGDGVLIIDT

HALVKTVAGY WPGLPKHVLD ELKPDMIAVV EASPEEVAAR QARDTTRYRV

DIGGVEGVKR LMENARAASI ASAIQYASTV AIVENREGEA AKAAEELLRL IKNL adenylate kinase from *Archaeglobus fulgidus*

SEQ ID NO: 15

MNLIFLGPPG AGKGTQAKRV SEKYGIPQIS TGDMLREAVA KGTELGKKAK

EYMDKGELVP DEVVIGIVKE RLQQPDCEKG FILDGFPRTL AQAEALDEML

KELNKKIDAV INVVVPEEEV VKRITYRRTC RNCGAVYHLI YAPPKEDNKC

DKCGGELYQR DDKEETVRE RYRVYKQNTE PLIDYYRKKG ILYDVDGTKD

IEGVWKEIEA ILEKIKS

-continued

Monomeric adenylate kinase (AdkE) from *Pyrococcus abyssi*

SEQ ID NO: 16

MNILIFGPPG SGKSTQARRI TERYGLTYIA SGDIIRAEIK ARTPLGIEME

RYLSRGDLIP DTIVNTLIIS KLRRVRENFI MDGYPRTPEQ VITLENYLYD

HGIKLDVAID IYITKEESVR RISGRRICSK CGAVYHVEFN PPKVPGKCDI

CGGELIQRPD DRPEIVEKRY DIYSKNMEPI IKFYQKQGIY VRIDGHGSID

EVWERIRPLL DYIYNQENRR

EXAMPLE 4

Analysis of the Thermostability of Recombinant Adenylate Kinases

The thermal stability of recombinant tAK enzymes was assessed in crude *E. coli* cell lysates.

Cells were grown essentially as described in Example 3 and lysed by sonication. The AK activity of the crude extract was determined both before and after heat treatment at 80° C. for 30 minutes followed by 10-fold serial dilution The results (see FIGS. 2A and 2B) demonstrate that a wide variety of recombinant enzymes are suitable for the use in the method of the invention. In one embodiment, the AKs are those from *T. maritima, A. fulgidus* and *S. solfataricus*. Such enzymes are likely to provide a greater dynamic range for the bioluminescent assay, if required, to provide still further sensitivity.

EXAMPLE 5

Genetic Modification of Adenylate Kinases to Improve Stability

Site-directed mutants were constructed in the AK gene from *P. furiosus, P. horikoshii* and *S. acidocaldarius* as shown in Examples 6-8 and SEQ ID NOS:17-19 respectively, using standard methods known to those familiar with the art.

In addition to specific changes identified in each gene, the regions underlined in the *S. acidocaldarius* sequence form the core packing region of the archaeal adenylate kinase trimer structure. Hence amino acid substitutions that disturb the packing of this region are likely to have a major effect in decreasing the thermal and physical stability of the enzyme. Conversely amino acid substitutions that improve the core packing, in particular hydrophobic residues with large side chains, may stabilise the enzyme to heat or other processes. Therefore in addition to the specific mutations already described a number of "selective" approaches were used with localised gene shuffling of related gene sequences in these regions (essentially as described in Stemmer (1994) Nature 370:389-391 and Crameri et al. (1996) *Nature Biotech.* 14:315-319) and random PCR-based mutagenesis using degenerate oligonucleotides or modified nucleotide mixes (e.g., Vartanian et al. (1996) *Nucleic Acid Res.* 24:2627-2633). A number of these modifications show altered stability when assessed by recombinant expression in *E. coli* and rapid assay of adenylate kinase activity in lysed cells at high temperature.

EXAMPLE 6

Adenylate Kinases from *Pyrococcus furiosus* Genetically Engineered to Provide Improved Stability (SEQ ID NO. 17)

MPFVVIITGI PGVGKSTITR LALQRTKAKF RLINFGDLMF

EEAVKAGLVK HRDEMRKLPL (K TO E) IQRELQMKA AKKI (T TO A) EMAKE HPILVDTHAT IKTPHGY (M TO L) LG

LPYEVVKTLN PNFIVIIEAT PSEILGRRLR DLKRDRDVET

EEQIQRHQDL NRAAAIAYAM HSNALIKIIE NHEDKGLEEA

VNELVKILDL AVNEYA

Mutations at one or more or all of the sites indicated modify the thermostability of the enzyme. In addition to the three defined changes highlighted, modification of the alanine at position 157 to another small hydrophobic residue (such as I, L) or larger hydrophobic residue (such as F) increases the thermostability of the recombinant protein. Hence, there are 35 variants possible through combination of modifications at these sites. Modification of amino acid 157 to a polar residue such as the T (as observed at the equivalent position in AdkA of *P. horikoshii*), S Y, D, E, K, R results in a decrease in stability.

EXAMPLE 7

Adenylate Kinases from *Pyrococcus horikoshii* Genetically Engineered to Provide Improved Stability (SEQ ID NO. 18)

The modification of either or both of the residues shown in bold and underlined increases the thermal stability of the enzyme (3 variants are possible).

MPFVVIITGI PGVGKSTITK LALQRTRAKF KLINFGDLMF

EEALKLGLVK HRDEMRKLPL EVQRELQMNA AKKIAEMAKN

YPILLDTHAT IKTPHGYLLG LPYEVIKILN PNFIVIIEAT

PSEILGRRLR DLKRDRDVET EEQIQRHQDL NRAAAIAYAM

HSNALIKIIE NHEDKGLEEA VNELVKILDL AVKEYA

EXAMPLE 8

Adenylate Kinase from *Sulfolobus acidocaldarius* Genetically Engineered to Provide Improved Stability (SEQ ID NO. 19).

The modification of the underlined residues shown can increase the thermal stability of the enzyme.

MKIGIVTGIP GVGKSTVLAK VKEILDNQGI NNKIINYGDF

MLATALKLGY AKDRDEMRKL SVEKQKKLQI DAAKGIAEEA

RAGGEGYLFI DTHAVIRTPS GY (A TO M) PGLPSYV

-continued

ITEINPSVIF LLEADPKIIL SRQKRDTTRN RNDYSDESVI

LETINFARYA ATASAVLAGS TVKVIVNVEG DPSIAANEII RSMK

EXAMPLE 9

Expression of Acetate and Pyruvate Kinases

Following the methods of Example 3, we expressed acetate and pyruvate kinases:

Acetate kinase from *Thermatoga maritima*

SEQ ID NO: 20

MRVLVINSGS SSIKYQLIEM EGEKVLCKGI AERIGIEGSR LVHRVGDEKH

VIERELPDHE EALKLILNTL VDEKLGVIKD LKEIDAVGHR VVHGGERFKE

SVLVDEEVLK AIEEVSPLAP LHNPANLMGI KAAMKLLPGV PNVAVFDTAF

HQTIPQKAYL YAIPYEYYEK YKIRRYGFHG TSHRYVSKRA AEILGKKLEE

LKIITCHIGN GASVAAVKYG KCVDTSMGFT PLEGLVMGTR SGDLDPAIPF

FIMEKEGISP QEMYDILNKK SGVYGLSKGF SSDMRDIEEA ALKGDEWCKL

VLEIYDYRIA KYIGAYAAAM NGVDAIVFTA GVGENSPITR EDVCSYLEFL

GVKLDKQKNE ETIRGKEGII STPDSRVKVL VVPTNEELMI ARDTKEIVEK IGR

Pyruvate kinase from *Pyrococcus horikoshii*

SEQ ID NO: 21

MRRMKLPSHK TKIVATIGPA TNSKKMIKKL IEAGMNVARI NFSHGTFEEH

AKIIEMVREQ SQKLDRRVAI LADLPGLKIR VGEIKGGYVE LERGEKVTLT

TKDIEGDETT IPVEYKDFPK LVSKGDVIYL SDGYIVLRVE DVKENEVEAV

VISGGKLFSR KGINIPKAYL PVEAITPRDI EIMKFAIEHG VDAIGLSFVG

NVYDVLKAKS FLERNGAGDT FVIAKIERPD AVRNFNEILN AADGIMIARG

DLGVEMPIEQ LPILQKRLIR KANMEGKPVI TATQMLVSMT MEKVPTRAEV

TDVANAILDG TDAVMLSEET AVGKFPIEAV EMMARIAKVT EEYRESFGIT

RMREFLEGTK RGTIKEAITR SIIDAICTIG IKFILTPTKT GRTARLISRF KPKQWILAFS

TREKVCNNLM FSYGVYPFCM EEGFNENDIV RLIKGLGLVG SDDIVLMTEG

KPIEKTVGTN SIKIFQIA

Pyruvate kinase from *Sulfolobus solfataricus*

SEQ ID NO: 22

MRKTKIVATL GPSSEEKVKE LAEYVDVFRI NFAHGDETSH RKYFDLIRTY

APESSIIVDL PGPKLRLGEL KEPIEVKKGD KIVFSQKDGI PVDDELFYSA

VKENSDILIA DGTIRVRVKS KAKDRVEGTV IEGGILLSRK GINIPNVNLK

SGITDNDLKL LKRALDLGAD YIGLSFVISE NDVKKVKEFV GDEAWVIAKI

EKSEALKNLT NIVNESDGIM VARGDLGVET GLENLPLIQR RIVRTSRVFG

KPVILATQVL TSMINSPIPT RAEIIDISNS IMQGVDSIML SDETAIGNYP

VESVRTLHNI ISNVEKSVKH RPIGPLNSES DAIALAAVNA SKVSKADVIV

VYSRSGNSIL RVSRLRPERN IIGVSPDPRL AKKFKLCYGV IPISINKKMQ

SIDEIIDVSA KLMQEKIKDL KFKKIVIVGG DPKQEAGKTN FVIVKTLEQQ KK

Pyruvate kinase from *Thermotoga maritima*

SEQ ID NO: 23

MRSTKIVCTV GPRTDSYEMI EKMIDLGVNV FRINTSHGDW NEQEQKILKI

KDLREKKKKP VAILIDLAGP KIRTGYLEKE FVELKEGQIF TLTTKEILGN

EHIVSVNLSS LPKDVKKGDT ILLSDGEIVL EVIETTDTEV KTVVKVGGKI

-continued

```
THRRGVNVPT ADLSVESITD RDREFIKLGT LHDVEFFALS FVRKPEDVLK

AKEEIRKHGK EIPVISKIET KKALERLEEI IKVSDGIMVA RGDLGVEIPI

EEVPIVQKEI IKLSKYYSKP VIVATQILES MIENPFPTRA EVTDIANAIF

DGADALLLTA ETAVGKHPLE AIKVLSKVAK EAEKKLEFFR TIEYDTSDIS

EAISHACWQL SESLNAKLII TPTISGSTAV RVSKYNVSQP IVALTPEEKT

YYRLSLVRKV IPVLAEKCSQ ELEFIEKGLK KVEEMGLAEK GDLVVLTSGV

PGKVGTTNTI RVLKVD
```

Pyruvate kinase from *Pyrococcus furiosus*

SEQ ID NO: 24

```
MRRVKLPSHK TKIVATIGPA TNSRKMIKQL IKAGMNVARI NFSHGSFEEH

ARVIEIIREE AQKLDRRVAI LADLPGLKIR VGEIKGGYVE LKRGEKVILT

TKDVEGDETT IPVDYKGFPN LVSKGDIIYL NDGYIVLKVE NVRENEVEAV

VLSGGKLFSR KGVNIPKAYL PVEAITPKDF EIMKFAIEHG VDAIGLSFVG

SVYDVLKAKS FLEKNNAEDV FVIAKIERPD AVRNFDEILN AADGIMIARG

DLGVEMPIEQ LPILQKKLIR KANMEGKPVI TATQMLVSMT TEKVPTRAEV

TDVANAILDG TDAVMLSEET AIGKFPIETV EMMGKIAKVT EEYRESFGLS

RIREFMEIKK GTIKEAITRS IIDAICTIDI KFILTPTRTG RTARLISRFK PKQWILAFST

NERVCNNLMF SYGVYPFCLE EGFDENDIVR LIKGLGLVES DDMVLMTEGK

PIEKTVGTNS IKIFQIA
```

Acetate kinase from *Methanosarcina thermophila*

SEQ ID NO: 25

```
MKVLVINAGS SSLKYQLIDM TNESALAVGL CERIGIDNSI ITQKKFDGKK

LEKLTDLPTH KDALEEVVKA LTDDEFGVIK DMGEINAVGH RVVHGGEKFT

TSALYDEGVE KAIKDCFELA PLHNPPNMMG ISACAEIMPG TPMVIVFDTA

FHQTMPPYAY MYALPYDLYE KHGVRKYGFH GTSHKYVAER AALMLGKPAE

ETKIITCHLG NGSSITAVEG GKSVETSMGF TPLEGLAMGT RCGSIDPAIV

PFLMEKEGLT TREIDTLMNK KSGVLGVSGL SNDFRDLDEA ASKGNRKAEL

ALEIFAYKVK KFIGEYSAVL NGADAVVFTA GIGENSASIR KRILTGLDGI

GIKIDDEKNK IRGQEIDIST PDAKVRVFVI PTNEELAIAR ETKEIVETEV KLRSSIPV
```

EXAMPLE 10

Preparation of a Fibrin-Based Indicator Device

Preparation of tAK Fusions for Cross-Linking to Fibrin.

A transglutaminase substrate sequence (MNQEQVS-PLGG—SEQ ID NO:33) is added on to the N-terminus, the C-terminus, or both N- and C-termini, of the thermostable adenylate kinase from *S. acidocaldarius* encoded by a codon optimised gene clone. (The transglutaminase substrate sequence is interchangeably referred to in these Examples as fibrin, the fibrin peptide or the transglutaminase substrate). This construct is transferred as an NdeI-SalI fragment into an in-house expression vector (pMTL 1015; as described in WO 2005/123764). The expression construct is confirmed by DNA sequencing and transferred into expressions hosts BL21 or RV308 for subsequent expression.

Similarly, the resynthesised tAK gene from *Thermatoga maritima* (SEQ ID NO:29) is fused to the transglutaminase sequence in the three orientations identified above. The cloning and preparation of the expression system is also as described above.

The fusion constructs can also be expressed in other expression vector-host combinations with the addition of affinity tags for subsequent purification. Particularly useful in this context are expression vectors which add 6-histidine tags on either the N- or C-terminus of the fusion proteins, modifications which aid purification and detection but do not interfere with the intrinsic properties of the fusion proteins. Vectors for this type of modification include pET series vectors (Novagen/Merck) and pQE series vectors (Qiagen).

To generate material for the indicator devices the expression strains are grown initially in 8-liter fermenters essentially under static culture conditions. In brief, the strains are prepared as seed stocks and subsequently diluted into the 8-liters of growth media (modified terrific broth containing additional glucose). The cultures are grown under standard fermentation conditions until the cultures reached an optical density (OD at 600 nm) demonstrating that they are entering stationary conditions (typically at around an OD=5). The fermenters are then held under minimally aerated conditions for up to 12 hours prior to harvesting of material by continual centrifugation.

Purification of tAK Fusions.

The harvested material is then purified according to the following protocol.

Buffer A: 20 mM Tris-HCl; 900 mM NaCl, pH 7.5

Wash Buffer: 20 mM Tris-HCl; 200 mM NaCl, pH 7.5

Buffer B: 20 mM Tris-HCl; 200 mM NaCl, pH 7.5; 10 mM ATP; 10 mM AMP; 10 mM $MgCl_2$ MgAc buffer: 15 mM MgAc (1M Fluka BioChemika), pH 6.8

1. Weigh frozen cell paste (10 g) and resuspend in 3× (30 ml) volume of Buffer A, pH 7.5.
2. Sonicate on ice (~12,000 khz) using 25 cycles of 30 seconds on/30 seconds off Take 1 ml sample.
3. Sonicated cell solution is centrifuged at 6,000 rpm for 30 minutes at 4° C. Supernatant carefully poured off and 1 ml sample taken.
4. Supernatant is heat treated at 80° C. in a water bath for 20 minutes. 1 ml sample taken. (This step is an optional step depending on thermal stability of the fusion proteins).
5. Heat treated solution centrifuged at 6000 rpm for 30 minutes at 4° C. Pour off supernatant and take 1 ml sample.
6. Filter the sample with 0.2 μm low binding filter before loading onto column.
7. Equilibrate Blue Sepharose Fast Flow column with 5 column volumes (CVs) of Buffer A.
8. Load the sample. Wash column with wash buffer at 0.2 ml/min overnight.
9. Elute protein with 100% buffer B at a flow rate of 1 ml/min collect product in 2.5 ml fractions.
10. Once all proteins have eluted wash column with 100% buffer B at 5 ml/min for 5 CV's.
11. Re-equilibrate column with 5 CV's buffer A.
12. Rinse column with 5 CV's 20% ethanol for storage at 4° C.

Optionally, additional protein purification methods are applied to yield a higher purity product. Ion exchange chromatography on either SP-Sepharose Fast Flow or Q-Sepharose Fast Flow resins is particularly effective.

Figure 3:
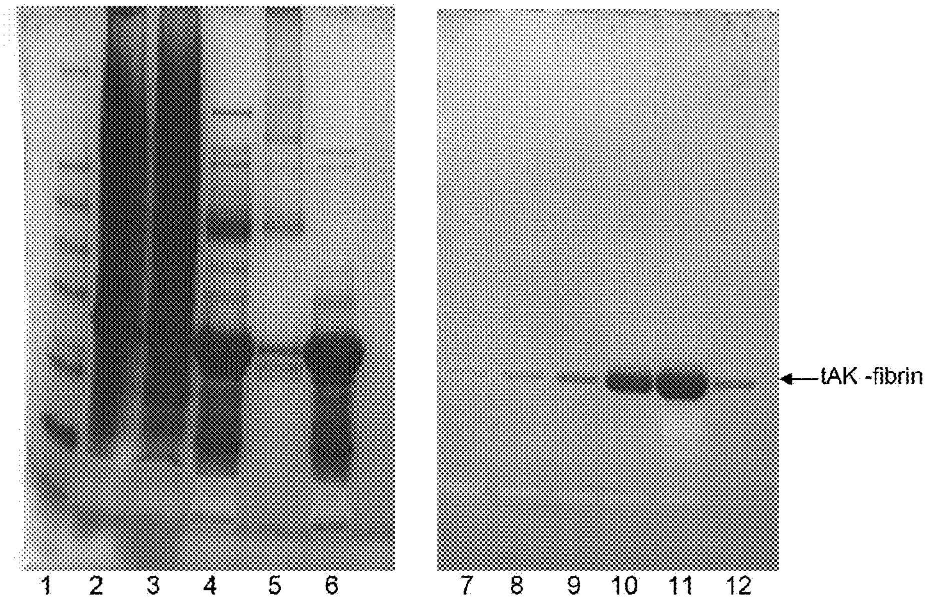
FIG. 3 shows gel electrophoretic analysis (SDS-PAGE) of the expression and purification of tAK-fibrin peptide fusions. Lane 1, Seeblue markers; Lane 2, whole cell homogenate; Lane 3, insoluble pellet (P1); Lane 4, supernatant (51); Lane 5, heat-treated S1—insoluble pellet (P2); Lane 6, heat-treated S1—soluble fraction (S2); Lanes 7-12, purified tAK-fibrin fractions eluted sequentially from Cibacron Blue affinity chromatography.

The samples are then analysed using a standard assay format to identify fractions containing peak adenylate kinase activity. This is confirmed by SDS-PAGE analysis using standard techniques (see FIG. 3). In brief, the assay is carried out using the following protocol:

1. Dilute the purified tAK fusion 1:1000 and 1:10,000 in Mg Ac Buffer. Add 100 μl per well.
2. Treat with Apyrase (50 μl/well at 2.5 units per ml stock concentration; Sigma Grade VI Apyrase from potato) and incubate for 30 minutes at 30° C., with shaking, to remove ATP.
3. Incubate plate at 70° C. for 10 minutes to denature Apyrase.
4. Add 50 μl/well of ADP (275 μM ADP in MgAc buffer) and seal. Incubate at 70° C. for 20 minutes.
5. Remove plate and allow to cool to room temperature for 20 minutes, warm Luciferase/Luciferin (L/L) reagent to room temperature for 20 minutes.
6. Add 200 μl ATP standard to 1 or 2 empty wells per plate.
7. Set up injectors on luminometer and prime them with L/L reagent (ATP reagent, Biotherma). Inject 30 μl L/L reagent/well.
8. Read light generated immediately using luminometer.

Figures 4A, 4B:
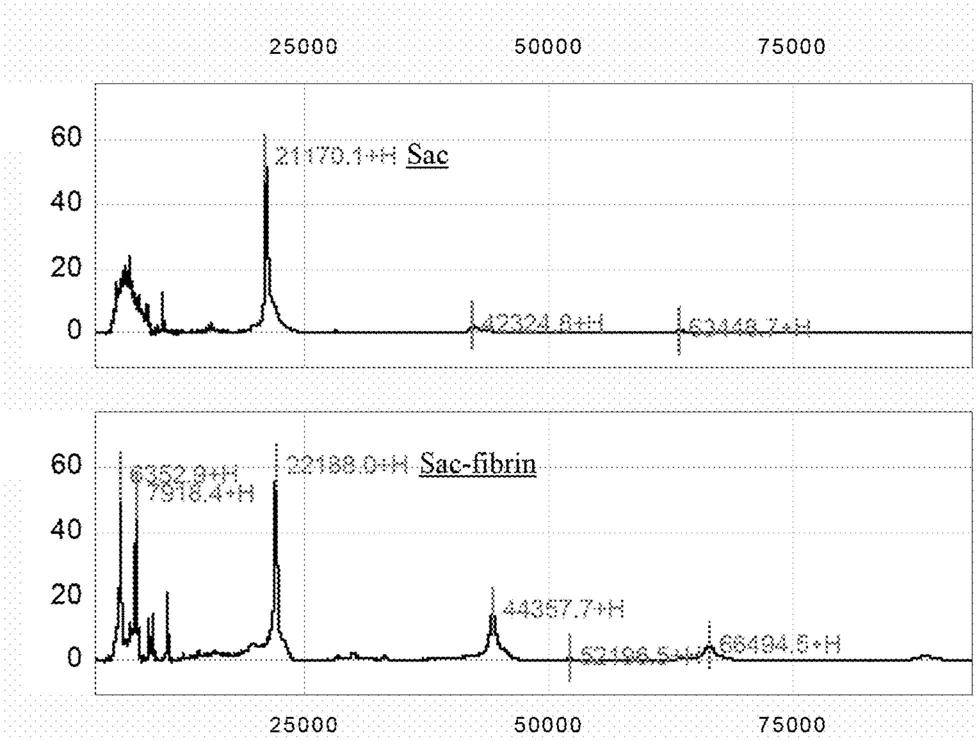
FIGS. 4A and 4B show mass spectroscopy analysis of purified tAK (Sac)-Fibrin peptide fusions and wild type tAK (Sac). Purified Sac (FIG. 4A) and Sac-Fibrin (FIG. 4B) were applied to a silicon coated chip (NP), allowed to dry and matrix applied (Sinipinic acid) for SELDI mass spectroscopy analysis. Molecular weight is shown on the abscissa axis and the relative signal on the ordinate axis. The addition of the fibrin peptide results in an increase in molecular weight of Sac from 21170 Da (FIG. 4A) to 22188 Da (FIG. 4B) with no apparent degradation of said peptide. The respective dimer and trimer Sac species can also be observed at 42324 Da and 63448 Da for Sac, and 44357 Da and 66494 Da for Sac-fibrin.

The fractions with peak kinase activity are then dialysed extensively against phosphate buffered saline (PBS pH 7.4) and stored until required. Confirmation of the presence of the added transglutaminase substrate sequence (i.e. the fibrin peptide) on the purified tAK is confirmed by SELDI mass spectroscopy analysis (see FIGS. 4A and 4B).

Optionally a fusion can be prepared between tAK and the full length fibrinogen molecule to provide further means to incorporate the enzymatic activity within the fibrin film.

Deposition of tAK Fusions onto a Solid Support.

The tAK-fibrin fusion is diluted to around 200 μg/ml in either PBS or bicarbonate buffer (pH 9.6) and applied to a solid support of 316L grade stainless steel, plastic, glass or textiles. The protein is allowed to adhere to the surface for up to 2 hours at room temperature or overnight at 4° C.

Optionally, additional carrier molecules are added at this stage, e.g., sucrose at concentrations up to 1% w/v, albumin at up 1 mg/ml, pig mucin at up to 0.5% w/v. The addition of such carriers may be particularly important for certain types of indicator but the presence of the carrier should not interfere with subsequent interaction and cross-linking to the fibrin film applied in the next stage.

Overlay of Fibrin-Containing Soil and Cross-Linking to Fibrin-tAK Fusion.

A test soil (biological matrix) is then overlaid onto the tAK-fibrin fusion preparation adhered onto the surface as described above.

A solution containing fibrinogen is added to effect the cross-linking of the indicator to the fibrin-containing test soil.

A solution containing up to 3 mg/ml fibrinogen (containing Factor XIII), 2.5 mM $CaCl_2$, and thrombin (up to 5 NIH units per ml) is mixed freshly and added to the coated surface of the solid support. The reaction is allowed to proceed at room temperature for up to 30 minutes, depending on the level of cross-linking required. Optionally, albumin (up to 80 mg/ml) and haemoglobin (up to 80 mg/ml) are added at this stage to provide a tougher and more realistic challenge for cleaning of a blood-like soil. After cross-linking, residual liquid is removed, and the indicator device is left to dry.

FIG. 9 shows SDS-PAGE analysis of the covalent attachment of a tAK-fibrin fusion protein with fibrinogen to form a tAK-fibrin film.

Optionally, the tAK-fibrin peptide fusion is added to the fibrin-containing test soil solution (biological matrix) prior its addition to the solid support surface. Cross-linking of the fibrin peptide to the matrix can be increased by adding more Factor XIII and/or extending the duration of the reaction. Cross-linking can also be enhanced by the use of the tAK fusion protein with fibrin peptides added to both ends of the molecule.

Optionally a fibrinogen-tAK fusion could be added directly to this solution to provide further cross linkage of the indicator.

Covalent Chemical Cross-Linking of tAK to Fibrin or Fibrinogen.

The preparation of tAK-fibrin as a fusion protein has already been described above. However, tAK-fibrin may also be prepared by chemically joining tAK to fibrin, fibrin peptides or fibrinogen by a wide range of methods familiar to those working in the field. For example purified protein preparations for fibrinogen or fibrin are obtained from commercial sources (e.g., Sigma). The tAK from *S. acidocaldarius* is prepared as described above. The tAK is derivatised using the amide reactive reagent SPDP (SPDP (N-Succinimidyl 3-(2-pyridyldithio)-propionate; Pierce chemical company) according to the maufacturer's instructions. The fibrin or fibrinogen is also derivatised using the same protocol. The derivatised tAK is reduced by reaction with mercaptoethanol to yield a reactive sulfhydryl group.

This is then mixed with the SPDP-derivatised fibrin causing the formation of covalent bonds between the two molecules. The concentrations of the reaction partners should be determined empirically following the guidelines within the manufacturer's instructions for SPDP.

The chemically linked tAK-fibrin or fibrinogen can be used interchangeably or in addition to the fusion protein throughout the preceding description of this and subsequent examples.

EXAMPLE 11

Uses of Fibrin-tAK Indicators

Use in a Washer Disinfector.

An indicator is prepared as described in Example 10. The solid support is a rectangular stainless steel strip 55 mm×5 mm×0.75 mm, which may be coated on one or both surfaces. One or several indicator strips are positioned within the chamber of the washer disinfector. Optimally, these may be positioned in sites which may be the most difficult to clean, providing the highest degree of certainty that the wash process has been effective. Alternatively, they may be positioned to monitor the function of multiple spray arms (i.e. where these may be independent of each other). The indicator strips are clipped to the shelves or other substructure of the washer-disinfector chamber to ensure that they do not move during the wash treatment. The orientation of the surrogate devices can be modified to provide further information about the efficacy of the wash process, for example by positioning them so that the coated surface are at right angles to the direction of water spray.

The instrument load is added and the standard run cycle performed. At the end of the run the devices are removed from the chamber and the presence of residual tAK-fusion assessed, as outlined in Example 12, prior to the removal of the instruments and any subsequent processing. Optionally, devices can be removed during the wash process either by interrupting the process at carefully defined points or by using a machine that provides a method of withdrawing the indicator during the run.

Use in Endoscope Test Procedure.

The indicator device for monitoring an endoscope reprocessing system is essentially similar to that outlined above. A similar size indicator surface, representative of either the stainless steel components within an endoscope, the PTFE tubing or other relevant materials is placed within a tubular chamber. This is attached, via suitable screw, push or bayonet fittings to either the front end of the endoscope or the end which makes contact with patient tissues. This is placed within the endoscope reprocessing unit and the ends of the endoscope tubing and indicator device are coupled to the ports in the unit. The process is run as standard and the indicator device removed at the end of the run for analysis, prior to onward processing or the return of the endoscope to use.

EXAMPLE 12

Means of Assessing Cleaning Performance

The indicator device is removed at the end of the test process. The indicator is inserted into a hygiene monitor or luminometer reagent tube and processed according to the manufacturer's instructions, with the indicator device replacing the swab. The hand-held hygiene monitor provides a read-out in relative light units (RLUs) which is directly proportional to the concentration of ATP generated by the tAK-enzyme attached to the biological component. This in turn is directly proportional to the concentration of enzyme over the concentration range typically used for the indicator. The indicator devices are calibrated such that an RLU value below a pre-determined threshold value is indicative of at least a 3-log reduction (or potentially higher depending on the acceptance criteria) in the concentration of the tAK fusion which remains attached to the indicator surface. The batch release of processed instruments is based upon a reduction in the RLU value generated by the residual tAK fusion on the indicator device. This can be identified by either training operatives to return all batches of instruments above the threshold value or by calibrating the hygiene monitor to provide a simple pass or fail read-out based on the RLU value.

The practical process for allowing onward processing of batches of surgical instruments or other processed products is as follows:

1. Insert indicator devices into pre-set positions within the chamber of the washer disinfector. Clip in place.
2. Add instrument load according to standard operating procedure. Close door and press run button
3. During the run, record any process parameters required by the standard operating procedure.
4. At end of the run record the time and any process parameters required by the standard operating procedure.
5. Switch on the hand-held hygiene monitor (SYSTEM-SURE PLUS™; Hygiena) and allow to calibrate.
6. Remove the indicator devices from the chamber and insert them into the reagent tube (ULTRASNAP™; Hygiena).
7. Bend the reagent reservoir from side to side to expel all of the reagent down the sample tube (according to the manufacturer's instructions.
8. Shake the tube for 5 seconds.
9. Insert the tube into the hygiene monitor and record signal immediately.
10. Record the RLU value or Pass/Fail read out on the process run sheet.
11. Repeat steps 6-10 for any further indicator devices.
12. If any fails are observed, re-process the instruments starting at step 1.
13. At the end of each day download the results to a suitable data logger or computer terminal via the port attached.
14. Weekly and monthly check the Pass/Fail rate and record any trends in process fails (day of week, time of day, position within chamber, operator)

This is an example of a suitable protocol, but a number of different reagent tubes or instruments (such as those prepared by BioTrace, Charm or other companies) would be suitable to enable such instrument release protocols.

EXAMPLE 13

Preparation of tAK-Sup35 Fusion.

Clones containing the N-terminal domain of Sup35 from *Saccharomyces cerevisae* fused to either the N- or C-terminus, or both termini, of adenylate kinases from either *S. acidocaldarius* or *T. maraima* are generated by standard DNA manipulation techniques. All clones are transferred as NdeI-SalI fragments into the pMTL1015 expression vector and their sequences verified. The expression constructs are used to transform BL21 or RV308 expression strains and the material grown in large scale fermentation conditions, but with minimal aeration.

Expression and purification of a tAK-Sup35 fusion is essentially the same as for the fibrin-peptide fusions described in Example 10, except that the use of the thermal denaturation step (Step 4) is not part of the purification protocol. In brief, cell paste from the fermenter is resuspended in buffer A, and lysed by sonication. The cell debris is removed (no heat treatment is used standardly for these type of fusions) and the supernatant used for column purification as outlined in Example 10.

Figure 5:
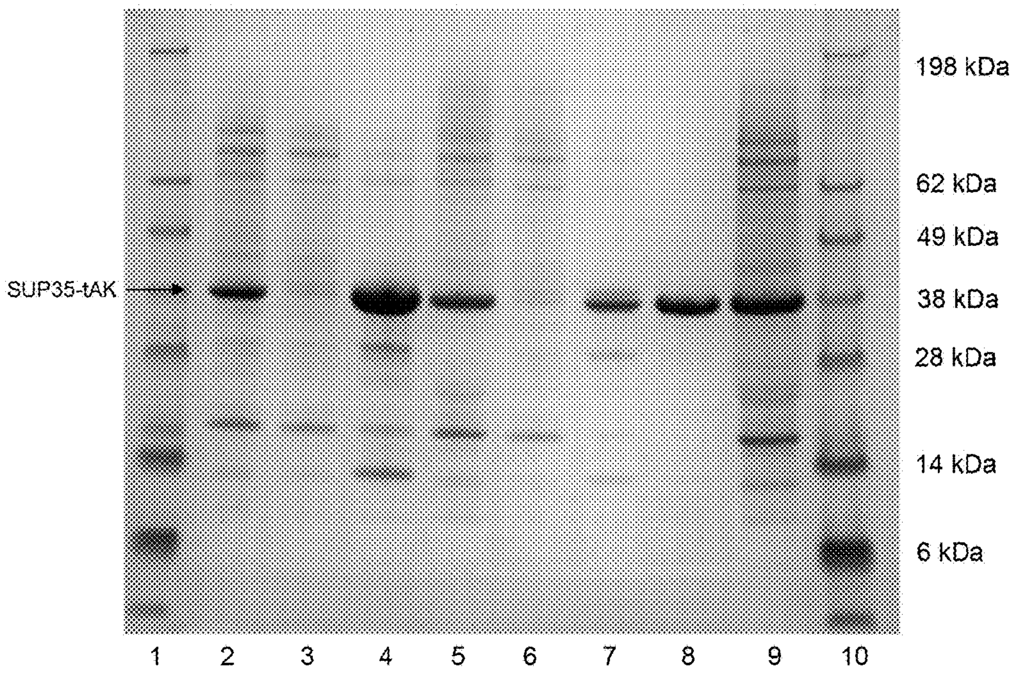
FIG. 5 shows gel electrophoretic analysis (SDS-PAGE) of solubilised and refolded Sup35-tAK (Sac) from clarified inclusion body preparations. Lane 1, SeeBlue Plus 2 marker; Lane 2; Sup t35AK, refolded from solubilised inclusion bodies (prepared in the presence of the reducing agent, DTT) in 20 mM Tris-HCl pH 8.5; Lane 3, as Lane 2 but using solubilised inclusion bodies prepared in the absence of DTT; Lane 4, as Lane 3, insoluble fraction; Lane 5, as Lane 2 but heat-treated at 75° C. for 10 min, soluble fraction; Lane 6, as Lane 3, heat-treated at 75° C. for 10 min, soluble fraction; Lane 7, as Lane 6, insoluble fraction; Lane 8, as Lane 7, washed pellet; Lane 9, as Lane 2 concentrated in dialysis tubing covered in PEG 10000; Lane 10, as Lane 1. *E. coli* RV308 expressing Sup35-tAK cultured at 30° C. in shake flasks to a final $OD_{600\ nm}$ of 14. Centrifuged cell paste was resuspended in 20 mM Tris-HCl, pH 7.5, 10 mM EDTA, 1% Triton X-100 at 0.05× culture volume. Cells were lysed by sonication. Inclusion bodies were isolated from the crude cell lysate by centrifugation and washed three times with 20 mM Tris-HCl, pH 7.5, 10 mM EDTA, 1% Triton X-100. Final wet weight of washed pellet was 5 g/L culture. Inclusion bodies were resuspended at 15 mg/ml in 50 mM CAPS, pH 11 with 0.3% N-lauroylsarcosine and +/−1 mM DTT, incubated for 1.75 hours at 20° C. and clarified by centrifugation at 12,000 rpm in Sorval centrifuge, SS34 rotor for 10 minutes. The supernatant containing the solubilised protein was then dialysed with 5 buffer changes (the first two with DTT and the remainder without) prior to use. Refolded Sup35-tAK could be prepared in soluble or insoluble forms by solubilising the inclusion bodies in the presence or absence of DTT as shown in lanes 2 and 4 respectively. Refolded, soluble, Sup35-tAK demonstrated stability against the above heat treatment.

Under certain growth conditions the fusion proteins may be insoluble, being apparent as inclusion bodies within the cells. In this case the cell pellets are prepared and lysed in the same way, but the resulting insoluble fraction, containing the inclusion bodies, is collected by centrifugation. This material is washed in a buffer (e.g., PBS) containing Triton X100 (up to concentrations of 5%). After each wash the pellet containing the fusion proteins is separated by centrifugation. After 5 washes the inclusion bodies are resolubilised in PBS containing 8M urea and agitated gently for up to 30 minutes. Any residual insoluble material is removed by centrifugation. The urea-solubilised material is dialysed against up to 5×10 volumes of PBS to remove the urea and allow the fusion proteins to refold. Optionally the urea may be removed more rapidly by spraying the urea-solubilised preparation through a fine gauge needle into 100 volumes of rapidly stirred PBS or buffer A as used for purification. The material is allowed to stand at room temperature with stirring for up to 30 minutes prior to subsequent processing. FIG. 5 shows a gel electrophoretic analysis (SDS-PAGE) of solubilised and refolded Sup35-tAK (Sac) from clarified inclusion body preparations.

Subsequent purification of the fusions is carried out essentially as described in Example 10. The supernatant from either lysed cells or solubilised and refolded inclusion bodies is loaded onto a pre-equilibrated Blue Sepharose Fast Flow column. After extensive washing in buffer A and subsequently in wash buffer, the protein is eluted using buffer B. Peak fractions are determined by SDS-PAGE analysis and enzyme assay. Fractions are then pooled and dialysed into PBS.

Conversion of tAK-Sup35 to an Amyloid Form.

The Sup35-tAK fusions when assembled into fibrils are more representative of amyloid proteins such as prions which are key molecules against which to assess the efficacy of decontamination processes.

Figure 6:
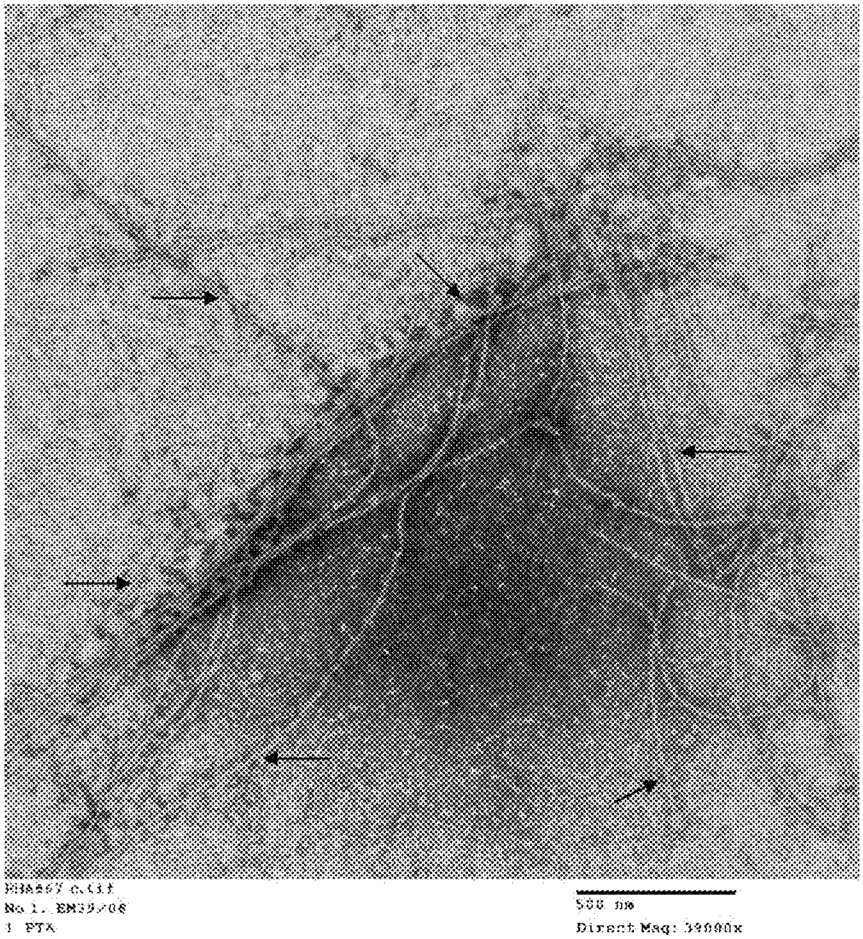
FIG. 6 shows electron microscopy analysis of tAK-Sup35 (Sac) fibril formation. Purified inclusion bodies were solubilised and refolded as described previously (FIG. 5). Fibril formation was induced by incubating at 4° C. for 24-72 hours at a protein concentration of 2 mg/ml. The samples were analysed by standard transmissive electron microscopy (TEM) techniques using uranyl acetate as the negative stain. Multiple polymeric species can be observed across the image (arrowed). No fibril species were observed at protein concentrations below 2 mg/ml.

The amyloid form of the Sup35-tAK fusions is generated by either refolding of the purified soluble protein or by modifying the conditions used for dialysis of the urea-resolubilised inclusion body preparations. In the first case, a conformational change is induced by exposure of the fusion proteins to conditions around pH 4 (e.g by dialysis into a suitably buffered solution at pH 7.4 optionally containing up to 1M NaCl). In the latter case, the resolubilised fusion proteins in 8M urea/PBS are dialysed for 6-12 hours at room temperature against 2M urea, 300 mM NaCl, in PBS (pH 7.4). Alternatively, the fibrilisation can be induced by dialysis against 20 mM Tris pH8.0 10 mM EDTA under similar incubation conditions. Electron microscopy is used to confirm the presence of fibrils (see FIG. 6).

Optionally, the fusion proteins may be incorporated into fibrils containing normal Sup35. This is achieved by mixing the fusions with unfused Sup35 expressed in the same way, at ratios between 1:1 to 1:10 fusion:Sup35.

Deposition of tAK-Sup35 Fusions onto Solid Support.

Deposition of the fibrils onto a solid support is effected by simple protein adsorption in a suitable buffer (e.g., PBS pH 7.4 Bicarbonate buffer pH 9.6) in the presence of high levels of NaCl. The use of charged or precoated surfaces (e.g., plastics coated with Poly-L-lysine) is useful in providing surfaces which can more effectively bind the fusion proteins.

Optionally, the fibrils may be deposited in a suitable carrier, such as sucrose (to 1%), pig mucin (up to 0.5%), or albumin (up to 1 mg/ml).

Overlay of Test Soil

A test soil (biological matrix) is then overlaid onto the amyloid preparation adhered onto the surface as described above.

Suitable biological matrices in which the amyloid indicator is embedded include e.g., 0.5% mucin, with or without albumin, a commercial test soil (such as that manufactured by Browne's) or any one of the test soils identified in guidance documents issues by national and international standards committees (e.g., Edinburgh soil as detailed in HTM 01/01 (UK).

Assembly of Amyloid Fibrils within the Test Soil

Given the ability of amyloids to self-assemble in complex matrices it is possible for the amyloid-tAK fusion to be mixed with soil components prior to fibril formation and subsequent deposit onto surfaces. This provides further options for indicators in which the amyloid fibrils may be mixed and inter-chelated with other soil components providing a different type of matrix that may be harder to remove from surfaces.

EXAMPLE 14

Uses of tAK-Sup35 Indicator

Use of tAK-Sup35 Indicator for Assessing Prion Removal from Surfaces in a Washing Process.

An indicator as described in Example 13 is prepared as fibrils and dried down onto a steel surface in the presence of 0.5% mucin. The indicator is placed within the chamber of a washer disinfector at pre-determined locations. The instrument load is added. The process is started as per the manufacturer's instructions and any process records completed. At the end of the process, and before any instruments are taken from the machine, the indicator devices are removed and assessed as described in Example 12.

Use of tAK-Sup35 Indicator for Assessing Prion Inactivation in a Protease-Based Process.

Indicators as described in Example 13 are prepared as fibrils with a high ratio of free Sup35:Sup35-tAK (in excess of 5:1) and deposited onto solid support strips in the presence of Edinburgh soil. The indicator devices are inserted into a pre-soak bath containing freshly made PRIONZYME™ (Genencor International) prion inactivation treatment (at 60° C., pH 12). The indicator strips are clipped to the side of the bath such that the ends of the indicators are within the bulk of the liquid. Instruments are added as required and processed for 30 minutes. The indicator devices are removed from the bath at the end of the process, prior to removal of the instruments and assessed as described in Example 12.

Use of tAK-Sup35 Indicator for an Oxidative Process Aimed at Destroying Prions.

An indicator as described in Example 13 is prepared as fibrils using only Sup35-tAK, and deposited onto a stainless steel surface (optionally in the presence of 0.1% w/v sucrose). The indicator is attached to the inside of the lid of a GENESIS™ container in which the instruments are prepared for processing and the lid closed. The container is inserted into the load chamber of a suitable processor for oxidative challenge (e.g., the 125 L ozone steriliser; $TSO_3$ or a vapour phase hydrogen peroxide technology such as that described in published papers by Fichet et al. 2004; Lancet) and the process run according to manufacturers' instructions. At the end of the process, the GENESIS™ container is taken out of the chamber and the indicator devices are removed and processed as described in Example 12.

EXAMPLE 15

Preparation of a Neurological Soil with tAK-Coupled Components

Identification of Components Essential for a Neurological Test Soil.

The critical target components encountered with neurosurgical processes that may remain attached to surgical instrument surfaces can be determined in experimental studies. Surgical instruments from neurosurgical wards may be treated in routine cleaning processes. Residual protein or other biological molecules can be solubilised from the surface of the instrument using partial acid hydrolysis, strong alkaline cleaners or the use of suitable lytic enzymes (e.g., proteases, nucleases, lipases). The principle molecules can then be determined using mass spectrometry techniques such as Surface-enhanced laser desorption ionisation (SELDI) or equivalents.

The same analysis may be achieved by artificially soiling surgical instruments with human neurological material or equivalent samples from animal species (e.g., rodent brain homogenate).

A representative neurological test soil will require a variety of components that include, inter alia, nerve derived proteins (e.g., neurofilament), lipids or glycolipids representative of neuronal environments (e.g., sialic-rich gangliosides) and carbohydrates. If the test soil is designed to address particular issues regarding specific diseases, such as diseases caused by protein aggregation (e.g., prion disease, Alzheimer's disease) then these components, or surrogates thereof, will also be valuable additions to the test soil.

Cross-Linking of tAK-Fusions to Protein or Glycolipid.

A recombinant tAK fusion can be made to neurofilament proteins or sub-domains thereof by using the methods essentially as described in Examples 10 and 13.

In addition, cross-linking can be achieved without the need to generate recombinant expression clones. This may be particularly useful where heavily glycosylated proteins or glycolipids are linked to the tAK. In this case the protein or glycolipid is purified either from a suitable source or generated by expressing a suitable gene construct in a eukaryotic cell line (e.g., mammalian cell, baculovirus expression system). Purification may be via one of a variety of well known protein purification methods or by detergent solubilisation of membrane lipids. The purified material is then cross-linked to purified tAK using one of a wide range of coupling chemistries (e.g., SPDP (Pierce chemicals) used to link proteins via primary amines on proteins; treatment with meta-periodate used to open up carbohydrate groups allowing cross linking to glycolipids). Further suitable methods for effecting cross-linking of the tAK with carbohydrate or lipid-containing molecules are described in detail in Example 23

Of particular use in this application is the covalent coupling of the tAK to biological components such as gangliosides, including those specific for neuronal cells (e.g., $GT_{1b}$, $GT_{1a}$) and those of general cell origin (e.g., $GM_1$). Gangliosides are purified by standard methods involving detergent solubilisation, phase partitioning and differential centrifugation. Alternatively the indicator can be formulated using commercially available purified gangliosides.

Conjugation of tAK to Nucleic Acid Components of Neurological Test Soil.

The tAK is cross-linked to a suitable nucleic acid, either purified, generated synthetically or amplified from a template using PCR or similar techniques. The cross-linking can be achieved by incorporating a biotin label onto the nucleic acid, e.g., during synthesis and using a tAK-cross-linked to streptavidin.

Deposition of Test Soil Components onto Solid Support.

The deposition of one or more tAK indicators onto a solid support can be achieved as described in Examples 10 & 13. In brief, the tAK complexes are prepared in PBS or bicarbonate buffer (pH 9.6) and allowed to dry on a polycarbonate surface for 30 minutes at room temperature. Optionally, sucrose may be added up to concentrations of 1% w/v. The binding conditions are designed to favour attachment via the biological component rather than the tAK, for example by blocking remaining active groups on the surface of the tAK using a suitable surface modifying agent or by incorporation of high levels of NaCl.

Optionally, the deposited neurological soil may be fixed by treatment with 70% ethanol or isopropanol. To achieve this, the indicator is incubated in 70% isopropanol for 30 minutes at room temperature. This mimics one of the commonly encountered processes which may increase the resistance of contaminating materials on surgical instruments, and therefore provides the indicator with an effective way of monitoring the removal of such materials.

EXAMPLE 16

Preparation of Norovirus Capsid Protein (58 kDa)—tAK Fusions

A gene encoding a 58 kDa capsid protein from norovirus is generated as a synthetic construct. This clone is cloned onto the 5' end of the gene encoding the thermostable adenylate kinase from *Thermotoga maritima* to generate a single fusion protein. After sequence verification this clone is transferred into either a pMTL vector for expression in *E. coli* or into a baculovirus expression system (e.g., BacPAK expression system; Clontech) for expression in insect cell lines such as SF9 cells.

Expression and Purification.

Expression of the capsid protein-thermostable kinase fusions in *E. coli* is carried out essentially as described in the previous examples. The proteins are purified using a similar protocol on Blue Sepharose Fast Flow with no thermal denaturation step applied during the cell lysis protocol. Purified proteins are analysed by SDS-PAGE analysis and by enzymatic assay as described in the previous examples. The assembly of the fusion proteins into virus-like particles (VLPs) is promoted by altering the pH and salt concentration.

Baculovirus expression and subsequent purification is carried out essentially as described in Jiang et al., (1992) "Expression, self-assembly and antigenicity of the norwalk virus capsid protein", *J Virology*, 66, page 6527-6352.

Deposition on Solid Supports.

The purified VLP-tAKs are deposited onto a solid support suitable for validating clean-down and disinfection of surfaces used in food preparation or following outbreaks of norovirus in hospital settings.

For validating the decontamination of food preparation surfaces, VLP-tAKs are prepared in a PBS buffer containing a crude food extract comprising egg albumin and sucrose. This matrix is coated onto a polyvinyl strip measuring 5 cm×5 cm and allowed to dry for either 2 hours at room temperature or overnight at 4° C.

For assessing the decontamination of a healthcare facility potentially contaminated following an outbreak of norovirus, the VLP-thermostable kinase indicators are made up in a preparation designed to mimic healthcare-related soiling. This included various blood-related proteins as described above, or one of the standard bed-pan soils enshrined in national and international decontamination standards. Particularly efficacious indicators are set up using textile solid supports representative of, for example, hospital curtains or gowns.

Use of Norovirus VLP-tAK Fusions for Validation of Viral Removal Processes.

The norovirus VLP-tAK fusions are particularly advantageous for validating the ability of processes to remove norovirus from water or food samples. They retain the size, charge and hydrophobicity properties of the parent virus and as such will mimic their behaviour in removal processes. This is particularly useful in this case as no culture method exists for norovirus and as such it is currently not possible to measure live virus clearance other than by RT-PCR, a potentially time consuming method.

For example, the norovirus VLP-tAK fusions are put into a water source and filtered through a process designed to remove viral particles. Sufficient viruses are input to measure the required level of viral clearance. The numbers of VLPs post filtration are measured and assessed against the pre-determined pass/fail criteria.

EXAMPLE 17

Generation of Bacteriophage MS2 Coat Protein—tAK Fusions

The generation of MS2 coat proteins and their spontaneous assembly into virus like particles has been described in a number of studies, for example in Peabody (2003), "A viral platform for chemical modification and multivalent display", *J Nanobiotechnology, vol* 1, page 5.

The protein sequence of MS2 coat protein capable of generating VLP when expressed in *E. coli* is given below (SEQ ID NO:62):

```
MASNFTQFVL VDNGGTGDVT VAPSNFANGV AEWISSNSRS
QAYKVTCSVR QSSAQNRKYT IKVEVPKVAT QTVGGVELPV
AAWRSYLNME LTIPIFATNS DCELIVKAMQ GLLKDGNPIP
SAIAANSGIY
```

Constructs of MS2 coat proteins are generated with the tAK from *Thermatoga maritima*, fused at either the N- or C-terminus of the expressed protein. Depending on the location of the fusion this results in the incorporation of the tAK either within the lumen of the VLP or exposed on the surface. The two locations both have useful properties for their application as indicators. Optionally the MS2 coat protein may be modified by inclusion of a cysteine residue at position 15 in the native sequence (substitution threonine15 to cysteine). The VLP-tAK fusions are purified using a combination of the methods described for tAK fusions above (Examples 10 and 13) with additional ion exchange steps if required. The intact VLPs incorporating the tAK can also be purified on the basis of size exclusion using a Sepharose CL-4B column.

Alternatively, purified tAK can be cross-linked to MS2 VLPs using chemical cross-linking reagents. In brief, tAK from *S. acidocaldarius* is derivatised with SPDP and reduced to yield a reactive sulfhydryl group. This is then mixed with the MS2 VLPs containing the T15C variant of the protein. This effects covalent disulfide bonds between the two partners. These types of covalently linked molecules can be used interchangeably with the genetic fusions throughout the remainder of these examples.

Deposition of MS2 Coat Protein—tAK Fusions on Solid Supports.

The purified tAK-containing MS2-VLPs are deposited on surfaces in a similar way to the fusions described in the previous examples using standard protein adsorption techniques. Optionally, highly charged or hydrophobic surfaces may be used to provide an indication of viral removal from specific surfaces within process regimes.

The VLP-tAK fusion may be deposited alone or may be contained within a suitable soil matrix designed to represent the relevant soiling encountered during the treatment process to be validated. For example, a bed-pan soil may be used for evaluation or validation of the removal of faecal material from either bed-pans, toilets or during diarrhoeal episodes.

Use of MS2-tAK Fusions for Validating a Cleaning Regime.

The MS2-VLP indicator is set up on a ceramic surface as described above. The ceramic indicator is exposed to the same cleaning chemistry as the bathroom surfaces to be cleaned, e.g., to diluted sodium hypochlorite at a dilution of approximately 2.5% (v:v), and under the same conditions (30 minutes at ambient temperature). At the end of the process the ceramic indicator is inserted into a hygiene monitor tube and the residual MS2-tAK measured using the method of Example 12. If cleaned below a pre-set threshold then the cleaning regime is deemed to have been successful. If not then repeat cleaning is required to minimise any risk of disease transmission.

Use of MS2-tAK Fusions for Validating a Viral Removal Process.

As the MS2-tAK VLPs mimic the size, surface charge and hydrophobicity of the parent virus and are capable of representing a wide variety of related viruses (e.g., polio virus), these indicators are extremely useful for validating viral removal processes in either a laboratory or field setting. The rapidity of the tAK assay provides significant advantages over traditional culture-based methods.

For example, a water treatment system may be validated in situ using the MS2-tAK VLPs. Sufficient MS2-tAK VLPs are put into the input water in the treatment plant to provide a sufficient log clearance estimation for the efficacy of the process, as determined by national or local regulations. For example, $10^9$ VLP-tAKs per liter are put into the input water. The process is performed and approximately 1 ml samples of the post-process water is tested in a suitable hygiene monitor tube system (e.g., AQUA-TRACE™, Biotrace UK). A value indicating less than 1 VLP-tAK per ml of water would be sufficient to demonstrate a 6-log clearance of viruses by the process employed. This could be done within 2 minutes of the process being completed rather than 16-24 hours that would be required for a standard culture-based method in *E. coli.*

Such methods are relevant for validating a wide range of viral inactivation processes used widely in the healthcare, food, water or pharmaceutical industries. In the vast majority of cases it can replace the use of the parent MS2 bacteriophage, used widely to validate viral-removal processes, providing far more rapid and sensitive determination of removal. For example, water purification through ceramic microfilters (replacing the parent bacteriophage in Wegmann et al., 2007, "Modification of ceramic microfilters with colloidal zirconia to promote the adsorption of viruses from water"), treatment of water with gaseous chlorine (Clevenger et al., 2007, "Comparison of the inactivation of *Bacillus subtilis* spores and MS2 bacteriophage by MIOX, ClorTec and hypochlorite", *J Applied Microbiology,* 103, p 2285-2290), validation of virucidal efficacy of hand washing (Jones et al., 1991, "The use of bacteriophage MS2 as a model system to evaluate virucidal hand disinfectants", *J Hospital Infection,* 17, p 279-285). Other examples would be to validate, in process, the removal of virus particles from fractionated blood, cellular extract of human or animal origin, pharmaceutical products, food preparation (e.g., shell-fish extracts).

EXAMPLE 18

Preparation of Further Kinase-VLP Fusions Suitable for Evaluating and Validating Viral Removal or Destruction The table below lists a series of VLP fusion proteins that are valuable in the development of indicators for assessing removal or inactivation of a range of viral pathogens. These represent either actual pathogens where the validation of removal may be essential, or model viruses capable of representing the removal of a range of related pathogens. The pathogens are from both the medical and veterinary field, and also encompass a range of known or possible zoonotic pathogens which may transmit from animals to humans.

TABLE 2

Suitable biological components for preparing kinase-VLP fusions for evaluating and validating viral removal or destruction

| Virus | Recombinant fragment | Expression system | Reference |
|---|---|---|---|
| Bacteriophage, e.g., MS2, PP7 | MS2 coat protein PP7 coat protein | *E. coli* (pET3d expression vector) | Peabody et al., 2003, *Journal of Nanobiotechnology*, 1, p5 |
| Norwalk (norovirus) | Capsid | Baculovirus | Reviewed in Grgacic and Anderson, 2006, *Methods*, 40, p60-65 |
| Rotavirus | VP2, VP6 and VP7 | Baculovirus | Reviewed in Grgacic and Anderson, 2006 |
| SARS (coronavirus) | S, E and M | Baculovirus | Reviewed in Grgacic and Anderson, 2006 |
| Bluetongue | VP2 | Baculovirus | Roy et al., 1994, *Vaccine*, 12, p805-811 |
| Human papillomavirus | viral major structural protein, L1 | 293TT cells | Buck et al., 2005, J Virology, 79, p2839; Buck et al., 2004, J. Virology, 78, p751 |
| Hepatitis B | Small envelope protein (HBsAg) | Yeast or mammalian cells | Reviewed in Grgacic and Anderson, 2006 |
| Hepatitis C | Core, E1 and E2 | Baculovirus, yeast and mammalian cells | Reviewed in Grgacic and Anderson, 2006 |
| Influenza; both human strains (e.g., H5N1) and avian influenza strains. | Haemagglutinin, neuraminidase and matrix (M1 optional) | Baculovirus, mammalian cells | Reviewed in Grgacic and Anderson, 2006 |
| Poliovirus | Capsid (VP0,1 and 3) | Baculovirus | Reviewed in Grgacic and Anderson, 2006 |
| HIV | Pr55gag, envelope | Baculovirus, yeast and mammalian cells | Reviewed in Grgacic and Anderson |
| Dengue B | Envelope (e) and premembrane/membrane (prM/M) | Mammalian cells | Purdy and Chang, 2005, *Virology*, 333, p239-250 |

The protein sequence of bacteriophage PP7 coat protein monomer and dimer (Caldeira and Peabody, 2007, Journal of Nanobiotechnology, 5, p 10) is given below. Thermostable kinase genes may be fused to the C-terminus of either the monomer or dimer.

```
PP7 monomer
                                          (SEQ ID NO: 63)
SKTIVLSVGEATRTLTEIQSTADRQIFEEKVGPLVGRLRLTASLRQNGA

KTAYRVNLKLDQADVVDCSTSVCGELPKVRYTQVWSHDVTIVANSTEAS

RKSLYDLTKSLVVQATSEDLVVNLVPLGR

PP7 dimer
                                          (SEQ ID NO: 64)
MSKTIVLSVGEATRTLTEIQSTADRQIFEEKVGPLVGRLRLTASLRQNG

AKTAYRVNLKLDQADVVDSGLPKVRYTQVWSHDVTIVANSTEASRKSLY

DLTKSLVATSQVEDLVVNLVPLGRYGSKTIVLSVGEATRTLTEIQSTAD

RQIFEEKVGPLVGRLRLTASLRQNGAKTAYRVNLKLDQADVVDSGLPKV

RYTQVWSHDVTIVANSTEASRKSLYDLTKSLVATSQVEDLVVNLVPLGR
```

EXAMPLE 19

Expression of Kinase—Bacterial Fimbriae Fusions for Use in Development of Indicators to Assess Biofilm Removal from Surfaces A fusion between the tAK from *Thermotoga maritima* and the CsgA protein from *E. coli* is generated by standard recombinant cloning familiar to those with knowledge of the art. The protein sequence generated is shown below.

Sequence of *E. coli* CsgA protein (SEQ ID NO: 65)

*MKLLKVAAIAAIVFSGSALAGVVPQYGGGGNHGGGGNNSGPNSELNIYQY*

*GGGNSALALQTDARNSDLTITQHGGGNGADVGQGSDDSSIDLTQRGFGNS*

*ATLDQWNGKNSEMTVKQFGGGNGAAVDQTASNSSVNVTQVGFGNNATAHQ*

*Y*

Sequence of adenylate kinase from *Thermotoga maritima* fused to the N- terminus of the CsgA protein (SEQ ID NO: 67)

MMAYLVFLGPPGAGKGTYAKRIQEKTGIPHISTGDIFRDIVKKENDELGK

KIKEIMEKGELVPDELVNEVVKRRLSEKDCEKGFILDGYPRTVAQAEFLD

SFLESQNKQLTAAVLFDVPEDVVVQRLTSRRICPKCGRIYNMISLPPKED

ELCDDCKVKLVQRDDDKEETVRHRYKVYLEKTQPVIDYYGKKGILKRVDG

TIGIDNVVAEVLKIIGWSDKGSGVVPQYGGGGNHGGGGNNSGPNSELNIY

QYGGGNSALALQTDARNSDLTITQHGGGNGADVGQGSDDSSIDLTQRGFG

NSATLDQWNGKNSEMTVKQFGGGNGAAVDQTASNSSVNVTQVGFGNNATA

HQY

For expression the clone is transferred to a suitable expression vector such as pET 32a (Novagen) or pMAL-C2x (New England Biolabs) and the protein expressed in a suitable host strain (e.g., BL21) under normal growth conditions.

Depending on the growth conditions the thermostable kinase-CsgA fusion may be expressed either solubly within the cytoplasm of the cells or as an insoluble inclusion body within the cell. In the former case purification is carried out as described in Examples 10 and 13. In the latter, inclusion bodies are isolated by centrifugation following cell lysis and washed extensively in buffer containing 1% Triton X100. Inclusion bodies are solubilised by suspension in 8M Urea or 6 M guanidine hydrochloride and then refolded by rapid dialysis in very low salt buffer (typically less than 20 mM NaCl).

The generation of self assembled layers is mediated by incubating the purified and enzymatically active fusion protein with a hydrophobic surface (e.g., Teflon) in 10 mM Tris pH8. For hydrophilic surfaces such as stainless steel or glass the fusion is incubated in 50 mM Sodium acetate buffer pH4, optionally in the presence of 0.1& Tween 20. Elevated temperatures up to 80° C. may be used to enhance binding or to ensure uniform coverage of surfaces.

Fusions with the equivalent protein sequences from other Gram-positive of Gram-negative organisms (e.g., AgfA from *Salmonella* species) can also be used.

Protein sequence of *Salmonella* AgfA protein (SEQ ID NO: 66)

*MKLLKVAAFAAIVVSGSALAGVVPQWGGGGNHNGGGNSSGPDSTLSIYQY*

*GSANAALALQSDARKSETTITQSGYGNGADVGQGADNSTIELTQNGFRNN*

*ATIDQWNAKNSDITVGQYGGNNAALVNQTASDSSVMVRQVGFGNNATANQ*

*Y*

EXAMPLE 20

Further Self-Assembling Peptides and Proteins for Generation of Biofilms

The generation of further indicator devices containing tAK fusions with peptides capable of self-assembling into fibrils, or surface reactive biofilms is also provided. A list of suitable fusion partners is shown in the table below.

TABLE 3

Suitable self-aggregating/assembling peptides and proteins for generation of biofilms

| Self aggregating proteins and peptides | Recombinant protein | Expression system | Reference |
|---|---|---|---|
| Sup 35 | Sup 35 N-terminal domain or Sup35 peptide | *E. coli*, yeast | Reviewed in Harrison et al., 2007, *Rev Physiol Biochem Pharmacol*, 159, p1-77 |
| Het S, Ure2, Rnq1, New 1 | Native sequence or fragments thereof | *E. coli*, yeast | Reviewed in Harrison et al., 2007; Derkatch et al., 2007, *Proc Natl Acad Sci USA*, 101, p12934-12939 |
| Beta amyloid (Alzheimer's disease) | Aβ 1-32 | *E. coli*, yeast; synthetic peptide | Reviewed in Harrison et al., 2007 |
| Barnacle cement proteins | e.g 19 kDa protein from *B. albicostatus*; 20 kDa protein from *Megabalanus rosa*; novel calcite dependent protein from *B. albicostatus* | *E. coli*, yeast or baculovirus | Urushida et al., 2007, *FEBS J.*, 274, p4336-4346; Nakano et al., 2007, *Biomacromolecules*, 8, p1830-1835; Kamino, 2001, *Biochem J.*, 356, p503-5077. |

TABLE 3-continued

Suitable self-aggregating/assembling peptides and proteins for generation of biofilms

| Self aggregating proteins and peptides | Recombinant protein | Expression system | Reference |
|---|---|---|---|
| Apolipoprotein A1 as an e.g., of apolipoprotein disorders | Residues 1-93 of ApoAI | *E. coli*, yeast, mammalian cells | Andreola et al., 2003, J *Biol Chem*, 278, p2444 |
| Tau (associated with alzheimer's disease) | Proteins or peptides containing residues 306-311 (VQIVYK) | *E. coli*, yeast or mammalian cells | Reviewed in Harrison et al., 2007 |
| Polyadenine binding protein 2 | Peptides containing residues 2-11 (AAAAAAAAAA) | *E. coli*, yeast or mammalian cells | Reviewed in Harrison et al., 2007 |
| Lung surfactant protein C | Peptides containing residues 9-22 (VVVVVVVLVV VVIV) | *E. coli*, yeast or mammalian cells | Reviewed in Harrison et al., 2007 |
| CgsA subunit (adhesion to surfaces and biofilm formation in *E. coli*) | Native sequence CsgA catalysed by CsGB sequence | *E. coli* | Gebbink et al., 2005, *Nat Rev Microbiol*, 3, p333; Hammer et al., 2007 |
| AgfA ((adhesion to surfaces, cell-cell interactions and biofilm formation in *Salmonella* spp) | Native sequence | *E. coli* | Reviewed in Harrison et al., 2007, Rev *Physiol Biochem Pharmacol*, 159, p1-77 |
| Amyloid forming cell surface adhesins from floc forming and filamentous bacteria in activated sludge | Various native sequences | *E. coli* | Described in Larsen et al., 2008, *Appl Env Microbiol.* On line citation (*Appl. Environ. Microbiol.* doi: 10.1128/AEM.0227 4-07v1) |
| Herpes simplex virus glycoprotein B (gB) | Peptides containing amino acids 22-42 | *E. coli* or mammalian cells | Cribbs et al., 2000, Biochemistry, 39, p5988-5994 |
| Hydrophobins (from various fungal species e.g., SC3 from *Schizophyllum commune*, RodA/B from *Aspergillus fumigatus*) | Native sequences or derivative peptides containing the core 8-cysteine domain of the hydrophobin. | *E. coli*, yeast or *Pichia pastoris* | Gebbink et al., 2005; Sunde et al., 2007, *Micron* e-pub |
| Chaplins/Rodlins (*Streptomyces* spp) | Chaplin proteins ChpA,B,C,D,E,F,G,H Rodlin proteins RdlA and RdlB and combinations thereof | *E. coli*, yeast or *pichia pastoris* | Gebbink et al., 2005 |
| Gram positive spore coat proteins (e.g similar in sequence or overall structure to those forming ribbon-appendages in *Clostridium taeniosporum*) | P29a, P29b, GP85, and a SpoVM analogue | *E. coli*, *Clostridia* | Walker et al., 2007, *Mol Micro.*, 63, p629-643 |

EXAMPLE 21

Indicators for Monitoring Efficacy of Contact Lens Cleaning for Removal of Biofilms A range of bacteria and viruses pose a potential risk to contact lens wearers both in planktonic and biofilm forms. Indicator devices can be advantageously generated to monitor the effectiveness of cleaning methods for the removal of such organisms.

The fimbriae fusions described above have can provide an indication of the removal of Gram-negative pathogens. Any member of the hydrophobin gene family is a suitable indicator fusion for the removal of fungal pathogens where these highly conserved molecules are the principle mediators of attachment. Hydrophobin genes, or equivalents from *Fusarium* species and *Candida albicans*, are suitable as these organisms represent one of the greatest threats for eye infection leading to ulceration and long term damage.

Fusion proteins can be generated with any of these molecules and formulated within suitable films as described in the previous examples. These indicators can be incorporated as part of the wash chamber, in which the re-useable contact lens is to be cleaned. The process is performed for the appropriate length of time and the lens removed. The indicator is removed and the presence of active fusion protein assessed using a hygiene monitor in the usual way. If below the pre-set thresholds the contact lens is suitable for re-use. If above ("failed" then the contact lens must be re-processed or destroyed.

Protein sequence of the hydrophobin 3 protein from *Fusarium* species (SEQ ID NO: 68)

MQFSTLTTVFALVAAAVAAPHGSSGGNNPVCSAQNNQVCCNGLLSCAVQV

LGSNCNGNAYCCNTEAPTGTLINVALLNCV KLL

Protein sequence of the hydrophobin 5 protein from *Fusarium* species (SEQ ID NO: 69)

MKFSLAAVALLGAVVSALPANEKRQAYIPCSGLYGTSQCCATDVLGVADL

DCGNPPSSPTDADNFSAVCAEIGQRARCCVLPILDQGILCNTPTGVQD

EXAMPLE 22

Generation of tAK Fusions to Cement-Like Proteins for Use in Determining Biofilm Removal tAK from *Thermotoga maritima* is fused to the 19 KDa protein from *Balanus albicostatus* and expressed as described above. Purification is effected from either the soluble or insoluble fraction. Refolding and subsequent deposition of the tAK-containing film onto a solid support is achieved as in Example 19. The thickness, rate of deposition and subsequent removal of the biofilm can be altered by modifying both the salt concentration and pH and by altering the concentration of the fusion protein.

Protein sequences of barnacle cement-like proteins suitable for use in the invention are described below. The thermostable kinase may be fused to either the N-terminus or C-terminus of the cement proteins.

Protein sequence of cement-like protein from *Balanus albicostatus* (19k)

(SEQ ID NO: 70)

VPPPCDLSIKSKLKQVGATAGNAAVTTTGTTSGSGVVKCVVRTPTSVEKKAAVGNT

GLSAVSASAANGFFKNLGKATTEVKTTKDGTKVKTKTAGKGKTGGTATTIQIADAN

GGVSEKSLKLDLLTDGLKFVKVTEKKQGTATSSSGHKASGVGHSVFKVLNEAETEL

ELKGL

Protein sequence of cement-like protein from *Megabalanus rosa* (20k)

(SEQ ID NO: 71)

MKWFLFLLTTAVLAAVVSAHEEDGVCNSNAPCYHCDANGENCSCNCELFDCEAKK

PDGSYAHPCRRCDANNICKCSCTAIPCNEDHPCHHCHEEDDGDTHCHCSCEHSHDH

HDDDTHGECTKKAPCWRCEYNADLKHDVCGCECSKLPCNDEHPCYRKEGGVVSCD

CKTITCNEDHPCYHSYEEDGVTKSDCDCEHSPGPSE

Protein sequence of fusion of the barnacle protein from *Balanus albicostatus* with the tAK from *Thermotoga maritima*; N-terminal fusion (SEQ ID NO: 72)

MRVLVINSGSSSIKYQLIEMEGEKVLCKGIAERIGIEGSRLVHRVGDEKHVIERELPDH

EEALKLILNTLVDEKLGVIKDLKEIDAVGHRVVHGGERFKESVLVDEEVLKAIEEVSP

LAPLHNPANLMGIKAAMKLLPGVPNVAVFDTAFHQTIPQKAYLYAIPYEYYEKYKIR

RYGFHGTSHRYVSKRAAEILGKKLEELKIITCHIGNGASVAAVKYGKCVDTSMGFTP

LEGLVMGTRSGDLDPAIPFFIMEKEGISPQEMYDILNKKSGVYGLSKGFSSDMRDIEE

AALKGDEWCKLVLEIYDYRIAKYIGAYAAAMNGVDAIVFTAGVGENSPITREDVCS

YLEFLGVKLDKQKNEETIRGKEGIISTPDSRVKVLVVPTNEELMIARDTKEIVEKIGRV

PPPCDLSIKSKLKQVGATAGNAAVTTTGTTSGSGVVKCVVRTPTSVEKKAAVGNTG

LSAVSASAANGFFKNLGKATTEVKTTKDGTKVKTKTAGKGKTGGTATTIQIADANG

GVSEKSLKLDLLTDGLKFVKVTEKKQGTATSSSGHKASGVGHSVFKVLNEAETELEL

KGL

-continued

Protein sequence of fusion of the barnacle protein from *Balanus albicostatus* with the tAK from *Thermotoga maritima*; C-terminal fusion
(SEQ ID NO: 73)

VPPPCDLSIKSKLKQVGATAGNAAVTTTGTTSGSGVVKCVVRTPTSVEKKAAVGNT

GLSVSASAANGFFKNLGKATTEVKTTKDGTKVKTKTAGKGKTGGTATTIQIADAN

GGVSEKSLKLDLLTDGLKFVKVTEKKQGTATSSSGHKASGVGHSVFKVLEAETELEL

KGLMRVLVINSGSSSIKYQLIEMEGEKVLCKGIAERIGIEGSRLVHRVGDEKHVIEREL

PDHEEALKLILNTLVDEKLGVIKDLKEIDAVGHRVVHGGERFKESVLVDEEVLKAIEE

VSPLAPLHNPANLMGIKAAMKLLPGVPNVAVFDTAFHQTIPQKAYLYAIPYEYYEKY

KIRRYGFHGTSHRYVSKRAAEILGKKLEELKIITCHIGNGASVAAVKYGKCVDTSMG

FTPLEGLVMGTRSGDLDPAIPFFIMEKEGISPQEMYDILNKKSGVYGLSKGFSSDMRD

IEEAALKGDEWCKLVLEIYDYRIAKYIGAYAAAMNGVDAIVFTAGVGENSPITREDV

CSYLEFLGVKLDKQKNEETIRGKEGIISTPDSRVKVLVVPTNEELMIARDTKEIVEKIGR

Protein sequence of a novel barnacle cement proteins for use in the generation of thermostable kinase fusion proteins. The calcite dependent aggregation and adherence of this protein enable this type of indicator to monitor processes capable of removing mineral ions from aggregates in such a way as to destabilize and remove biofouling or biofilms. The thermostable kinase may optionally be fused to the N-terminus or C-terminus. Sequence from Mori et al., 2007, Calcite-specific coupling protein in barnacle underwater cement; *FEBS J*, 274, p 6436-6446. Protein sequence of

*Balanus albicostatus* calcite-specific adsorbent
(SEQ ID NO: 74)

MKYTLALLFLTAIIATFVAAHKHHDHGKSCSKSHPCYHCHTDCECNHHHD

DCNRSHRCWHKVHGVVSGNCNCNLLTPCNQKHPCWRRHGKKHGLHRKFHG

NACNCDRLVCNAKHPCWHKHCDCFC

Peptide sequence of a peptide derived from a barnacle cement protein for use in the formation of thermostable kinase-containing peptide biofilm preparations. Sequences derived from Nakano et al., 2007, "Self assembling peptide inspired by a barnacle underwater adhesive protein"; *Biomacromolecules*, vol 8, p 1830-1835.

Peptide 1
(SEQ ID NO: 75)
SKLPCNDEHPCYRKEGGVVSCDCK

Peptide 2
(SEQ ID NO: 76)
SKLPSNDEHPSYRKEGGVVSSDSK

Peptide 3
(SEQ ID NO: 77)
KTITCNEDHPCYHSYEEDGVTKSDCDCE

Use of the Cement—tAK Fusion for Monitoring Cleaning of Medical Devices

The indicator described above is deposited onto stainless steel of a grade representative of surgical instruments using the deposition methods described in the previous examples. The device is inserted into a standard instrument load and the process performed as standard. The device is removed at the end of the process and the residual activity of the tAK fusion is correlated with removal of potentially infectious soil components.

Use of the Cement—tAK Fusion for Monitoring Removal of Biofouling.

The indicator described above can also be used to monitor the removal of biofouling in other contexts. For example the indicator may be attached to the bottom of a boat being subjected to cleaning for removal of barnacles and other marine biofilms. The indicator is subjected to the same process and assessed at the end of the procedure. Whilst visual removal of material is the key means of determining performance, the use of a more sensitive assay method allows an assessment of the removal of microscopic amounts of soiling which would provide a better primer for the re-establishment of the marine biofilm. Hence in this application the indicator provides both a demonstration of immediate efficacy and an indication of the longevity of the treatment.

EXAMPLE 23

Cross Linking of tAK to *E. coli* or *Staphylococcus aureus* Exopolysaccaride

The exopolysaccharide is generated by growing the relevant bacterial strain under standard growth conditions in either liquid, semi-liquid, biofilm or solid cultures familiar to those with knowledge of the art. Bacteria, typically towards the end of the logarithmic phase of growth are collected by resuspension (where required) and centrifugation. The cells are washed in low osmotic strength buffers (typically below 100 mM NaCl/$NaPO_4$) usually at near neutral pH. The washing may be carried out by mixing vigorously for 1 hour at room temperature or overnight with gentle agitation at 4° C. Optionally an acidic preparation may be extracted using an acetate buffer at pH between 3 and 5. Limited cell perturbation may be achieved using very low energy sonication or by the addition of low levels of detergent. Preparations may be filter sterilised through a 0.2 μm nitrocellulose or cellulose acetate filter prior to storage at 4° C. or −20° C.

Cross-linking of the polysaccharides to tAKs can be achieved using a variety of coupling chemistries. In the first example the tAK from *Sacidocaldarius* is used. The coupling uses the heterobifunctional reagent ABH (p-Azidobenzoyl hydrazide; Pierce Chemical company product number 21510). The protocol is as follows.

1. Prepare a 20 mM periodate solution by dissolving 4.3 mg sodium metaperiodate in 1 ml 0.1M sodium acetate pH 5.5. Store on ice in the dark.
2. Add 1 ml of metaperiodate solution to 1 ml of the exopolysaccharide (EPS; or other glycoprotein, complex carbohydrate or lipid solution) at a concentration of at least 1 mg/ml carbohydrate. Incubate for 30 minutes at 4° C.
3. Dialyse overnight against phosphate buffered saline.
4. Prepare ABH by dissolving 1.8 mg in DMSO.
5. Add between 10 and 100 µl of the ABH to the oxidised EPS solution generated in step 3 and incubate at room temperature for 2 hours.
6. Dialyse samples overnight to remove excess ABH.
7. Mix the ABH-derivatised EPS with purified tAK from *S. acidolcaldarius* prepared as described previously. The concentration of the tAK required to give the appropriate level of cross-linking may be determined empirically but will typically be in the range of 1-5 mg/ml. Incubate at room temperature for 30 minutes.
8. Expose the reaction mixture to UV light using a UV cross-linking apparatus or equivalent.

In a second example of the chemistries available the heterobifunctional agent MPBH (4-[4-N-maleimidiophenyl] butyric acid hydrazide hydrochloride; Pierce Chemical company product 22305)) is used. The brief protocol is as follows:

1. tAK (e.g., from *S. acidocladarius*) with a reactive sulfhydryl is generated as described above by derivitisation with SPDP (Example 10) and subsequent reduction. Alternatively, tAK's with free cysteine residues (such as the tAK from *Archaeoglobus fulgidus* expressed in a recombinant form as described above) or with additional cysteine residues introduced by standard recombinant methods may be used. Protein is prepared at approximately 1-5 mg/ml 0.1M sodium phosphate 0.15M NaCl pH 7.2 or phosphate buffered saline.
2. Dissolve 3.5 mg MPBH in 1 ml of either dimethylformamide or dimethylsulfoxide to yield a 10 mM solution.
3. Add to the protein from step 1 to achieve a 5-10 fold molar excess of MPBH to protein and react for 2 hours at room temperature (or 4 hours at 4° C.).
4. Dialyse against 0.1M sodium phosphate 0.15M NaCl pH 7.2.
5. Prepare a 20 mM periodate solution by dissolving 4.3 mg sodium metaperiodate in 1 ml 0.1M sodium acetate pH5.5. Store on ice in the dark.
6. Add the 1 ml of metaperiodate solution to 1 ml of the exopolysaccharide (EPS; or other glycoprotein, complex carbohydrate or lipid solution) at a concentration of at least 1 mg/ml carbohydrate. Incubate for 30 minutes at 4° C.
7. Dialyse overnight against 0.1M sodium phosphate 0.15M NaCl pH 7.2.
8. Mix the derivatised sulfyhdryl-containing protein from section 4 with the oxidised EPS solution from step 7 and incubate for 2 hours at room temperature. Optionally separate the cross-linked from remaining free components using size exclusion chromatography.

The methods described above are applicable to generating tAK conjugates with a wide range of complex carbohydrates, glycoprotein, glycolipids and other carbohydrate containing polymers including those from mammalian, bacterial, archaeal, plant or fungal origin.

Use of Indicators Based on Exopolysaccharide-tAK Fusions.

The EPS-tAK indicator is prepared in a suitable coating buffer such as phosphate buffered saline (pH 7.0-7.4), sodium bicarbonate (pH 9.0-9.6) or sodium acetate (pH4.0-5.5), optionally containing up to 500 mM NaCl at a relatively high concentration, e.g., 0.1-2.0 mg/ml. The solution is deposited onto a suitable solid support, such as surgical steel, plastics similar to catheters and lines, plastics used commonly in endoscopes. The interaction is allowed to proceed typically for 1-2 hours at room temperature and the coated surface allowed to dry at room temperature overnight prior to storage.

Optionally other biological matrix components may be added either during the coating phase or subsequent to it.

The indicator is included in the process to be monitored, e.g., within a washer disinfector cycle. The device is removed at the end of the process and inserted into hygiene monitor tubes to provide the read-out of the effective destruction and/or removal. The process is deemed effective if the value obtained is below the pre-determined thresholds of the hygiene monitor of luminometer. If successful the batch of instruments or material processed at the same time as the indicator may be used or passed on for subsequent processing. If deemed a fail the material must be reprocessed with a new indicator device.

EXAMPLE 24

Further Examples of Complex Carbohydrates and Glycoconjugate Indicators

A wide range of complex carbohydrate-containing molecules can be incorporated into indicator devices of the invention by covalent attachment to tAKs using methods such as those set out above (Example 23). Some further examples of these are provided in the table below.

TABLE 4

Suitable carbohydrate-containing biological components

| Type of complex carbohydrate | Organisms (various species and strains) | Type of process for indicator applications |
|---|---|---|
| EPS/LPS (sometimes termed endotoxin) | *Legionella*, *E. coli*, *Staphylococcus* species, *Streptococcus* species, *Pseudomonas* species, *Acinetobactor*, *Shigella*, *Campylobacter*, *Bacillus* species, | Cleaning, decontamination, sterilisation, (specific examples; biofilm removal, endotoxin removal or destruction, surgical instrument cleaning, medical product cleaning and decontamination) |
| Lignin | Filamentous fungi | Biofilm removal and destruction. Removal |

TABLE 4-continued

| Suitable carbohydrate-containing biological components | | |
|---|---|---|
| Type of complex carbohydrate | Organisms (various species and strains) | Type of process for indicator applications |
| Cell wall components | *Streptomyces* | Soil sterilisation |
| Eap1p and equivalent cell surface glycoproteins (Li et al., 2007, *Eukaryotic cell*, 6, p931-939) | *Candida albicans* and related fungal organisms | Biofilm removal, infection control decontamination |
| Spore extracts | *Bacillus* species, *Clostridial* species; other spore formers | Product sterilisation, room cleaning and decontamination |
| Mucin preparations | Mammalian species and recombinant cell cultures | Surgical instrument decontamination, decontamination of surgical masks, outbreak control of respiratory virus outbreaks (e.g influenza, RSV) |
| Brain-derived glycolipids | Mammalian species | Evaluating/validating prion removal technologies, decontamination of neurological instruments, samples etc. |
| Invertebrate secretions | Molluscan gels, | Removal of biofouling |
| Plant carbohydrates, gums, resins, oils or lipids | Various plant species | Removal or destruction of contaminating materials on surfaces or in products. |

EXAMPLE 25

Figure 7:
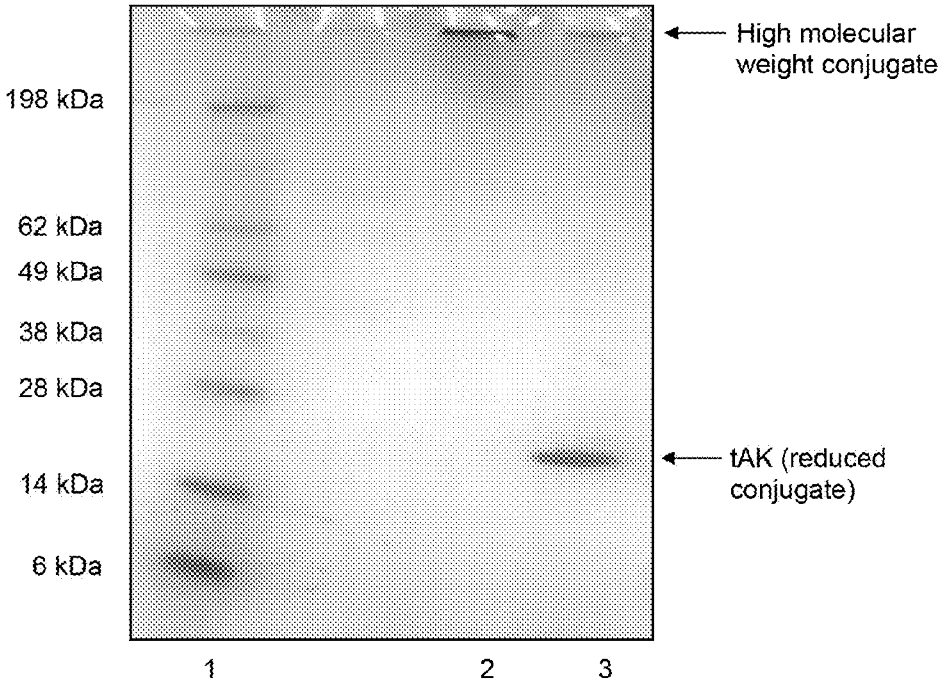
FIG. 7 shows cross-linking of tAK to purified porcine mucin using SPDP.

Coupling of tAK to Mucus to Validate Processes Designed to Reduce Mucus Contamination of Medical Products Mucus is purified from a mucus-producing cell line such as normal human bronchial cells, cultured cells or is collected from sputum samples from patients. Washing in water or low salt solutions is sufficient to separate the mucin from most other components. Alternatively, purified mucin of animal origin e.g., porcine mucin, can also be used. The purified preparation is cross-linked to tAK using the methods described above, either to the protein component, through SPDP-coupling of the proteins as shown in FIG. 7, or to the carbohydrate component using the specific methods set out in Example 23. Deposition and subsequent use of the indicator is as described in Examples 23 and 24. FIG. 8 shows the results of the use of a tAK-mucin conjugate to monitor the removal of mucin in a washer-disinfector.

The invention claimed is:

1. A biological process indicator for validating a treatment process in which the amount or activity of a contaminant in a sample is reduced, wherein the indicator comprises a thermostable kinase covalently linked to a biological component, wherein the biological component consists of a molecule that mimics the sensitivity of the contaminant to the treatment process and wherein the molecule is selected from a group consisting of a blood protein, a fungal protein, a self-aggregating protein, a bacterial fimbrial protein, a bacterial toxin protein, a bacterial spore protein, a nucleic acid, a lipid, and a carbohydrate, with the proviso that the biological component is not an antibody, wherein:

(a) the fungal protein is a hydrophobin, a fungal spore protein, a hyphal protein, a mycotoxin, or a fungal prion; and (b) the self-aggregating protein is a prion, a prion mimetic protein, an amyloid fibril, beta amyloid protein, tau protein, polyadenine binding protein, lung surfactant protein C, a hydrophobin, a chaplin, a rodlin, a gram positive spore coat protein, or a barnacle cement-like protein;

wherein the thermostable kinase has a reference activity, as measured by a luminometer or luminescent assay, of at least 1,000,000 Relative Light Units (RLU) per mg kinase prior to the treatment process;

wherein the thermostable kinase and the biological component are products of recombinant expression in bacteria; and wherein the biological process indicator is immobilized in or on a solid support.

2. The biological process indicator of claim 1, wherein said blood protein is a blood clotting protein, a serum protein, a platelet protein, a blood cell glycoprotein, or haemoglobin.

3. The biological process indicator of claim 2, wherein said blood clotting protein is fibrin, fibrinogen, or a transglutaminase substrate.

4. The biological process indicator of claim 1, wherein the nucleic acid is a DNA molecule or an RNA molecule.

5. The biological process indicator of claim 1, wherein the carbohydrate is a exopolysaccharide or a lipopolysaccharide, a peptidoglycan, a chitin, a glucan, a lignin, a mucin, a glycolipid, a glycoprotein, a spore extract, a polysaccharide from yeast capsules, or an invertebrate secretion.

6. The biological process indicator of claim 1, wherein the lipid is a glycolipid or a ganglioside.

7. The biological process indicator of claim 1, wherein the indicator is part of a biological matrix.

8. The biological process indicator of claim 7, wherein the biological matrix is a mimetic of the sample.

9. The biological process indicator of claim 7, wherein the biological matrix comprises one or more components consisting of blood, serum, albumin, mucus, egg, neurological tissue, food, culled animal material, or a commercially-available test soil.

10. The biological process indicator of claim 1, wherein the thermostable kinase is an adenylate kinase, an acetate kinase or a pyruvate kinase.

11. The biological process indicator of claim 1, wherein the thermostable kinase comprises an amino acid sequence comprising SEQ ID NOS:1-25, 31, 32, 34-36, 38, 40, 42, 48-50, 52, 54, 61, 67, 72, or 73.

12. The biological process indicator of claim 1, wherein the thermostable kinase is encoded by a DNA comprising a nucleotide sequence comprising SEQ ID NOS:26-30, 37, 39, 41, 42, 47, 49, 51, 53, or 60.

13. A biological process indicator of claim 1, wherein the indicator further comprises an agent to stabilize the kinase.

14. The biological process indicator of claim 13, wherein the stabilizing agent is a metal ion, a sugar, a sugar alcohol or a gel-forming agent.

15. The biological process indicator of claim 1, wherein the biological component and the kinase are linked together in the form of a fusion protein.

16. The biological process indicator of claim 1, wherein the biological process indicator is immobilized in or on the solid support by chemical cross-linking or adsorption.

17. The biological process indicator of claim 1, wherein the solid support is an indicator strip, a dip-stick or a bead.

18. A kit for use in validating a treatment process in which the amount or activity of a contaminant in a sample is reduced, comprising:

(a) a biological process indicator comprising a thermostable kinase covalently linked to a biological component that mimics the sensitivity of the contaminant to the treatment process, consisting of a blood protein, a fungal protein, a self-aggregating protein, a bacterial fimbrial protein, a bacterial toxin protein, a bacterial spore protein, a nucleic acid, a lipid, and a carbohydrate, with the proviso that the biological component is not an antibody, wherein i. the fungal protein is a hydrophobin protein, a fungal spore protein, a hyphal protein, a mycotoxin, or a fungal prion;

ii. the self-aggregating protein is a prion, a prion mimetic protein, a amyloid fibril, beta amyloid protein, tau protein, polyadenine binding protein, lung surfactant protein C, a hydrophobin, a chaplin, a rodlin, a gram positive spore coat protein, and a barnacle cement-like protein; and (b) a substrate for the thermostable kinase;

wherein the thermostable kinase has a reference activity, as measured by a luminometer or luminescent assay, of at least 1,000.000 Relative Light Units (RLU) per mg kinase prior to the treatment process;

wherein the thermostable kinase and the biological component are products of recombinant expression in bacteria; and wherein the biological process indicator is immobilized in or on a solid support.

19. The kit of claim 18, wherein the substrate for the thermostable kinase is ADP.

20. The kit of claim 18, further comprising luciferin/luciferase.

21. The kit of claim 18, further comprising a look-up table correlating the kinase activity of the indicator with the amount or activity of the contaminant.

* * * * *

SEQUENCE LISTING

```
<160> NUMBER OF SEQ ID NOS: 77

<210> SEQ ID NO 1
<211> LENGTH: 195
<212> TYPE: PRT
<213> ORGANISM: Sulfolobus solfataricus

<400> SEQUENCE: 1

Met Lys Ile Gly Ile Val Thr Gly Ile Pro Gly Val Gly Lys Thr Thr
1               5                   10                  15

Val Leu Ser Phe Ala Asp Lys Ile Leu Thr Glu Lys Gly Ile Ser His
            20                  25                  30

Lys Ile Val Asn Tyr Gly Asp Tyr Met Leu Asn Thr Ala Leu Lys Glu
        35                  40                  45

Gly Tyr Val Lys Ser Arg Asp Glu Ile Arg Lys Leu Gln Ile Glu Lys
    50                  55                  60

Gln Arg Glu Leu Gln Ala Leu Ala Ala Arg Arg Ile Val Glu Asp Leu
65                  70                  75                  80

Ser Leu Leu Gly Asp Glu Gly Ile Gly Leu Ile Asp Thr His Ala Val
                85                  90                  95

Ile Arg Thr Pro Ala Gly Tyr Leu Pro Gly Leu Pro Arg His Val Ile
            100                 105                 110

Glu Val Leu Ser Pro Lys Val Ile Phe Leu Leu Glu Ala Asp Pro Lys
        115                 120                 125

Ile Ile Leu Glu Arg Gln Lys Arg Asp Ser Ser Arg Ala Arg Thr Asp
```

```
    130                 135                 140

Tyr Ser Asp Thr Ala Val Ile Asn Glu Val Ile Gln Phe Ala Arg Tyr
145                 150                 155                 160

Ser Ala Met Ala Ser Ala Val Leu Val Gly Ala Ser Val Lys Val Val
                165                 170                 175

Val Asn Gln Glu Gly Asp Pro Ser Ile Ala Ala Ser Glu Ile Ile Asn
            180                 185                 190

Ser Leu Met
        195


<210> SEQ ID NO 2
<211> LENGTH: 194
<212> TYPE: PRT
<213> ORGANISM: Sulfolobus acidocaldarius

<400> SEQUENCE: 2

Met Lys Ile Gly Ile Val Thr Gly Ile Pro Gly Val Gly Lys Ser Thr
1               5                   10                  15

Val Leu Ala Lys Val Lys Glu Ile Leu Asp Asn Gln Gly Ile Asn Asn
            20                  25                  30

Lys Ile Ile Asn Tyr Gly Asp Phe Met Leu Ala Thr Ala Leu Lys Leu
        35                  40                  45

Gly Tyr Ala Lys Asp Arg Asp Glu Met Arg Lys Leu Ser Val Glu Lys
    50                  55                  60

Gln Lys Lys Leu Gln Ile Asp Ala Ala Lys Gly Ile Ala Glu Glu Ala
65                  70                  75                  80

Arg Ala Gly Gly Glu Gly Tyr Leu Phe Ile Asp Thr His Ala Val Ile
                85                  90                  95

Arg Thr Pro Ser Gly Tyr Leu Pro Gly Leu Pro Ser Tyr Val Ile Thr
            100                 105                 110

Glu Ile Asn Pro Ser Val Ile Phe Leu Leu Glu Ala Asp Pro Lys Ile
        115                 120                 125

Ile Leu Ser Arg Gln Lys Arg Asp Thr Thr Arg Asn Arg Asn Asp Tyr
    130                 135                 140

Ser Asp Glu Ser Val Ile Leu Glu Thr Ile Asn Phe Ala Arg Tyr Ala
145                 150                 155                 160

Ala Thr Ala Ser Ala Val Leu Ala Gly Ser Thr Val Lys Val Ile Val
                165                 170                 175

Asn Val Glu Gly Asp Pro Ser Ile Ala Ala Asn Glu Ile Ile Arg Ser
            180                 185                 190

Met Lys


<210> SEQ ID NO 3
<211> LENGTH: 197
<212> TYPE: PRT
<213> ORGANISM: Sulfolobus tokodaii

<400> SEQUENCE: 3

Met Ser Lys Met Lys Ile Gly Ile Val Thr Gly Ile Pro Gly Val Gly
1               5                   10                  15

Lys Thr Thr Val Leu Ser Lys Val Lys Glu Ile Leu Glu Glu Lys Lys
            20                  25                  30

Ile Asn Asn Lys Ile Val Asn Tyr Gly Asp Tyr Met Leu Met Thr Ala
        35                  40                  45

Met Lys Leu Gly Tyr Val Asn Asn Arg Asp Glu Met Arg Lys Leu Pro
    50                  55                  60
```

Val Glu Lys Gln Lys Gln Leu Gln Ile Glu Ala Ala Arg Gly Ile Ala
65 70 75 80

Asn Glu Ala Lys Glu Gly Gly Asp Gly Leu Leu Phe Ile Asp Thr His
85 90 95

Ala Val Ile Arg Thr Pro Ser Gly Tyr Leu Pro Gly Leu Pro Lys Tyr
100 105 110

Val Ile Glu Glu Ile Asn Pro Arg Val Ile Phe Leu Leu Glu Ala Asp
115 120 125

Pro Lys Val Ile Leu Asp Arg Gln Lys Arg Asp Thr Ser Arg Ser Arg
130 135 140

Ser Asp Tyr Ser Asp Glu Arg Ile Ile Ser Glu Thr Ile Asn Phe Ala
145 150 155 160

Arg Tyr Ala Ala Met Ala Ser Ala Val Leu Val Gly Ala Thr Val Lys
165 170 175

Ile Val Ile Asn Val Glu Gly Asp Pro Ala Val Ala Ala Asn Glu Ile
180 185 190

Ile Asn Ser Met Leu
195

<210> SEQ ID NO 4
<211> LENGTH: 196
<212> TYPE: PRT
<213> ORGANISM: Pyrococcus furiosus

<400> SEQUENCE: 4

Met Pro Phe Val Val Ile Ile Thr Gly Ile Pro Gly Val Gly Lys Ser
1 5 10 15

Thr Ile Thr Arg Leu Ala Leu Gln Arg Thr Lys Ala Lys Phe Arg Leu
20 25 30

Ile Asn Phe Gly Asp Leu Met Phe Glu Glu Ala Val Lys Ala Gly Leu
35 40 45

Val Lys His Arg Asp Glu Met Arg Lys Leu Pro Leu Lys Ile Gln Arg
50 55 60

Glu Leu Gln Met Lys Ala Ala Lys Lys Ile Thr Glu Met Ala Lys Glu
65 70 75 80

His Pro Ile Leu Val Asp Thr His Ala Thr Ile Lys Thr Pro His Gly
85 90 95

Tyr Met Leu Gly Leu Pro Tyr Glu Val Val Lys Thr Leu Asn Pro Asn
100 105 110

Phe Ile Val Ile Ile Glu Ala Thr Pro Ser Glu Ile Leu Gly Arg Arg
115 120 125

Leu Arg Asp Leu Lys Arg Asp Arg Asp Val Glu Thr Glu Glu Gln Ile
130 135 140

Gln Arg His Gln Asp Leu Asn Arg Ala Ala Ala Ile Ala Tyr Ala Met
145 150 155 160

His Ser Asn Ala Leu Ile Lys Ile Ile Glu Asn His Glu Asp Lys Gly
165 170 175

Leu Glu Glu Ala Val Asn Glu Leu Val Lys Ile Leu Asp Leu Ala Val
180 185 190

Asn Glu Tyr Ala
195

<210> SEQ ID NO 5
<211> LENGTH: 196
<212> TYPE: PRT

<213> ORGANISM: Pyrococcus horikoshii

<400> SEQUENCE: 5

```
Met Pro Phe Val Val Ile Ile Thr Gly Ile Pro Gly Val Gly Lys Ser
1               5                   10                  15

Thr Ile Thr Lys Leu Ala Leu Gln Arg Thr Arg Ala Lys Phe Lys Leu
            20                  25                  30

Ile Asn Phe Gly Asp Leu Met Phe Glu Glu Ala Leu Lys Leu Lys Leu
        35                  40                  45

Val Lys His Arg Asp Glu Met Arg Lys Leu Pro Leu Glu Val Gln Arg
    50                  55                  60

Glu Leu Gln Met Asn Ala Ala Lys Lys Ile Ala Glu Met Ala Lys Asn
65                  70                  75                  80

Tyr Pro Ile Leu Leu Asp Thr His Ala Thr Ile Lys Thr Pro His Gly
                85                  90                  95

Tyr Leu Leu Gly Leu Pro Tyr Glu Val Ile Lys Ile Leu Asn Pro Asn
            100                 105                 110

Phe Ile Val Ile Ile Glu Ala Thr Pro Ser Glu Ile Leu Gly Arg Arg
        115                 120                 125

Leu Arg Asp Leu Lys Arg Asp Arg Asp Val Glu Thr Glu Glu Gln Ile
    130                 135                 140

Gln Arg His Gln Asp Leu Asn Arg Ala Ala Ala Ile Thr Tyr Ala Met
145                 150                 155                 160

His Ser Asn Ala Leu Ile Lys Ile Ile Glu Asn His Glu Asp Lys Gly
                165                 170                 175

Leu Glu Glu Ala Val Asn Glu Leu Val Lys Ile Leu Asp Leu Ala Val
            180                 185                 190

Lys Glu Tyr Ala
        195
```

<210> SEQ ID NO 6
<211> LENGTH: 196
<212> TYPE: PRT
<213> ORGANISM: Pyrococcus abyssi

<400> SEQUENCE: 6

```
Met Ser Phe Val Val Ile Ile Thr Gly Ile Pro Gly Val Gly Lys Ser
1               5                   10                  15

Thr Ile Thr Arg Leu Ala Leu Gln Arg Thr Lys Ala Lys Phe Lys Leu
            20                  25                  30

Ile Asn Phe Gly Asp Leu Met Phe Glu Glu Ala Val Lys Ala Gly Leu
        35                  40                  45

Val Asn His Arg Asp Glu Met Arg Lys Leu Pro Leu Glu Ile Gln Arg
    50                  55                  60

Asp Leu Gln Met Lys Val Ala Lys Lys Ile Ser Glu Met Ala Arg Gln
65                  70                  75                  80

Gln Pro Ile Leu Leu Asp Thr His Ala Thr Ile Lys Thr Pro His Gly
                85                  90                  95

Tyr Leu Leu Gly Leu Pro Tyr Glu Val Ile Lys Thr Leu Asn Pro Asn
            100                 105                 110

Phe Ile Val Ile Ile Glu Ala Thr Pro Ser Glu Ile Leu Gly Arg Arg
        115                 120                 125

Leu Arg Asp Leu Lys Arg Asp Arg Asp Val Glu Thr Glu Glu Gln Ile
    130                 135                 140

Gln Arg His Gln Asp Leu Asn Arg Ala Ala Ala Ile Ala Tyr Ala Met
```

-continued

```
145                 150                 155                 160

His Ser Asn Ala Leu Ile Lys Ile Ile Glu Asn His Glu Asp Lys Gly
                165                 170                 175

Leu Glu Glu Ala Val Asn Glu Leu Val Glu Ile Leu Asp Leu Ala Val
            180                 185                 190

Lys Glu Tyr Ala
        195
```

<210> SEQ ID NO 7
<211> LENGTH: 192
<212> TYPE: PRT
<213> ORGANISM: Methanococcus thermolithotrophicus

<400> SEQUENCE: 7

```
Met Lys Asn Lys Leu Val Val Val Thr Gly Val Pro Gly Val Gly Gly
1               5                   10                  15

Thr Thr Ile Thr Gln Lys Ala Met Glu Lys Leu Ser Glu Glu Gly Ile
            20                  25                  30

Asn Tyr Lys Met Val Asn Phe Gly Thr Val Met Phe Glu Val Ala Gln
        35                  40                  45

Glu Glu Asn Leu Val Glu Asp Arg Asp Gln Met Arg Lys Leu Asp Pro
    50                  55                  60

Asp Thr Gln Lys Arg Ile Gln Lys Leu Ala Gly Arg Lys Ile Ala Glu
65                  70                  75                  80

Met Val Lys Glu Ser Pro Val Val Val Asp Thr His Ser Thr Ile Lys
                85                  90                  95

Thr Pro Lys Gly Tyr Leu Pro Gly Leu Pro Val Trp Val Leu Asn Glu
            100                 105                 110

Leu Asn Pro Asp Ile Ile Ile Val Val Glu Thr Ser Gly Asp Glu Ile
        115                 120                 125

Leu Ile Arg Arg Leu Asn Asp Glu Thr Arg Asn Arg Asp Leu Glu Thr
    130                 135                 140

Thr Ala Gly Ile Glu Glu His Gln Ile Met Asn Arg Ala Ala Ala Met
145                 150                 155                 160

Thr Tyr Gly Val Leu Thr Gly Ala Thr Val Lys Ile Ile Gln Asn Lys
                165                 170                 175

Asn Asn Leu Leu Asp Tyr Ala Val Glu Glu Leu Ile Ser Val Leu Arg
            180                 185                 190
```

<210> SEQ ID NO 8
<211> LENGTH: 192
<212> TYPE: PRT
<213> ORGANISM: Methanococcus voltae

<400> SEQUENCE: 8

```
Met Lys Asn Lys Val Val Val Val Thr Gly Val Pro Gly Val Gly Ser
1               5                   10                  15

Thr Thr Ser Ser Gln Leu Ala Met Asp Asn Leu Arg Lys Glu Gly Val
            20                  25                  30

Asn Tyr Lys Met Val Ser Phe Gly Ser Val Met Phe Glu Val Ala Lys
        35                  40                  45

Glu Glu Asn Leu Val Ser Asp Arg Asp Gln Met Arg Lys Met Asp Pro
    50                  55                  60

Glu Thr Gln Lys Arg Ile Gln Lys Met Ala Gly Arg Lys Ile Ala Glu
65                  70                  75                  80

Met Ala Lys Glu Ser Pro Val Ala Val Asp Thr His Ser Thr Val Ser
```

-continued

```
                85                  90                  95

Thr Pro Lys Gly Tyr Leu Pro Gly Leu Pro Ser Trp Val Leu Asn Glu
            100                 105                 110

Leu Asn Pro Asp Leu Ile Ile Val Val Glu Thr Thr Gly Asp Glu Ile
        115                 120                 125

Leu Met Arg Arg Met Ser Asp Glu Thr Arg Val Arg Asp Leu Asp Thr
    130                 135                 140

Ala Ser Thr Ile Glu Gln His Gln Phe Met Asn Arg Cys Ala Ala Met
145                 150                 155                 160

Ser Tyr Gly Val Leu Thr Gly Ala Thr Val Lys Ile Val Gln Asn Arg
                165                 170                 175

Asn Gly Leu Leu Asp Gln Ala Val Glu Glu Leu Thr Asn Val Leu Arg
            180                 185                 190


<210> SEQ ID NO 9
<211> LENGTH: 195
<212> TYPE: PRT
<213> ORGANISM: Methanococcus jannaschii

<400> SEQUENCE: 9

Met Met Met Met Lys Asn Lys Val Val Val Ile Val Gly Val Pro Gly
1               5                   10                  15

Val Gly Ser Thr Thr Val Thr Asn Lys Ala Ile Glu Glu Leu Lys Lys
            20                  25                  30

Glu Gly Ile Glu Tyr Lys Ile Val Asn Phe Gly Thr Val Met Phe Glu
        35                  40                  45

Ile Ala Lys Glu Glu Gly Leu Val Glu His Arg Asp Gln Leu Arg Lys
    50                  55                  60

Leu Pro Pro Glu Glu Gln Lys Arg Ile Gln Lys Leu Ala Gly Lys Lys
65                  70                  75                  80

Ile Ala Glu Met Ala Lys Glu Phe Asn Ile Val Val Asp Thr His Ser
                85                  90                  95

Thr Ile Lys Thr Pro Lys Gly Tyr Leu Pro Gly Leu Pro Ala Trp Val
            100                 105                 110

Leu Glu Glu Leu Asn Pro Asp Ile Ile Val Leu Val Glu Ala Glu Asn
        115                 120                 125

Asp Glu Ile Leu Met Arg Arg Leu Lys Asp Glu Thr Arg Gln Arg Asp
    130                 135                 140

Phe Glu Ser Thr Glu Asp Ile Gly Glu His Ile Phe Met Asn Arg Cys
145                 150                 155                 160

Ala Ala Met Thr Tyr Ala Val Leu Thr Gly Ala Thr Val Lys Ile Ile
                165                 170                 175

Lys Asn Arg Asp Phe Leu Leu Asp Lys Ala Val Gln Glu Leu Ile Glu
            180                 185                 190

Val Leu Lys
        195


<210> SEQ ID NO 10
<211> LENGTH: 191
<212> TYPE: PRT
<213> ORGANISM: Methanopyrus kandleri

<400> SEQUENCE: 10

Met Gly Tyr Val Ile Val Ala Thr Gly Val Pro Gly Val Gly Ala Thr
1               5                   10                  15

Thr Val Thr Thr Glu Ala Val Lys Glu Leu Glu Gly Tyr Glu His Val
```

```
            20                  25                  30

Asn Tyr Gly Asp Val Met Leu Glu Ile Ala Lys Glu Glu Gly Leu Val
        35                  40                  45

Glu His Arg Asp Glu Ile Arg Lys Leu Pro Ala Glu Lys Gln Arg Glu
    50                  55                  60

Ile Gln Arg Leu Ala Ala Arg Arg Ile Ala Lys Met Ala Glu Glu Lys
65                  70                  75                  80

Glu Gly Ile Ile Val Asp Thr His Cys Thr Ile Lys Thr Pro Ala Gly
                85                  90                  95

Tyr Leu Pro Gly Leu Pro Ile Trp Val Leu Glu Glu Leu Gln Pro Asp
            100                 105                 110

Val Ile Val Leu Ile Glu Ala Asp Pro Asp Glu Ile Met Met Arg Arg
        115                 120                 125

Val Lys Asp Ser Glu Glu Arg Gln Arg Asp Tyr Asp Arg Ala His Glu
    130                 135                 140

Ile Glu Glu His Gln Lys Met Asn Arg Met Ala Ala Met Ala Tyr Ala
145                 150                 155                 160

Ala Leu Thr Gly Ala Thr Val Lys Ile Ile Glu Asn His Asp Asp Arg
                165                 170                 175

Leu Glu Glu Ala Val Arg Glu Phe Val Glu Thr Val Arg Ser Leu
            180                 185                 190


<210> SEQ ID NO 11
<211> LENGTH: 192
<212> TYPE: PRT
<213> ORGANISM: Methanotorris igneus

<400> SEQUENCE: 11

Met Lys Asn Lys Val Val Val Val Thr Gly Val Pro Gly Val Gly Gly
1               5                   10                  15

Thr Thr Leu Thr Gln Lys Thr Ile Glu Lys Leu Lys Glu Glu Gly Ile
            20                  25                  30

Glu Tyr Lys Met Val Asn Phe Gly Thr Val Met Phe Glu Val Ala Lys
        35                  40                  45

Glu Glu Gly Leu Val Glu Asp Arg Asp Gln Met Arg Lys Leu Asp Pro
    50                  55                  60

Asp Thr Gln Lys Arg Ile Gln Lys Leu Ala Gly Arg Lys Ile Ala Glu
65                  70                  75                  80

Met Ala Lys Glu Ser Asn Val Ile Val Asp Thr His Ser Thr Val Lys
                85                  90                  95

Thr Pro Lys Gly Tyr Leu Ala Gly Leu Pro Ile Trp Val Leu Glu Glu
            100                 105                 110

Leu Asn Pro Asp Ile Ile Val Ile Val Glu Thr Ser Ser Asp Glu Ile
        115                 120                 125

Leu Met Arg Arg Leu Gly Asp Ala Thr Arg Asn Arg Asp Ile Glu Leu
    130                 135                 140

Thr Ser Asp Ile Asp Glu His Gln Phe Met Asn Arg Cys Ala Ala Met
145                 150                 155                 160

Ala Tyr Gly Val Leu Thr Gly Ala Thr Val Lys Ile Ile Lys Asn Arg
                165                 170                 175

Asp Gly Leu Leu Asp Lys Ala Val Glu Glu Leu Ile Ser Val Leu Lys
            180                 185                 190


<210> SEQ ID NO 12
<211> LENGTH: 197
```

<212> TYPE: PRT
<213> ORGANISM: Pyrobaculum aerophilum

<400> SEQUENCE: 12

Met Lys Ile Val Ile Val Ala Leu Pro Gly Ser Gly Lys Thr Thr Ile
1 5 10 15

Leu Asn Phe Val Lys Gln Lys Leu Pro Asp Val Lys Ile Val Asn Tyr
20 25 30

Gly Asp Val Met Leu Glu Ile Ala Lys Lys Arg Phe Gly Ile Gln His
35 40 45

Arg Asp Glu Met Arg Lys Lys Ile Pro Val Asp Glu Tyr Arg Lys Val
50 55 60

Gln Glu Glu Ala Ala Glu Tyr Ile Ala Ser Leu Thr Gly Asp Val Ile
65 70 75 80

Ile Asp Thr His Ala Ser Ile Lys Ile Gly Gly Gly Tyr Tyr Pro Gly
85 90 95

Leu Pro Asp Arg Ile Ile Ser Lys Leu Lys Pro Asp Val Ile Leu Leu
100 105 110

Leu Glu Tyr Asp Pro Lys Val Ile Leu Glu Arg Arg Lys Lys Asp Pro
115 120 125

Asp Arg Phe Arg Asp Leu Glu Ser Glu Glu Glu Ile Glu Met His Gln
130 135 140

Gln Ala Asn Arg Tyr Tyr Ala Phe Ala Ala Ala Asn Ala Gly Glu Ser
145 150 155 160

Thr Val His Val Leu Asn Phe Arg Gly Lys Pro Glu Ser Arg Pro Phe
165 170 175

Glu His Ala Glu Val Ala Ala Glu Tyr Ile Val Asn Leu Ile Leu Arg
180 185 190

Thr Arg Gln Lys Ser
195

<210> SEQ ID NO 13
<211> LENGTH: 220
<212> TYPE: PRT
<213> ORGANISM: Thermotoga maritima

<400> SEQUENCE: 13

Met Met Ala Tyr Leu Val Phe Leu Gly Pro Pro Gly Ala Gly Lys Gly
1 5 10 15

Thr Tyr Ala Lys Arg Ile Gln Glu Lys Thr Gly Ile Pro His Ile Ser
20 25 30

Thr Gly Asp Ile Phe Arg Asp Ile Val Lys Lys Glu Asn Asp Glu Leu
35 40 45

Gly Lys Lys Ile Lys Glu Ile Met Glu Lys Gly Glu Leu Val Pro Asp
50 55 60

Glu Leu Val Asn Glu Val Val Lys Arg Arg Leu Ser Glu Lys Asp Cys
65 70 75 80

Glu Lys Gly Phe Ile Leu Asp Gly Tyr Pro Arg Thr Val Ala Gln Ala
85 90 95

Glu Phe Leu Asp Ser Phe Leu Glu Ser Gln Asn Lys Gln Leu Thr Ala
100 105 110

Ala Val Leu Phe Asp Val Pro Glu Asp Val Val Val Gln Arg Leu Thr
115 120 125

Ser Arg Arg Ile Cys Pro Lys Cys Gly Arg Ile Tyr Asn Met Ile Ser
130 135 140

```
Leu Pro Pro Lys Glu Asp Glu Leu Cys Asp Asp Cys Lys Val Lys Leu
145                 150                 155                 160

Val Gln Arg Asp Asp Asp Lys Glu Glu Thr Val Arg His Arg Tyr Lys
                165                 170                 175

Val Tyr Leu Glu Lys Thr Gln Pro Val Ile Asp Tyr Tyr Gly Lys Lys
            180                 185                 190

Gly Ile Leu Lys Arg Val Asp Gly Thr Ile Gly Ile Asp Asn Val Val
        195                 200                 205

Ala Glu Val Leu Lys Ile Ile Gly Trp Ser Asp Lys
    210                 215                 220


<210> SEQ ID NO 14
<211> LENGTH: 204
<212> TYPE: PRT
<213> ORGANISM: Aeropyrum pernix

<400> SEQUENCE: 14

Met Lys Val Arg His Pro Phe Lys Val Val Val Val Thr Gly Val Pro
1               5                   10                  15

Gly Val Gly Lys Thr Thr Val Ile Lys Glu Leu Gln Gly Leu Ala Glu
            20                  25                  30

Lys Glu Gly Val Lys Leu His Ile Val Asn Phe Gly Ser Phe Met Leu
        35                  40                  45

Asp Thr Ala Val Lys Leu Gly Leu Val Glu Asp Arg Asp Lys Ile Arg
    50                  55                  60

Thr Leu Pro Leu Arg Arg Gln Leu Glu Leu Gln Arg Glu Ala Ala Lys
65                  70                  75                  80

Arg Ile Val Ala Glu Ala Ser Lys Ala Leu Gly Gly Asp Gly Val Leu
                85                  90                  95

Ile Ile Asp Thr His Ala Leu Val Lys Thr Val Ala Gly Tyr Trp Pro
            100                 105                 110

Gly Leu Pro Lys His Val Leu Asp Glu Leu Lys Pro Asp Met Ile Ala
        115                 120                 125

Val Val Glu Ala Ser Pro Glu Glu Val Ala Ala Arg Gln Ala Arg Asp
    130                 135                 140

Thr Thr Arg Tyr Arg Val Asp Ile Gly Gly Val Glu Gly Val Lys Arg
145                 150                 155                 160

Leu Met Glu Asn Ala Arg Ala Ala Ser Ile Ala Ser Ala Ile Gln Tyr
                165                 170                 175

Ala Ser Thr Val Ala Ile Val Glu Asn Arg Glu Gly Glu Ala Ala Lys
            180                 185                 190

Ala Ala Glu Glu Leu Leu Arg Leu Ile Lys Asn Leu
        195                 200


<210> SEQ ID NO 15
<211> LENGTH: 216
<212> TYPE: PRT
<213> ORGANISM: Archaeoglobus fulgidus

<400> SEQUENCE: 15

Met Asn Leu Ile Phe Leu Gly Pro Pro Gly Ala Gly Lys Gly Thr Gln
1               5                   10                  15

Ala Lys Arg Val Ser Glu Lys Tyr Gly Ile Pro Gln Ile Ser Thr Gly
            20                  25                  30

Asp Met Leu Arg Glu Ala Val Ala Lys Gly Thr Glu Leu Gly Lys Lys
        35                  40                  45
```

-continued

```
Ala Lys Glu Tyr Met Asp Lys Gly Glu Leu Val Pro Asp Glu Val Val
    50                  55                  60

Ile Gly Ile Val Lys Glu Arg Leu Gln Gln Pro Asp Cys Glu Lys Gly
65                  70                  75                  80

Phe Ile Leu Asp Gly Phe Pro Arg Thr Leu Ala Gln Ala Glu Ala Leu
                85                  90                  95

Asp Glu Met Leu Lys Glu Leu Asn Lys Lys Ile Asp Ala Val Ile Asn
            100                 105                 110

Val Val Val Pro Glu Glu Glu Val Val Lys Arg Ile Thr Tyr Arg Arg
        115                 120                 125

Thr Cys Arg Asn Cys Gly Ala Val Tyr His Leu Ile Tyr Ala Pro Pro
    130                 135                 140

Lys Glu Asp Asn Lys Cys Asp Lys Cys Gly Gly Glu Leu Tyr Gln Arg
145                 150                 155                 160

Asp Asp Lys Glu Glu Thr Val Arg Glu Arg Tyr Arg Val Tyr Lys Gln
                165                 170                 175

Asn Thr Glu Pro Leu Ile Asp Tyr Tyr Arg Lys Lys Gly Ile Leu Tyr
            180                 185                 190

Asp Val Asp Gly Thr Lys Asp Ile Glu Gly Val Trp Lys Glu Ile Glu
        195                 200                 205

Ala Ile Leu Glu Lys Ile Lys Ser
    210                 215


<210> SEQ ID NO 16
<211> LENGTH: 220
<212> TYPE: PRT
<213> ORGANISM: Pyrococcus abyssi

<400> SEQUENCE: 16

Met Asn Ile Leu Ile Phe Gly Pro Pro Gly Ser Gly Lys Ser Thr Gln
1               5                   10                  15

Ala Arg Arg Ile Thr Glu Arg Tyr Gly Leu Thr Tyr Ile Ala Ser Gly
            20                  25                  30

Asp Ile Ile Arg Ala Glu Ile Lys Ala Arg Thr Pro Leu Gly Ile Glu
        35                  40                  45

Met Glu Arg Tyr Leu Ser Arg Gly Asp Leu Ile Pro Asp Thr Ile Val
    50                  55                  60

Asn Thr Leu Ile Ile Ser Lys Leu Arg Arg Val Arg Glu Asn Phe Ile
65                  70                  75                  80

Met Asp Gly Tyr Pro Arg Thr Pro Glu Gln Val Ile Thr Leu Glu Asn
                85                  90                  95

Tyr Leu Tyr Asp His Gly Ile Lys Leu Asp Val Ala Ile Asp Ile Tyr
            100                 105                 110

Ile Thr Lys Glu Glu Ser Val Arg Arg Ile Ser Gly Arg Arg Ile Cys
        115                 120                 125

Ser Lys Cys Gly Ala Val Tyr His Val Glu Phe Asn Pro Pro Lys Val
    130                 135                 140

Pro Gly Lys Cys Asp Ile Cys Gly Gly Glu Leu Ile Gln Arg Pro Asp
145                 150                 155                 160

Asp Arg Pro Glu Ile Val Glu Lys Arg Tyr Asp Ile Tyr Ser Lys Asn
                165                 170                 175

Met Glu Pro Ile Ile Lys Phe Tyr Gln Lys Gln Gly Ile Tyr Val Arg
            180                 185                 190

Ile Asp Gly His Gly Ser Ile Asp Glu Val Trp Glu Arg Ile Arg Pro
        195                 200                 205
```

Leu Leu Asp Tyr Ile Tyr Asn Gln Glu Asn Arg Arg
    210                 215                 220

<210> SEQ ID NO 17
<211> LENGTH: 196
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (61)..(61)
<223> OTHER INFORMATION: The amino acid “X” may be K or E.
<220> FEATURE:
<221> NAME/KEY: MISC_FEATURE
<222> LOCATION: (75)..(75)
<223> OTHER INFORMATION: The amino acid “X” may be T or A.
<220> FEATURE:
<221> NAME/KEY: MISC_FEATURE
<222> LOCATION: (98)..(98)
<223> OTHER INFORMATION: The amino acid “X” may be M or L.
<220> FEATURE:
<221> NAME/KEY: MISC_FEATURE
<222> LOCATION: (157)..(157)
<223> OTHER INFORMATION: The amino acid “X” may be A, or a small
      hydrophobic residue (e.g. I or L) or a large hydrophobic residue
      (e.g. F), that increases the thermal stability of the enzyme.

<400> SEQUENCE: 17

Met Pro Phe Val Val Ile Ile Thr Gly Ile Pro Gly Val Gly Lys Ser
1               5                   10                  15

Thr Ile Thr Arg Leu Ala Leu Gln Arg Thr Lys Ala Lys Phe Arg Leu
            20                  25                  30

Ile Asn Phe Gly Asp Leu Met Phe Glu Glu Ala Val Lys Ala Gly Leu
        35                  40                  45

Val Lys His Arg Asp Glu Met Arg Lys Leu Pro Leu Xaa Ile Gln Arg
    50                  55                  60

Glu Leu Gln Met Lys Ala Ala Lys Lys Ile Xaa Glu Met Ala Lys Glu
65                  70                  75                  80

His Pro Ile Leu Val Asp Thr His Ala Thr Ile Lys Thr Pro His Gly
                85                  90                  95

Tyr Xaa Leu Gly Leu Pro Tyr Glu Val Val Lys Thr Leu Asn Pro Asn
            100                 105                 110

Phe Ile Val Ile Ile Glu Ala Thr Pro Ser Glu Ile Leu Gly Arg Arg
        115                 120                 125

Leu Arg Asp Leu Lys Arg Asp Arg Asp Val Glu Thr Glu Glu Gln Ile
    130                 135                 140

Gln Arg His Gln Asp Leu Asn Arg Ala Ala Ala Ile Xaa Tyr Ala Met
145                 150                 155                 160

His Ser Asn Ala Leu Ile Lys Ile Ile Glu Asn His Glu Asp Lys Gly
                165                 170                 175

Leu Glu Glu Ala Val Asn Glu Leu Val Lys Ile Leu Asp Leu Ala Val
            180                 185                 190

Asn Glu Tyr Ala
        195

<210> SEQ ID NO 18
<211> LENGTH: 196
<212> TYPE: PRT
<213> ORGANISM: Artificial Sequence
<220> FEATURE:
<223> OTHER INFORMATION: Synthetic
<220> FEATURE:

<221> NAME/KEY: MISC_FEATURE
<222> LOCATION: (47)..(47)
<223> OTHER INFORMATION: The amino acid "X" may be G, or may be any other residue that increases the thermal stability of the enzyme.
<220> FEATURE:
<221> NAME/KEY: MISC_FEATURE
<222> LOCATION: (157)..(157)
<223> OTHER INFORMATION: The amino acid "X" may be A, or a small hydrophobic residue (e.g. I or L) or a large hydrophobic residue (e.g. F), that increases the thermal stability of the enzyme.

<400> SEQUENCE: 18

```
Met Pro Phe Val Val Ile Ile Thr Gly Ile Pro Gly Val Gly Lys Ser
1               5                   10                  15

Thr Ile Thr Lys Leu Ala Leu Gln Arg Thr Arg Ala Lys Phe Lys Leu
            20                  25                  30

Ile Asn Phe Gly Asp Leu Met Phe Glu Glu Ala Leu Lys Leu Xaa Leu
        35                  40                  45

Val Lys His Arg Asp Glu Met Arg Lys Leu Pro Leu Glu Val Gln Arg
    50                  55                  60

Glu Leu Gln Met Asn Ala Ala Lys Lys Ile Ala Glu Met Ala Lys Asn
65                  70                  75                  80

Tyr Pro Ile Leu Leu Asp Thr His Ala Thr Ile Lys Thr Pro His Gly
                85                  90                  95

Tyr Leu Leu Gly Leu Pro Tyr Glu Val Ile Lys Ile Leu Asn Pro Asn
            100                 105                 110

Phe Ile Val Ile Ile Glu Ala Thr Pro Ser Glu Ile Leu Gly Arg Arg
        115                 120                 125

Leu Arg Asp Leu Lys Arg Asp Arg Asp Val Glu Thr Glu Glu Gln Ile
    130                 135                 140

Gln Arg His Gln Asp Leu Asn Arg Ala Ala Ala Ile Xaa Tyr Ala Met
145                 150                 155                 160

His Ser Asn Ala Leu Ile Lys Ile Ile Glu Asn His Glu Asp Lys Gly
                165                 170                 175

Leu Glu Glu Ala Val Asn Glu Leu Val Lys Ile Leu Asp Leu Ala Val
            180                 185                 190

Lys Glu Tyr Ala
        195
```

<210> SEQ ID NO 19
<211> LENGTH: 194
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (103)..(103)
<223> OTHER INFORMATION: The amino acid "X" may be A or M.

<400> SEQUENCE: 19

```
Met Lys Ile Gly Ile Val Thr Gly Ile Pro Gly Val Gly Lys Ser Thr
1               5                   10                  15

Val Leu Ala Lys Val Lys Glu Ile Leu Asp Asn Gln Gly Ile Asn Asn
            20                  25                  30

Lys Ile Ile Asn Tyr Gly Asp Phe Met Leu Ala Thr Ala Leu Lys Leu
        35                  40                  45

Gly Tyr Ala Lys Asp Arg Asp Glu Met Arg Lys Leu Ser Val Glu Lys
    50                  55                  60

Gln Lys Lys Leu Gln Ile Asp Ala Ala Lys Gly Ile Ala Glu Glu Ala
```

```
65                  70                  75                  80

Arg Ala Gly Gly Glu Gly Tyr Leu Phe Ile Asp Thr His Ala Val Ile
                85                  90                  95

Arg Thr Pro Ser Gly Tyr Xaa Pro Gly Leu Pro Ser Tyr Val Ile Thr
            100                 105                 110

Glu Ile Asn Pro Ser Val Ile Phe Leu Leu Glu Ala Asp Pro Lys Ile
        115                 120                 125

Ile Leu Ser Arg Gln Lys Arg Asp Thr Thr Arg Asn Arg Asn Asp Tyr
    130                 135                 140

Ser Asp Glu Ser Val Ile Leu Glu Thr Ile Asn Phe Ala Arg Tyr Ala
145                 150                 155                 160

Ala Thr Ala Ser Ala Val Leu Ala Gly Ser Thr Val Lys Val Ile Val
                165                 170                 175

Asn Val Glu Gly Asp Pro Ser Ile Ala Ala Asn Glu Ile Ile Arg Ser
            180                 185                 190

Met Lys
```

<210> SEQ ID NO 20
<211> LENGTH: 403
<212> TYPE: PRT
<213> ORGANISM: Thermotoga maritima

<400> SEQUENCE: 20

```
Met Arg Val Leu Val Ile Asn Ser Gly Ser Ser Ser Ile Lys Tyr Gln
1               5                   10                  15

Leu Ile Glu Met Glu Gly Glu Lys Val Leu Cys Lys Gly Ile Ala Glu
            20                  25                  30

Arg Ile Gly Ile Glu Gly Ser Arg Leu Val His Arg Val Gly Asp Glu
        35                  40                  45

Lys His Val Ile Glu Arg Glu Leu Pro Asp His Glu Glu Ala Leu Lys
    50                  55                  60

Leu Ile Leu Asn Thr Leu Val Asp Glu Lys Leu Gly Val Ile Lys Asp
65                  70                  75                  80

Leu Lys Glu Ile Asp Ala Val Gly His Arg Val Val His Gly Gly Glu
                85                  90                  95

Arg Phe Lys Glu Ser Val Leu Val Asp Glu Glu Val Leu Lys Ala Ile
            100                 105                 110

Glu Glu Val Ser Pro Leu Ala Pro Leu His Asn Pro Ala Asn Leu Met
        115                 120                 125

Gly Ile Lys Ala Ala Met Lys Leu Leu Pro Gly Val Pro Asn Val Ala
    130                 135                 140

Val Phe Asp Thr Ala Phe His Gln Thr Ile Pro Gln Lys Ala Tyr Leu
145                 150                 155                 160

Tyr Ala Ile Pro Tyr Glu Tyr Tyr Glu Lys Tyr Lys Ile Arg Arg Tyr
                165                 170                 175

Gly Phe His Gly Thr Ser His Arg Tyr Val Ser Lys Arg Ala Ala Glu
            180                 185                 190

Ile Leu Gly Lys Lys Leu Glu Glu Leu Lys Ile Ile Thr Cys His Ile
        195                 200                 205

Gly Asn Gly Ala Ser Val Ala Ala Val Lys Tyr Gly Lys Cys Val Asp
    210                 215                 220

Thr Ser Met Gly Phe Thr Pro Leu Glu Gly Leu Val Met Gly Thr Arg
225                 230                 235                 240

Ser Gly Asp Leu Asp Pro Ala Ile Pro Phe Phe Ile Met Glu Lys Glu
```

```
                245                 250                 255

Gly Ile Ser Pro Gln Glu Met Tyr Asp Ile Leu Asn Lys Lys Ser Gly
            260                 265                 270

Val Tyr Gly Leu Ser Lys Gly Phe Ser Ser Asp Met Arg Asp Ile Glu
        275                 280                 285

Glu Ala Ala Leu Lys Gly Asp Glu Trp Cys Lys Leu Val Leu Glu Ile
    290                 295                 300

Tyr Asp Tyr Arg Ile Ala Lys Tyr Ile Gly Ala Tyr Ala Ala Ala Met
305                 310                 315                 320

Asn Gly Val Asp Ala Ile Val Phe Thr Ala Gly Val Gly Glu Asn Ser
                325                 330                 335

Pro Ile Thr Arg Glu Asp Val Cys Ser Tyr Leu Glu Phe Leu Gly Val
            340                 345                 350

Lys Leu Asp Lys Gln Lys Asn Glu Glu Thr Ile Arg Gly Lys Glu Gly
        355                 360                 365

Ile Ile Ser Thr Pro Asp Ser Arg Val Lys Val Leu Val Val Pro Thr
    370                 375                 380

Asn Glu Glu Leu Met Ile Ala Arg Asp Thr Lys Glu Ile Val Glu Lys
385                 390                 395                 400

Ile Gly Arg


<210> SEQ ID NO 21
<211> LENGTH: 478
<212> TYPE: PRT
<213> ORGANISM: Pyrococcus horikoshii

<400> SEQUENCE: 21

Met Arg Arg Met Lys Leu Pro Ser His Lys Thr Lys Ile Val Ala Thr
1               5                   10                  15

Ile Gly Pro Ala Thr Asn Ser Lys Lys Met Ile Lys Lys Leu Ile Glu
            20                  25                  30

Ala Gly Met Asn Val Ala Arg Ile Asn Phe Ser His Gly Thr Phe Glu
        35                  40                  45

Glu His Ala Lys Ile Ile Glu Met Val Arg Glu Gln Ser Gln Lys Leu
    50                  55                  60

Asp Arg Arg Val Ala Ile Leu Ala Asp Leu Pro Gly Leu Lys Ile Arg
65                  70                  75                  80

Val Gly Glu Ile Lys Gly Gly Tyr Val Glu Leu Glu Arg Gly Glu Lys
                85                  90                  95

Val Thr Leu Thr Thr Lys Asp Ile Glu Gly Asp Glu Thr Thr Ile Pro
            100                 105                 110

Val Glu Tyr Lys Asp Phe Pro Lys Leu Val Ser Lys Gly Asp Val Ile
        115                 120                 125

Tyr Leu Ser Asp Gly Tyr Ile Val Leu Arg Val Glu Asp Val Lys Glu
    130                 135                 140

Asn Glu Val Glu Ala Val Val Ile Ser Gly Gly Lys Leu Phe Ser Arg
145                 150                 155                 160

Lys Gly Ile Asn Ile Pro Lys Ala Tyr Leu Pro Val Glu Ala Ile Thr
                165                 170                 175

Pro Arg Asp Ile Glu Ile Met Lys Phe Ala Ile Glu His Gly Val Asp
            180                 185                 190

Ala Ile Gly Leu Ser Phe Val Gly Asn Val Tyr Asp Val Leu Lys Ala
        195                 200                 205

Lys Ser Phe Leu Glu Arg Asn Gly Ala Gly Asp Thr Phe Val Ile Ala
```

```
    210                 215                 220

Lys Ile Glu Arg Pro Asp Ala Val Arg Asn Phe Asn Glu Ile Leu Asn
225                 230                 235                 240

Ala Ala Asp Gly Ile Met Ile Ala Arg Gly Asp Leu Gly Val Glu Met
                245                 250                 255

Pro Ile Glu Gln Leu Pro Ile Leu Gln Lys Arg Leu Ile Arg Lys Ala
            260                 265                 270

Asn Met Glu Gly Lys Pro Val Ile Thr Ala Thr Gln Met Leu Val Ser
        275                 280                 285

Met Thr Met Glu Lys Val Pro Thr Arg Ala Glu Val Thr Asp Val Ala
    290                 295                 300

Asn Ala Ile Leu Asp Gly Thr Asp Ala Val Met Leu Ser Glu Glu Thr
305                 310                 315                 320

Ala Val Gly Lys Phe Pro Ile Glu Ala Val Glu Met Met Ala Arg Ile
                325                 330                 335

Ala Lys Val Thr Glu Glu Tyr Arg Glu Ser Phe Gly Ile Thr Arg Met
            340                 345                 350

Arg Glu Phe Leu Glu Gly Thr Lys Arg Gly Thr Ile Lys Glu Ala Ile
        355                 360                 365

Thr Arg Ser Ile Ile Asp Ala Ile Cys Thr Ile Gly Ile Lys Phe Ile
    370                 375                 380

Leu Thr Pro Thr Lys Thr Gly Arg Thr Ala Arg Leu Ile Ser Arg Phe
385                 390                 395                 400

Lys Pro Lys Gln Trp Ile Leu Ala Phe Ser Thr Arg Glu Lys Val Cys
                405                 410                 415

Asn Asn Leu Met Phe Ser Tyr Gly Val Tyr Pro Phe Cys Met Glu Glu
            420                 425                 430

Gly Phe Asn Glu Asn Asp Ile Val Arg Leu Ile Lys Gly Leu Gly Leu
        435                 440                 445

Val Gly Ser Asp Asp Ile Val Leu Met Thr Glu Gly Lys Pro Ile Glu
    450                 455                 460

Lys Thr Val Gly Thr Asn Ser Ile Lys Ile Phe Gln Ile Ala
465                 470                 475


<210> SEQ ID NO 22
<211> LENGTH: 452
<212> TYPE: PRT
<213> ORGANISM: Sulfolobus solfataricus

<400> SEQUENCE: 22

Met Arg Lys Thr Lys Ile Val Ala Thr Leu Gly Pro Ser Ser Glu Glu
1               5                   10                  15

Lys Val Lys Glu Leu Ala Glu Tyr Val Asp Val Phe Arg Ile Asn Phe
            20                  25                  30

Ala His Gly Asp Glu Thr Ser His Arg Lys Tyr Phe Asp Leu Ile Arg
        35                  40                  45

Thr Tyr Ala Pro Glu Ser Ser Ile Ile Val Asp Leu Pro Gly Pro Lys
    50                  55                  60

Leu Arg Leu Gly Glu Leu Lys Glu Pro Ile Glu Val Lys Lys Gly Asp
65                  70                  75                  80

Lys Ile Val Phe Ser Gln Lys Asp Gly Ile Pro Val Asp Asp Glu Leu
                85                  90                  95

Phe Tyr Ser Ala Val Lys Glu Asn Ser Asp Ile Leu Ile Ala Asp Gly
            100                 105                 110
```

Thr Ile Arg Val Arg Val Lys Ser Lys Ala Lys Asp Arg Val Glu Gly
115 120 125

Thr Val Ile Glu Gly Gly Ile Leu Leu Ser Arg Lys Gly Ile Asn Ile
130 135 140

Pro Asn Val Asn Leu Lys Ser Gly Ile Thr Asp Asn Asp Leu Lys Leu
145 150 155 160

Leu Lys Arg Ala Leu Asp Leu Gly Ala Asp Tyr Ile Gly Leu Ser Phe
165 170 175

Val Ile Ser Glu Asn Asp Val Lys Lys Val Lys Glu Phe Val Gly Asp
180 185 190

Glu Ala Trp Val Ile Ala Lys Ile Glu Lys Ser Glu Ala Leu Lys Asn
195 200 205

Leu Thr Asn Ile Val Asn Glu Ser Asp Gly Ile Met Val Ala Arg Gly
210 215 220

Asp Leu Gly Val Glu Thr Gly Leu Glu Asn Leu Pro Leu Ile Gln Arg
225 230 235 240

Arg Ile Val Arg Thr Ser Arg Val Phe Gly Lys Pro Val Ile Leu Ala
245 250 255

Thr Gln Val Leu Thr Ser Met Ile Asn Ser Pro Ile Pro Thr Arg Ala
260 265 270

Glu Ile Ile Asp Ile Ser Asn Ser Ile Met Gln Gly Val Asp Ser Ile
275 280 285

Met Leu Ser Asp Glu Thr Ala Ile Gly Asn Tyr Pro Val Glu Ser Val
290 295 300

Arg Thr Leu His Asn Ile Ile Ser Asn Val Glu Lys Ser Val Lys His
305 310 315 320

Arg Pro Ile Gly Pro Leu Asn Ser Glu Ser Asp Ala Ile Ala Leu Ala
325 330 335

Ala Val Asn Ala Ser Lys Val Ser Lys Ala Asp Val Ile Val Val Tyr
340 345 350

Ser Arg Ser Gly Asn Ser Ile Leu Arg Val Ser Arg Leu Arg Pro Glu
355 360 365

Arg Asn Ile Ile Gly Val Ser Pro Asp Pro Arg Leu Ala Lys Lys Phe
370 375 380

Lys Leu Cys Tyr Gly Val Ile Pro Ile Ser Ile Asn Lys Lys Met Gln
385 390 395 400

Ser Ile Asp Glu Ile Ile Asp Val Ser Ala Lys Leu Met Gln Glu Lys
405 410 415

Ile Lys Asp Leu Lys Phe Lys Lys Ile Val Ile Val Gly Gly Asp Pro
420 425 430

Lys Gln Glu Ala Gly Lys Thr Asn Phe Val Ile Val Lys Thr Leu Glu
435 440 445

Gln Gln Lys Lys
450

<210> SEQ ID NO 23
<211> LENGTH: 466
<212> TYPE: PRT
<213> ORGANISM: Thermotoga maritima

<400> SEQUENCE: 23

Met Arg Ser Thr Lys Ile Val Cys Thr Val Gly Pro Arg Thr Asp Ser
1 5 10 15

Tyr Glu Met Ile Glu Lys Met Ile Asp Leu Gly Val Asn Val Phe Arg
20 25 30

-continued

```
Ile Asn Thr Ser His Gly Asp Trp Asn Glu Gln Glu Gln Lys Ile Leu
        35                  40                  45

Lys Ile Lys Asp Leu Arg Glu Lys Lys Lys Lys Pro Val Ala Ile Leu
    50                  55                  60

Ile Asp Leu Ala Gly Pro Lys Ile Arg Thr Gly Tyr Leu Glu Lys Glu
65                  70                  75                  80

Phe Val Glu Leu Lys Glu Gly Gln Ile Phe Thr Leu Thr Thr Lys Glu
                85                  90                  95

Ile Leu Gly Asn Glu His Ile Val Ser Val Asn Leu Ser Ser Leu Pro
            100                 105                 110

Lys Asp Val Lys Lys Gly Asp Thr Ile Leu Leu Ser Asp Gly Glu Ile
        115                 120                 125

Val Leu Glu Val Ile Glu Thr Thr Asp Thr Glu Val Lys Thr Val Val
    130                 135                 140

Lys Val Gly Gly Lys Ile Thr His Arg Arg Gly Val Asn Val Pro Thr
145                 150                 155                 160

Ala Asp Leu Ser Val Glu Ser Ile Thr Asp Arg Asp Arg Glu Phe Ile
                165                 170                 175

Lys Leu Gly Thr Leu His Asp Val Glu Phe Phe Ala Leu Ser Phe Val
            180                 185                 190

Arg Lys Pro Glu Asp Val Leu Lys Ala Lys Glu Glu Ile Arg Lys His
        195                 200                 205

Gly Lys Glu Ile Pro Val Ile Ser Lys Ile Glu Thr Lys Lys Ala Leu
    210                 215                 220

Glu Arg Leu Glu Glu Ile Ile Lys Val Ser Asp Gly Ile Met Val Ala
225                 230                 235                 240

Arg Gly Asp Leu Gly Val Glu Ile Pro Ile Glu Glu Val Pro Ile Val
                245                 250                 255

Gln Lys Glu Ile Ile Lys Leu Ser Lys Tyr Tyr Ser Lys Pro Val Ile
            260                 265                 270

Val Ala Thr Gln Ile Leu Glu Ser Met Ile Glu Asn Pro Phe Pro Thr
        275                 280                 285

Arg Ala Glu Val Thr Asp Ile Ala Asn Ala Ile Phe Asp Gly Ala Asp
    290                 295                 300

Ala Leu Leu Leu Thr Ala Glu Thr Ala Val Gly Lys His Pro Leu Glu
305                 310                 315                 320

Ala Ile Lys Val Leu Ser Lys Val Ala Lys Glu Ala Glu Lys Lys Leu
                325                 330                 335

Glu Phe Phe Arg Thr Ile Glu Tyr Asp Thr Ser Asp Ile Ser Glu Ala
            340                 345                 350

Ile Ser His Ala Cys Trp Gln Leu Ser Glu Ser Leu Asn Ala Lys Leu
        355                 360                 365

Ile Ile Thr Pro Thr Ile Ser Gly Ser Thr Ala Val Arg Val Ser Lys
    370                 375                 380

Tyr Asn Val Ser Gln Pro Ile Val Ala Leu Thr Pro Glu Glu Lys Thr
385                 390                 395                 400

Tyr Tyr Arg Leu Ser Leu Val Arg Lys Val Ile Pro Val Leu Ala Glu
                405                 410                 415

Lys Cys Ser Gln Glu Leu Glu Phe Ile Glu Lys Gly Leu Lys Lys Val
            420                 425                 430

Glu Glu Met Gly Leu Ala Glu Lys Gly Asp Leu Val Val Leu Thr Ser
        435                 440                 445
```

```
Gly Val Pro Gly Lys Val Gly Thr Thr Asn Thr Ile Arg Val Leu Lys
    450                 455                 460

Val Asp
465


<210> SEQ ID NO 24
<211> LENGTH: 477
<212> TYPE: PRT
<213> ORGANISM: Pyrococcus furiosus

<400> SEQUENCE: 24

Met Arg Arg Val Lys Leu Pro Ser His Lys Thr Lys Ile Val Ala Thr
1               5                   10                  15

Ile Gly Pro Ala Thr Asn Ser Arg Lys Met Ile Lys Gln Leu Ile Lys
            20                  25                  30

Ala Gly Met Asn Val Ala Arg Ile Asn Phe Ser His Gly Ser Phe Glu
        35                  40                  45

Glu His Ala Arg Val Ile Glu Ile Ile Arg Glu Glu Ala Gln Lys Leu
    50                  55                  60

Asp Arg Arg Val Ala Ile Leu Ala Asp Leu Pro Gly Leu Lys Ile Arg
65                  70                  75                  80

Val Gly Glu Ile Lys Gly Gly Tyr Val Glu Leu Lys Arg Gly Glu Lys
                85                  90                  95

Val Ile Leu Thr Thr Lys Asp Val Glu Gly Asp Glu Thr Thr Ile Pro
            100                 105                 110

Val Asp Tyr Lys Gly Phe Pro Asn Leu Val Ser Lys Gly Asp Ile Ile
        115                 120                 125

Tyr Leu Asn Asp Gly Tyr Ile Val Leu Lys Val Glu Asn Val Arg Glu
    130                 135                 140

Asn Glu Val Glu Ala Val Val Leu Ser Gly Gly Lys Leu Phe Ser Arg
145                 150                 155                 160

Lys Gly Val Asn Ile Pro Lys Ala Tyr Leu Pro Val Glu Ala Ile Thr
                165                 170                 175

Pro Lys Asp Phe Glu Ile Met Lys Phe Ala Ile Glu His Gly Val Asp
            180                 185                 190

Ala Ile Gly Leu Ser Phe Val Gly Ser Val Tyr Asp Val Leu Lys Ala
        195                 200                 205

Lys Ser Phe Leu Glu Lys Asn Asn Ala Glu Asp Val Phe Val Ile Ala
    210                 215                 220

Lys Ile Glu Arg Pro Asp Ala Val Arg Asn Phe Asp Glu Ile Leu Asn
225                 230                 235                 240

Ala Ala Asp Gly Ile Met Ile Ala Arg Gly Asp Leu Gly Val Glu Met
                245                 250                 255

Pro Ile Glu Gln Leu Pro Ile Leu Gln Lys Lys Leu Ile Arg Lys Ala
            260                 265                 270

Asn Met Glu Gly Lys Pro Val Ile Thr Ala Thr Gln Met Leu Val Ser
        275                 280                 285

Met Thr Thr Glu Lys Val Pro Thr Arg Ala Glu Val Thr Asp Val Ala
    290                 295                 300

Asn Ala Ile Leu Asp Gly Thr Asp Ala Val Met Leu Ser Glu Glu Thr
305                 310                 315                 320

Ala Ile Gly Lys Phe Pro Ile Glu Thr Val Glu Met Met Gly Lys Ile
                325                 330                 335

Ala Lys Val Thr Glu Glu Tyr Arg Glu Ser Phe Gly Leu Ser Arg Ile
            340                 345                 350
```

Arg Glu Phe Met Glu Ile Lys Lys Gly Thr Ile Lys Glu Ala Ile Thr
355 360 365

Arg Ser Ile Ile Asp Ala Ile Cys Thr Ile Asp Ile Lys Phe Ile Leu
370 375 380

Thr Pro Thr Arg Thr Gly Arg Thr Ala Arg Leu Ile Ser Arg Phe Lys
385 390 395 400

Pro Lys Gln Trp Ile Leu Ala Phe Ser Thr Asn Glu Arg Val Cys Asn
405 410 415

Asn Leu Met Phe Ser Tyr Gly Val Tyr Pro Phe Cys Leu Glu Glu Gly
420 425 430

Phe Asp Glu Asn Asp Ile Val Arg Leu Ile Lys Gly Leu Gly Leu Val
435 440 445

Glu Ser Asp Asp Met Val Leu Met Thr Glu Gly Lys Pro Ile Glu Lys
450 455 460

Thr Val Gly Thr Asn Ser Ile Lys Ile Phe Gln Ile Ala
465 470 475

<210> SEQ ID NO 25
<211> LENGTH: 408
<212> TYPE: PRT
<213> ORGANISM: Methanosarcina thermophila

<400> SEQUENCE: 25

Met Lys Val Leu Val Ile Asn Ala Gly Ser Ser Ser Leu Lys Tyr Gln
1 5 10 15

Leu Ile Asp Met Thr Asn Glu Ser Ala Leu Ala Val Gly Leu Cys Glu
20 25 30

Arg Ile Gly Ile Asp Asn Ser Ile Ile Thr Gln Lys Lys Phe Asp Gly
35 40 45

Lys Lys Leu Glu Lys Leu Thr Asp Leu Pro Thr His Lys Asp Ala Leu
50 55 60

Glu Glu Val Val Lys Ala Leu Thr Asp Asp Glu Phe Gly Val Ile Lys
65 70 75 80

Asp Met Gly Glu Ile Asn Ala Val Gly His Arg Val Val His Gly Gly
85 90 95

Glu Lys Phe Thr Thr Ser Ala Leu Tyr Asp Glu Gly Val Glu Lys Ala
100 105 110

Ile Lys Asp Cys Phe Glu Leu Ala Pro Leu His Asn Pro Pro Asn Met
115 120 125

Met Gly Ile Ser Ala Cys Ala Glu Ile Met Pro Gly Thr Pro Met Val
130 135 140

Ile Val Phe Asp Thr Ala Phe His Gln Thr Met Pro Pro Tyr Ala Tyr
145 150 155 160

Met Tyr Ala Leu Pro Tyr Asp Leu Tyr Glu Lys His Gly Val Arg Lys
165 170 175

Tyr Gly Phe His Gly Thr Ser His Lys Tyr Val Ala Glu Arg Ala Ala
180 185 190

Leu Met Leu Gly Lys Pro Ala Glu Glu Thr Lys Ile Ile Thr Cys His
195 200 205

Leu Gly Asn Gly Ser Ser Ile Thr Ala Val Glu Gly Gly Lys Ser Val
210 215 220

Glu Thr Ser Met Gly Phe Thr Pro Leu Glu Gly Leu Ala Met Gly Thr
225 230 235 240

Arg Cys Gly Ser Ile Asp Pro Ala Ile Val Pro Phe Leu Met Glu Lys

```
                245                 250                 255

Glu Gly Leu Thr Thr Arg Glu Ile Asp Thr Leu Met Asn Lys Lys Ser
            260                 265                 270

Gly Val Leu Gly Val Ser Gly Leu Ser Asn Asp Phe Arg Asp Leu Asp
        275                 280                 285

Glu Ala Ala Ser Lys Gly Asn Arg Lys Ala Glu Leu Ala Leu Glu Ile
    290                 295                 300

Phe Ala Tyr Lys Val Lys Lys Phe Ile Gly Glu Tyr Ser Ala Val Leu
305                 310                 315                 320

Asn Gly Ala Asp Ala Val Val Phe Thr Ala Gly Ile Gly Glu Asn Ser
                325                 330                 335

Ala Ser Ile Arg Lys Arg Ile Leu Thr Gly Leu Asp Gly Ile Gly Ile
            340                 345                 350

Lys Ile Asp Asp Glu Lys Asn Lys Ile Arg Gly Gln Glu Ile Asp Ile
        355                 360                 365

Ser Thr Pro Asp Ala Lys Val Arg Val Phe Val Ile Pro Thr Asn Glu
    370                 375                 380

Glu Leu Ala Ile Ala Arg Glu Thr Lys Glu Ile Val Glu Thr Glu Val
385                 390                 395                 400

Lys Leu Arg Ser Ser Ile Pro Val
                405


<210> SEQ ID NO 26
<211> LENGTH: 585
<212> TYPE: DNA
<213> ORGANISM: Sulfolobus acidocaldarius

<400> SEQUENCE: 26

atgaagattg gtattgtaac tggaattcct ggtgtaggga aaagtactgt cttggctaaa     60

gttaaagaga tattggataa tcaaggtata aataacaaga tcataaatta tggagatttt    120

atgttagcaa cagcattaaa attaggctat gctaaagata gagacgaaat gagaaaatta    180

tctgtagaaa agcagaagaa attgcagatt gatgcggcta aaggtatagc tgaagaggca    240

agagcaggtg gagaaggata tctgttcata gatacgcatg ctgtgatacg tacaccctct    300

ggatatttac ctggtttacc gtcatatgta attacagaaa taaatccgtc tgttatcttt    360

ttactggaag ctgatcctaa gataatatta tcaaggcaaa agagagatac aacaaggaat    420

agaaatgatt atagtgacga atcagttata ttagaaacca taaacttcgc tagatatgca    480

gctactgctt ctgcagtatt agccggttct actgttaagg taattgtaaa cgtggaagga    540

gatcctagta tagcagctaa tgagataata aggtctatga agtaa                    585


<210> SEQ ID NO 27
<211> LENGTH: 585
<212> TYPE: DNA
<213> ORGANISM: Artificial Sequence
<220> FEATURE:
<223> OTHER INFORMATION: Synthetic

<400> SEQUENCE: 27

atgaaaatcg gtatcgttac cggtatcccg ggtgttggta aatctaccgt tctggctaaa     60

gttaaagaaa tcctggacaa ccagggtatc aacaacaaaa tcatcaacta cggtgacttc    120

atgctggcta ccgctctgaa actgggttac gctaaagacc gtgacgaaat gcgtaaactg    180

tctgttgaaa aacagaaaaa actgcagatc gacgctgcta aaggtatcgc tgaagaagct    240

cgtgctggtg gtgaaggtta cctgttcatc gacacccacg ctgttatccg taccccgtct    300
```

ggttacctgc cgggtctgcc gtcttacgtt atcaccgaaa tcaacccgtc tgttatcttc 360
ctgctggaag ctgacccgaa aatcatcctg tctcgtcaga aacgtgacac cacccgtaac 420
cgtaacgact actctgacga atctgttatc ctggaaacca tcaacttcgc tcgttacgct 480
gctaccgctt ctgctgttct ggctggttct accgttaaag ttatcgttaa cgttgaaggt 540
gacccgtcta tcgctgctaa cgaaatcatc cgttctatga aatag 585

<210> SEQ ID NO 28
<211> LENGTH: 663
<212> TYPE: DNA
<213> ORGANISM: Thermotoga maritima

<400> SEQUENCE: 28
atgatggcgt accttgtctt tctaggacct ccaggtgcag gaaaaggaac ctacgcaaag 60
agattgcagg aaataacggg gattcctcat atatccaccg gtgacatttt cagggacatt 120
gtaaaaaaag agaacgacga gcttgggaaa aagataaaag agatcatgga aaggggagaa 180
ctcgttccgg acgaactcgt gaacgaggtt gtgaaaagaa gactctcaga aaaagattgt 240
gaaagaggat tcatactgga cggctatcca agaaccgttg ctcaggcgga attcctcgac 300
ggctttttga aaactcaaaa caaagagctc acggctgctg tactctttga agttcctgag 360
gaagtggtcg ttcagaggct cacggccaga aggatctgcc cgaaatgtgg aagaatttac 420
aatttgattt cgctccctcc aaaagaagac gaactgtgcg atgattgtaa agtgaagctc 480
gttcagagag aagacgacaa agaagaaaca gtgagacaca gatacaaggt ttatctcgaa 540
aagacacagc cagtgattga ttactacgat aaaaagggca ttctcaaacg agtggatggt 600
accataggaa tagacaacgt gatcgctgaa gtgttaaaga taatagggtg gagtgataaa 660
tga 663

<210> SEQ ID NO 29
<211> LENGTH: 660
<212> TYPE: DNA
<213> ORGANISM: Artificial Sequence
<220> FEATURE:
<223> OTHER INFORMATION: Synthetic

<400> SEQUENCE: 29
atgatggcct atctggtttt tcttggtcca ccgggggcag gcaaaggtac atatgcgaaa 60
cgtttacagg aaatcaccgg catcccgcac attagcacgg gcgacatttt tcgtgatatt 120
gtcaaaaagg aaaatgacga attaggtaag aaaattaaag aaattatgga gcgcggcgag 180
ttggtgccgg acgaactggt gaatgaagtt gtcaaacgtc ggctgtctga aaaggattgc 240
gaacgtggct ttattttgga cggttacccg cgtacagtag ctcaggcaga gtttctcgac 300
ggcttcctga agactcagaa taaggagtta acggctgcgg tcctgttcga ggtgcctgaa 360
gaggtggtcg ttcagcgtct gaccgcgcgg cgtatctgcc cgaagtgtgg tcgtatttac 420
aacctgattt cacttcctcc aaaagaagat gaactgtgtg atgactgcaa agtaaaactg 480
gtgcaacgcg aagatgataa agaggaaact gtgcgccatc gctacaaagt atatctggaa 540
aaaacccaac cggttatcga ttattatgat aaaaaaggca ttttgaaacg cgttgatggg 600
accatcggca tcgataacgt gattgccgaa gttctcaaaa tcattgggtg gagtgataaa 660

<210> SEQ ID NO 30
<211> LENGTH: 651
<212> TYPE: DNA

<213> ORGANISM: Artificial Sequence
<220> FEATURE:
<223> OTHER INFORMATION: Synthetic

<400> SEQUENCE: 30

```
atgaacctga ttttcctggg tccgcctggg gcaggcaaag gcacccaggc gaaacgtgtg     60

tctgaaaagt acggtatccc gcagattagt accggcgata tgctgcgtga agcggttgct    120

aagggtacgg aactggggaa aaaggcgaaa gaatatatgg acaaagggga acttgttccg    180

gatgaagtag ttattggaat cgtgaaagaa cgcctccagc aaccggattg tgagaagggc    240

tttattctgg acggttttcc gcgtacgtta gcacaagccg aagctctgga cgaaatgtta    300

aaagaattga ataagaaaat tgacgccgta atcaacgtgg tcgtaccgga agaggaagtt    360

gtcaagcgta ttacctatcg tcgcacttgc cgcaattgcg gcgccgtgta ccatctcatt    420

tatgcacctc caaaagagga taataaatgt gataaatgcg gcggtgagct ttatcagcgt    480

gatgacgata aagaagagac agtccgcgag cgttaccgtg tgtataaaca gaacacagag    540

ccattgatcg attattaccg taaaaaggga atcctgtatg atgtggatgg tactaaagac    600

atcgaaggag tttggaaaga aattgaggcg attctggaaa aaattaaaag c             651
```

<210> SEQ ID NO 31
<211> LENGTH: 194
<212> TYPE: PRT
<213> ORGANISM: Sulfolobus acidocaldarius

<400> SEQUENCE: 31

```
Met Lys Ile Gly Ile Val Thr Gly Ile Pro Gly Val Gly Lys Ser Thr
1               5                   10                  15

Val Leu Ala Lys Val Lys Glu Ile Leu Asp Asn Gln Gly Ile Asn Asn
            20                  25                  30

Lys Ile Ile Asn Tyr Gly Asp Phe Met Leu Ala Thr Ala Leu Lys Leu
        35                  40                  45

Gly Tyr Ala Lys Asp Arg Asp Glu Met Arg Lys Leu Ser Val Glu Lys
    50                  55                  60

Gln Lys Lys Leu Gln Ile Asp Ala Ala Lys Gly Ile Ala Glu Glu Ala
65                  70                  75                  80

Arg Ala Gly Gly Glu Gly Tyr Leu Phe Ile Asp Thr His Ala Val Ile
                85                  90                  95

Arg Thr Pro Ser Gly Tyr Leu Pro Gly Leu Pro Ser Tyr Val Ile Thr
            100                 105                 110

Glu Ile Asn Pro Ser Val Ile Phe Leu Leu Glu Ala Asp Pro Lys Ile
        115                 120                 125

Ile Leu Ser Arg Gln Lys Arg Asp Thr Thr Arg Asn Arg Asn Asp Tyr
    130                 135                 140

Ser Asp Glu Ser Val Ile Leu Glu Thr Ile Asn Phe Ala Arg Tyr Ala
145                 150                 155                 160

Ala Thr Ala Ser Ala Val Leu Ala Gly Ser Thr Val Lys Val Ile Val
                165                 170                 175

Asn Val Glu Gly Asp Pro Ser Ile Ala Ala Asn Glu Ile Ile Arg Ser
            180                 185                 190

Met Lys
```

<210> SEQ ID NO 32
<211> LENGTH: 220
<212> TYPE: PRT
<213> ORGANISM: Thermotoga maritima

<400> SEQUENCE: 32

Met Met Ala Tyr Leu Val Phe Leu Gly Pro Pro Gly Ala Gly Lys Gly
1 5 10 15

Thr Tyr Ala Lys Arg Leu Gln Glu Ile Thr Gly Ile Pro His Ile Ser
20 25 30

Thr Gly Asp Ile Phe Arg Asp Ile Val Lys Lys Glu Asn Asp Glu Leu
35 40 45

Gly Lys Lys Ile Lys Glu Ile Met Glu Arg Gly Glu Leu Val Pro Asp
50 55 60

Glu Leu Val Asn Glu Val Val Lys Arg Arg Leu Ser Glu Lys Asp Cys
65 70 75 80

Glu Arg Gly Phe Ile Leu Asp Gly Tyr Pro Arg Thr Val Ala Gln Ala
85 90 95

Glu Phe Leu Asp Gly Phe Leu Lys Thr Gln Asn Lys Glu Leu Thr Ala
100 105 110

Ala Val Leu Phe Glu Val Pro Glu Glu Val Val Val Gln Arg Leu Thr
115 120 125

Ala Arg Arg Ile Cys Pro Lys Cys Gly Arg Ile Tyr Asn Leu Ile Ser
130 135 140

Leu Pro Pro Lys Glu Asp Glu Leu Cys Asp Asp Cys Lys Val Lys Leu
145 150 155 160

Val Gln Arg Glu Asp Asp Lys Glu Glu Thr Val Arg His Arg Tyr Lys
165 170 175

Val Tyr Leu Glu Lys Thr Gln Pro Val Ile Asp Tyr Tyr Asp Lys Lys
180 185 190

Gly Ile Leu Lys Arg Val Asp Gly Thr Ile Gly Ile Asp Asn Val Ile
195 200 205

Ala Glu Val Leu Lys Ile Ile Gly Trp Ser Asp Lys
210 215 220

<210> SEQ ID NO 33
<211> LENGTH: 11
<212> TYPE: PRT
<213> ORGANISM: Artificial Sequence
<220> FEATURE:
<223> OTHER INFORMATION: transglutaminase substrate

<400> SEQUENCE: 33

Met Asn Gln Glu Gln Val Ser Pro Leu Gly Gly
1 5 10

<210> SEQ ID NO 34
<211> LENGTH: 204
<212> TYPE: PRT
<213> ORGANISM: Artificial Sequence
<220> FEATURE:
<223> OTHER INFORMATION: Protein sequence of thermostable adenylate kinase from Sulfolobus acidcaldarius fused at the N-terminus with a transglutaminase (Factor XIII) substrate sequence

<400> SEQUENCE: 34

Met Asn Gln Glu Gln Val Ser Pro Leu Gly Gly Lys Ile Gly Ile Val
1 5 10 15

Thr Gly Ile Pro Gly Val Gly Lys Ser Thr Val Leu Ala Lys Val Lys
20 25 30

Glu Ile Leu Asp Asn Gln Gly Ile Asn Asn Lys Ile Ile Asn Tyr Gly
35 40 45

```
Asp Phe Met Leu Ala Thr Ala Leu Lys Leu Gly Tyr Ala Lys Asp Arg
    50                  55                  60

Asp Glu Met Arg Lys Leu Ser Val Glu Lys Gln Lys Lys Leu Gln Ile
65                  70                  75                  80

Asp Ala Ala Lys Gly Ile Ala Glu Glu Ala Arg Ala Gly Gly Glu Gly
                85                  90                  95

Tyr Leu Phe Ile Asp Thr His Ala Val Ile Arg Thr Pro Ser Gly Tyr
            100                 105                 110

Leu Pro Gly Leu Pro Ser Tyr Val Ile Thr Glu Ile Asn Pro Ser Val
        115                 120                 125

Ile Phe Leu Leu Glu Ala Asp Pro Lys Ile Ile Leu Ser Arg Gln Lys
    130                 135                 140

Arg Asp Thr Thr Arg Asn Arg Asn Asp Tyr Ser Asp Glu Ser Val Ile
145                 150                 155                 160

Leu Glu Thr Ile Asn Phe Ala Arg Tyr Ala Ala Thr Ala Ser Ala Val
                165                 170                 175

Leu Ala Gly Ser Thr Val Lys Val Ile Val Asn Val Glu Gly Asp Pro
            180                 185                 190

Ser Ile Ala Ala Asn Glu Ile Ile Arg Ser Met Lys
        195                 200


<210> SEQ ID NO 35
<211> LENGTH: 204
<212> TYPE: PRT
<213> ORGANISM: Artificial Sequence
<220> FEATURE:
<223> OTHER INFORMATION: Protein sequence of thermostable adenylate
      kinase from Sulfolobus acidcaldarius fused at the C-terminus with
      a transglutaminase (factor VIII) substrate sequence

<400> SEQUENCE: 35

Met Lys Ile Gly Ile Val Thr Gly Ile Pro Gly Val Gly Lys Ser Thr
1               5                   10                  15

Val Leu Ala Lys Val Lys Glu Ile Leu Asp Asn Gln Gly Ile Asn Asn
            20                  25                  30

Lys Ile Ile Asn Tyr Gly Asp Phe Met Leu Ala Thr Ala Leu Lys Leu
        35                  40                  45

Gly Tyr Ala Lys Asp Arg Asp Glu Met Arg Lys Leu Ser Val Glu Lys
    50                  55                  60

Gln Lys Lys Leu Gln Ile Asp Ala Ala Lys Gly Ile Ala Glu Glu Ala
65                  70                  75                  80

Arg Ala Gly Gly Glu Gly Tyr Leu Phe Ile Asp Thr His Ala Val Ile
                85                  90                  95

Arg Thr Pro Ser Gly Tyr Leu Pro Gly Leu Pro Ser Tyr Val Ile Thr
            100                 105                 110

Glu Ile Asn Pro Ser Val Ile Phe Leu Leu Glu Ala Asp Pro Lys Ile
        115                 120                 125

Ile Leu Ser Arg Gln Lys Arg Asp Thr Thr Arg Asn Arg Asn Asp Tyr
    130                 135                 140

Ser Asp Glu Ser Val Ile Leu Glu Thr Ile Asn Phe Ala Arg Tyr Ala
145                 150                 155                 160

Ala Thr Ala Ser Ala Val Leu Ala Gly Ser Thr Val Lys Val Ile Val
                165                 170                 175

Asn Val Glu Gly Asp Pro Ser Ile Ala Ala Asn Glu Ile Ile Arg Ser
            180                 185                 190

Met Lys Gly Gly Asn Gln Glu Gln Val Ser Pro Leu
```

195 200

<210> SEQ ID NO 36
<211> LENGTH: 214
<212> TYPE: PRT
<213> ORGANISM: Artificial Sequence
<220> FEATURE:
<223> OTHER INFORMATION: Protein sequence of thermostable adenylate kinase from Sulfolobus acidcaldarius fused at the N-terminus and C-terminus with a transglutaminase (Factor XIII) substrate sequence

<400> SEQUENCE: 36

Met Asn Gln Glu Gln Val Ser Pro Leu Gly Gly Lys Ile Gly Ile Val
1 5 10 15

Thr Gly Ile Pro Gly Val Gly Lys Ser Thr Val Leu Ala Lys Val Lys
20 25 30

Glu Ile Leu Asp Asn Gln Gly Ile Asn Asn Lys Ile Ile Asn Tyr Gly
35 40 45

Asp Phe Met Leu Ala Thr Ala Leu Lys Leu Gly Tyr Ala Lys Asp Arg
50 55 60

Asp Glu Met Arg Lys Leu Ser Val Glu Lys Gln Lys Lys Leu Gln Ile
65 70 75 80

Asp Ala Ala Lys Gly Ile Ala Glu Glu Ala Arg Ala Gly Gly Glu Gly
85 90 95

Tyr Leu Phe Ile Asp Thr His Ala Val Ile Arg Thr Pro Ser Gly Tyr
100 105 110

Leu Pro Gly Leu Pro Ser Tyr Val Ile Thr Glu Ile Asn Pro Ser Val
115 120 125

Ile Phe Leu Leu Glu Ala Asp Pro Lys Ile Ile Leu Ser Arg Gln Lys
130 135 140

Arg Asp Thr Thr Arg Asn Arg Asn Asp Tyr Ser Asp Glu Ser Val Ile
145 150 155 160

Leu Glu Thr Ile Asn Phe Ala Arg Tyr Ala Ala Thr Ala Ser Ala Val
165 170 175

Leu Ala Gly Ser Thr Val Lys Val Ile Val Asn Val Glu Gly Asp Pro
180 185 190

Ser Ile Ala Ala Asn Glu Ile Ile Arg Ser Met Lys Gly Gly Asn Gln
195 200 205

Glu Gln Val Ser Pro Leu
210

<210> SEQ ID NO 37
<211> LENGTH: 704
<212> TYPE: DNA
<213> ORGANISM: Artificial Sequence
<220> FEATURE:
<223> OTHER INFORMATION: DNA sequence of transglutaminase (Factor XIII) substrate sequence fused to the 5' end of adenylate kinase from Thermotoga maritima.

<400> SEQUENCE: 37
atgaatcaag aacaagtcag cccgctgggc ggcatcatcg cctatctggt ttttcttggt 60
ccaccggggg caggcaaagg tacctatgcg aaacgtttac aggaaatcac cggcatcccg 120
cacattagca cgggcgacat ttttcgtgat attgtcaaaa aggaaaatga cgaattaggt 180
aagaaaatta aagaaattat ggagcgcggc gagttggtgc cggacgaact ggtgaatgaa 240
gttgtcaaac gtcggctgtc tgaaaaggat tgcgaacgtg gctttatttt ggacggttac 300

-continued ccgcgtacag tagctcaggc agagtttctc gacggcttcc tgaagactca gaataaggag 360
ttaacggctg cggtcctgtt cgaggtgcct gaagaggtgg tcgttcagcg tctgaccgcg 420
cggcgtatct gcccgaagtg tggtcgtatt tacaacctga tttcacttcc tccaaaagaa 480
gatgaactgt gtgatgactg caaagtaaaa ctggtgcaac gcgaagatga taaagaggaa 540
actgtgcgcc atcgctacaa agtatatctg gaaaaaaccc aaccggttat cgattattat 600
gataaaaaag gcattttgaa acgcgttgat gggaccatcg gcatcgataa cgtgattgcc 660
gaagttctca aaatcattgg gtggagtgat aaataggtcg acgc 704

<210> SEQ ID NO 38
<211> LENGTH: 231
<212> TYPE: PRT
<213> ORGANISM: Artificial Sequence
<220> FEATURE:
<223> OTHER INFORMATION: Protein sequence of adenylate kinase from Thermotoga maritime fused at the N-terminal with a transglutaminase (Factor XIII) substrate sequence.

<400> SEQUENCE: 38

Met Asn Gln Glu Gln Val Ser Pro Leu Gly Gly Ile Ile Ala Tyr Leu
1 5 10 15

Val Phe Leu Gly Pro Pro Gly Ala Gly Lys Gly Thr Tyr Ala Lys Arg
20 25 30

Leu Gln Glu Ile Thr Gly Ile Pro His Ile Ser Thr Gly Asp Ile Phe
35 40 45

Arg Asp Ile Val Lys Lys Glu Asn Asp Glu Leu Gly Lys Lys Ile Lys
50 55 60

Glu Ile Met Glu Arg Gly Glu Leu Val Pro Asp Glu Leu Val Asn Glu
65 70 75 80

Val Val Lys Arg Arg Leu Ser Glu Lys Asp Cys Glu Arg Gly Phe Ile
85 90 95

Leu Asp Gly Tyr Pro Arg Thr Val Ala Gln Ala Glu Phe Leu Asp Gly
100 105 110

Phe Leu Lys Thr Gln Asn Lys Glu Leu Thr Ala Ala Val Leu Phe Glu
115 120 125

Val Pro Glu Glu Val Val Val Gln Arg Leu Thr Ala Arg Arg Ile Cys
130 135 140

Pro Lys Cys Gly Arg Ile Tyr Asn Leu Ile Ser Leu Pro Pro Lys Glu
145 150 155 160

Asp Glu Leu Cys Asp Asp Cys Lys Val Lys Leu Val Gln Arg Glu Asp
165 170 175

Asp Lys Glu Glu Thr Val Arg His Arg Tyr Lys Val Tyr Leu Glu Lys
180 185 190

Thr Gln Pro Val Ile Asp Tyr Tyr Asp Lys Lys Gly Ile Leu Lys Arg
195 200 205

Val Asp Gly Thr Ile Gly Ile Asp Asn Val Ile Ala Glu Val Leu Lys
210 215 220

Ile Ile Gly Trp Ser Asp Lys
225 230

<210> SEQ ID NO 39
<211> LENGTH: 696
<212> TYPE: DNA
<213> ORGANISM: Artificial Sequence
<220> FEATURE:
<223> OTHER INFORMATION: DNA sequence of transglutaminase (Factor XIII) substrate sequence fused to the 3' end of adenylate kinase from Thermotoga maritima.

<400> SEQUENCE: 39

```
atgatggcct atctggtttt tcttggtcca ccgggggcag gcaaaggtac ctatgcgaaa      60
cgtttacagg aaatcaccgg catcccgcac attagcacgg gcgacatttt tcgtgatatt     120
gtcaaaaagg aaaatgacga attaggtaag aaaattaaag aaattatgga gcgcggcgag     180
ttggtgccgg acgaactggt gaatgaagtt gtcaaacgtc ggctgtctga aaaggattgc     240
gaacgtggct ttattttgga cggttacccg cgtacagtag ctcaggcaga gtttctcgac     300
ggcttcctga agactcagaa taaggagtta acggctgcgg tcctgttcga ggtgcctgaa     360
gaggtggtcg ttcagcgtct gaccgcgcgg cgtatctgcc cgaagtgtgg tcgtatttac     420
aacctgattt cacttcctcc aaaagaagat gaactgtgtg atgactgcaa agtaaaactg     480
gtgcaacgcg aagatgataa agaggaaact gtgcgccatc gctacaaagt atatctggaa     540
aaaacccaac cggttatcga ttattatgat aaaaaaggca ttttgaaacg cgttgatggg     600
accatcggca tcgataacgt gattgccgaa gttctcaaaa tcattgggtg gagtgataaa     660
ctgggcggca atcaagaaca agtcagcccg ctgtaa                               696
```

<210> SEQ ID NO 40
<211> LENGTH: 231
<212> TYPE: PRT
<213> ORGANISM: Artificial Sequence
<220> FEATURE:
<223> OTHER INFORMATION: Protein sequence of adenylate kinase from Thermotoga maritime fused at the C-terminal with a transglutaminase (Factor XIII) substrate sequence.

<400> SEQUENCE: 40

```
Met Met Ala Tyr Leu Val Phe Leu Gly Pro Pro Gly Ala Gly Lys Gly
1               5                   10                  15

Thr Tyr Ala Lys Arg Leu Gln Glu Ile Thr Gly Ile Pro His Ile Ser
            20                  25                  30

Thr Gly Asp Ile Phe Arg Asp Ile Val Lys Lys Glu Asn Asp Glu Leu
        35                  40                  45

Gly Lys Lys Ile Lys Glu Ile Met Glu Arg Gly Glu Leu Val Pro Asp
    50                  55                  60

Glu Leu Val Asn Glu Val Val Lys Arg Arg Leu Ser Glu Lys Asp Cys
65                  70                  75                  80

Glu Arg Gly Phe Ile Leu Asp Gly Tyr Pro Arg Thr Val Ala Gln Ala
                85                  90                  95

Glu Phe Leu Asp Gly Phe Leu Lys Thr Gln Asn Lys Glu Leu Thr Ala
            100                 105                 110

Ala Val Leu Phe Glu Val Pro Glu Glu Val Val Val Gln Arg Leu Thr
        115                 120                 125

Ala Arg Arg Ile Cys Pro Lys Cys Gly Arg Ile Tyr Asn Leu Ile Ser
    130                 135                 140

Leu Pro Pro Lys Glu Asp Glu Leu Cys Asp Asp Cys Lys Val Lys Leu
145                 150                 155                 160

Val Gln Arg Glu Asp Asp Lys Glu Glu Thr Val Arg His Arg Tyr Lys
                165                 170                 175

Val Tyr Leu Glu Lys Thr Gln Pro Val Ile Asp Tyr Tyr Asp Lys Lys
            180                 185                 190

Gly Ile Leu Lys Arg Val Asp Gly Thr Ile Gly Ile Asp Asn Val Ile
        195                 200                 205
```

Ala Glu Val Leu Lys Ile Ile Gly Trp Ser Asp Lys Leu Gly Gly Asn
    210                 215                 220

Gln Glu Gln Val Ser Pro Leu
225                 230

<210> SEQ ID NO 41
<211> LENGTH: 729
<212> TYPE: DNA
<213> ORGANISM: Artificial Sequence
<220> FEATURE:
<223> OTHER INFORMATION: DNA sequence of transglutaminase (Factor XIII) substrate sequence fused to both the 5' and 3' ends of adenylate kinase from Thermotoga maritima.

<400> SEQUENCE: 41
atgaatcaag aacaagtcag cccgctgggc ggcatcatcg cctatctggt ttttcttggt 60
ccaccggggg caggcaaagg tacctatgcg aaacgtttac aggaaatcac cggcatcccg 120
cacattagca cgggcgacat ttttcgtgat attgtcaaaa aggaaaatga cgaattaggt 180
aagaaaatta aagaaattat ggagcgcggc gagttggtgc cggacgaact ggtgaatgaa 240
gttgtcaaac gtcggctgtc tgaaaaggat tgcgaacgtg gctttatttt ggacggttac 300
ccgcgtacag tagctcaggc agagtttctc gacggcttcc tgaagactca gaataaggag 360
ttaacggctg cggtcctgtt cgaggtgcct gaagaggtgg tcgttcagcg tctgaccgcg 420
cggcgtatct gcccgaagtg tggtcgtatt tacaacctga tttcacttcc tccaaaagaa 480
gatgaactgt gtgatgactg caaagtaaaa ctggtgcaac gcgaagatga taaagaggaa 540
actgtgcgcc atcgctacaa agtatatctg gaaaaaaccc aaccggttat cgattattat 600
gataaaaaag gcattttgaa acgcgttgat gggaccatcg gcatcgataa cgtgattgcc 660
gaagttctca aaatcattgg gtggagtgat aaactgggcg gcaatcaaga acaagtcagc 720
ccgctgtaa 729

<210> SEQ ID NO 42
<211> LENGTH: 242
<212> TYPE: PRT
<213> ORGANISM: Artificial Sequence
<220> FEATURE:
<223> OTHER INFORMATION: Protein sequence of adenylate kinase from Thermotoga maritime fused at the N- and C-terminal with a transglutaminase (Factor XIII) substrate sequence.

<400> SEQUENCE: 42

Met Asn Gln Glu Gln Val Ser Pro Leu Gly Gly Ile Ile Ala Tyr Leu
1               5                   10                  15

Val Phe Leu Gly Pro Pro Gly Ala Gly Lys Gly Thr Tyr Ala Lys Arg
            20                  25                  30

Leu Gln Glu Ile Thr Gly Ile Pro His Ile Ser Thr Gly Asp Ile Phe
        35                  40                  45

Arg Asp Ile Val Lys Lys Glu Asn Asp Glu Leu Gly Lys Lys Ile Lys
    50                  55                  60

Glu Ile Met Glu Arg Gly Glu Leu Val Pro Asp Glu Leu Val Asn Glu
65                  70                  75                  80

Val Val Lys Arg Arg Leu Ser Glu Lys Asp Cys Glu Arg Gly Phe Ile
                85                  90                  95

Leu Asp Gly Tyr Pro Arg Thr Val Ala Gln Ala Glu Phe Leu Asp Gly
            100                 105                 110

Phe Leu Lys Thr Gln Asn Lys Glu Leu Thr Ala Ala Val Leu Phe Glu
        115                 120                 125

```
Val Pro Glu Glu Val Val Val Gln Arg Leu Thr Ala Arg Arg Ile Cys
    130                 135                 140

Pro Lys Cys Gly Arg Ile Tyr Asn Leu Ile Ser Leu Pro Pro Lys Glu
145                 150                 155                 160

Asp Glu Leu Cys Asp Asp Cys Lys Val Lys Leu Val Gln Arg Glu Asp
                165                 170                 175

Asp Lys Glu Glu Thr Val Arg His Arg Tyr Lys Val Tyr Leu Glu Lys
            180                 185                 190

Thr Gln Pro Val Ile Asp Tyr Tyr Asp Lys Lys Gly Ile Leu Lys Arg
        195                 200                 205

Val Asp Gly Thr Ile Gly Ile Asp Asn Val Ile Ala Glu Val Leu Lys
    210                 215                 220

Ile Ile Gly Trp Ser Asp Lys Leu Gly Gly Asn Gln Glu Gln Val Ser
225                 230                 235                 240

Pro Leu
```

<210> SEQ ID NO 43
<211> LENGTH: 1288
<212> TYPE: DNA
<213> ORGANISM: Artificial Sequence
<220> FEATURE:
<223> OTHER INFORMATION: DNA sequence of complete Sup35 gene construct from Saccharomyces cerevisiae

<400> SEQUENCE: 43

```
gattcaaacc aaggcaacaa tcagcaaaac taccagcaat acagccagaa cggtaaccaa     60

caacaaggta acaacagata ccaaggttat caagcttaca atgctcaagc ccaacctggg    120

ggtgggtact accaaaatta ccaaggttat tctgggtacc aacaaggtgg ctatcaacag    180

tacaatcccg acgccggtta ccagcaacag tataatcctc aaggaggcta tcaacagtac    240

aatcctcaag gcggttatca gcaccaattc aatccacaag gtggccgtgg aaattacaaa    300

aacttcaact acaataacaa tttgcaagga tatcaagctg gtttccaacc acagtctcaa    360

ggtatgtctt tgaacgactt tcaaaagcaa caaaagcagg ccgctcccaa accaaagaag    420

actttgaagc ttgtctccag ttcctgtatc aagttggcca atgctaccaa gaaggttgac    480

acaaaacctg ccgaatctga taagaaagag gaagagaagt ctgctgaaac caaagaacca    540

actaaagagc caacaaaggt cgaagaacca gttaaaaagg aggagaaacc agtccagact    600

gaagaaaaga cggaggaaaa atcggaactt ccaaaggtag aagaccttaa aatctctgaa    660

tcaacacata ataccaacaa tgccaatgtt accagtgctg atgccttgat caaggaacag    720

gaagaagaag tggatgacga agttgttaac gatatgtttg gtggtaaaga tcacgtttct    780

ttaattttca tgggtcatgt tgatgccggt aaatctacta tgggtggtaa tctactatac    840

ttgactggct ctgtggataa gagaactatt gagaaatatg aaagagaagc caaggatgca    900

ggcagacaag gttggtactt gtcatgggtc atggatacca acaaagaaga aagaaatgat    960

ggtaagacta tcgaagttgg taaggcctac tttgaaactg aaaaaaggcg ttataccata   1020

ttggatgctc ctggtcataa aatgtacgtt tccgagatga tcggtggtgc ttctcaagct   1080

gatgttggtg ttttggtcat ttccgccaga aagggtgagt acgaaaccgg ttttgagaga   1140

ggtggtcaaa ctcgtgaaca cgccctattg gccaagaccc aaggtgttaa taagatggtt   1200

gtcgtcgtaa ataagatgga tgacccaacc gttaactggt ctaaggaacg ttacgaccaa   1260

tgtgtgagta atgtcagcaa tttcttga                                      1288
```

<210> SEQ ID NO 44
<211> LENGTH: 429
<212> TYPE: PRT
<213> ORGANISM: Artificial Sequence
<220> FEATURE:
<223> OTHER INFORMATION: Protein sequence of complete Sup35 from
Saccharomyces cerevisiae

<400> SEQUENCE: 44

Asp Ser Asn Gln Gly Asn Asn Gln Gln Asn Tyr Gln Gln Tyr Ser Gln
1 5 10 15

Asn Gly Asn Gln Gln Gln Gly Asn Asn Arg Tyr Gln Gly Tyr Gln Ala
20 25 30

Tyr Asn Ala Gln Ala Gln Pro Gly Gly Gly Tyr Tyr Gln Asn Tyr Gln
35 40 45

Gly Tyr Ser Gly Tyr Gln Gln Gly Gly Tyr Gln Gln Tyr Asn Pro Asp
50 55 60

Ala Gly Tyr Gln Gln Gln Tyr Asn Pro Gln Gly Gly Tyr Gln Gln Tyr
65 70 75 80

Asn Pro Gln Gly Gly Tyr Gln His Gln Phe Asn Pro Gln Gly Gly Arg
85 90 95

Gly Asn Tyr Lys Asn Phe Asn Tyr Asn Asn Asn Leu Gln Gly Tyr Gln
100 105 110

Ala Gly Phe Gln Pro Gln Ser Gln Gly Met Ser Leu Asn Asp Phe Gln
115 120 125

Lys Gln Gln Lys Gln Ala Ala Pro Lys Pro Lys Lys Thr Leu Lys Leu
130 135 140

Val Ser Ser Ser Cys Ile Lys Leu Ala Asn Ala Thr Lys Lys Val Asp
145 150 155 160

Thr Lys Pro Ala Glu Ser Asp Lys Lys Glu Glu Glu Lys Ser Ala Glu
165 170 175

Thr Lys Glu Pro Thr Lys Glu Pro Thr Lys Val Glu Glu Pro Val Lys
180 185 190

Lys Glu Glu Lys Pro Val Gln Thr Glu Glu Lys Thr Glu Glu Lys Ser
195 200 205

Glu Leu Pro Lys Val Glu Asp Leu Lys Ile Ser Glu Ser Thr His Asn
210 215 220

Thr Asn Asn Ala Asn Val Thr Ser Ala Asp Ala Leu Ile Lys Glu Gln
225 230 235 240

Glu Glu Glu Val Asp Asp Glu Val Val Asn Asp Met Phe Gly Gly Lys
245 250 255

Asp His Val Ser Leu Ile Phe Met Gly His Val Asp Ala Gly Lys Ser
260 265 270

Thr Met Gly Gly Asn Leu Leu Tyr Leu Thr Gly Ser Val Asp Lys Arg
275 280 285

Thr Ile Glu Lys Tyr Glu Arg Glu Ala Lys Asp Ala Gly Arg Gln Gly
290 295 300

Trp Tyr Leu Ser Trp Val Met Asp Thr Asn Lys Glu Glu Arg Asn Asp
305 310 315 320

Gly Lys Thr Ile Glu Val Gly Lys Ala Tyr Phe Glu Thr Glu Lys Arg
325 330 335

Arg Tyr Thr Ile Leu Asp Ala Pro Gly His Lys Met Tyr Val Ser Glu
340 345 350

Met Ile Gly Gly Ala Ser Gln Ala Asp Val Gly Val Leu Val Ile Ser
355 360 365

```
Ala Arg Lys Gly Glu Tyr Glu Thr Gly Phe Glu Arg Gly Gly Gln Thr
    370                 375                 380

Arg Glu His Ala Leu Leu Ala Lys Thr Gln Gly Val Asn Lys Met Val
385                 390                 395                 400

Val Val Val Asn Lys Met Asp Asp Pro Thr Val Asn Trp Ser Lys Glu
                405                 410                 415

Arg Tyr Asp Gln Cys Val Ser Asn Val Ser Asn Phe Leu
            420                 425


<210> SEQ ID NO 45
<211> LENGTH: 348
<212> TYPE: DNA
<213> ORGANISM: Artificial Sequence
<220> FEATURE:
<223> OTHER INFORMATION: DNA sequence of sup35N (N-terminal domain)
      codon-biased for optimal expression in E. coli

<400> SEQUENCE: 45

atggactcta accagggtaa caaccagcag aactaccagc agtactctca gaacggtaac      60

cagcagcagg gtaacaaccg ttaccagggt taccaggctt acaacgctca ggctcagccg     120

ggtggtggtt actaccagaa ctaccagggt tactccggat atcaacaggg tggttaccaa     180

caatataatc cagacgctgg ttaccagcag cagtacaacc cgcagggtgg ttaccagcag     240

tacaacccgc aaggcggata tcaacaccag ttcaatccgc agggtggtcg tggtaactac     300

aaaaacttca actacaacaa caacctgcag ggttaccagg ctggttaa                  348


<210> SEQ ID NO 46
<211> LENGTH: 115
<212> TYPE: PRT
<213> ORGANISM: Artificial Sequence
<220> FEATURE:
<223> OTHER INFORMATION: Protein sequence of sup35N (N-terminal domain)

<400> SEQUENCE: 46

Met Asp Ser Asn Gln Gly Asn Asn Gln Gln Asn Tyr Gln Gln Tyr Ser
1               5                   10                  15

Gln Asn Gly Asn Gln Gln Gln Gly Asn Asn Arg Tyr Gln Gly Tyr Gln
            20                  25                  30

Ala Tyr Asn Ala Gln Ala Gln Pro Gly Gly Gly Tyr Tyr Gln Asn Tyr
        35                  40                  45

Gln Gly Tyr Ser Gly Tyr Gln Gln Gly Gly Tyr Gln Gln Tyr Asn Pro
    50                  55                  60

Asp Ala Gly Tyr Gln Gln Gln Tyr Asn Pro Gln Gly Gly Tyr Gln Gln
65                  70                  75                  80

Tyr Asn Pro Gln Gly Gly Tyr Gln His Gln Phe Asn Pro Gln Gly Gly
                85                  90                  95

Arg Gly Asn Tyr Lys Asn Phe Asn Tyr Asn Asn Asn Leu Gln Gly Tyr
            100                 105                 110

Gln Ala Gly
        115


<210> SEQ ID NO 47
<211> LENGTH: 941
<212> TYPE: DNA
<213> ORGANISM: Artificial Sequence
<220> FEATURE:
<223> OTHER INFORMATION: DNA sequence of E-coli codon biased Adenylate
      kinase from Sulfolobus acidcaldarius fused at the N-terminus with
      Sup35 N-terminal domain from Saccharomyces cerevisiae
```

<400> SEQUENCE: 47

```
atggactcta accagggtaa caaccagcag aactaccagc agtactctca gaacggtaac     60
cagcagcagg gtaacaaccg ttaccagggt taccaggctt acaacgctca ggctcagccg    120
ggtggtggtt actaccagaa ctaccagggt tactccggtt atcagcaagg tggctaccaa    180
caatataatc cagacgctgg ctatcaacag caatataatc ctcagggtgg ttaccagcag    240
tacaacccgc aaggcggtta tcaacaccag ttcaatccgc agggtggtcg tggtaactac    300
aaaaacttca actacaacaa caacctgcag ggttaccagg ctggaattat gaagatcggc    360
attgtgaccg gcattccggg cgttggcaaa agcaccgttc tggcaaaggt gaaggagatc    420
ctggacaacc agggcattaa taacaaaatt attaattatg gtgattttat gctggcgacc    480
gcgctgaagc tgggctacgc aaaagatcgt gacgaaatgc gcaaactgag cgtggaaaaa    540
cagaagaagc tgcagattga tgcggcgaag ggcattgcgg aagaggcacg cgcgggcggc    600
gaaggctacc tgtttatcga tacccatgcg gtgatccgca ccccgagcgg ttatctgccg    660
ggcctgccgt cttacgtgat tacggaaatc aacccgagcg ttatttttct gctggaggca    720
gatccgaaga ttattctgag ccgccagaag cgcgatacca cccgcaaccg caacgattat    780
agcgacgaaa gcgttatcct ggagaccatc aactttgcgc gctatgcggc aaccgcgagc    840
gcggttctgg caggctctac cgttaaagtg atcgtgaacg tggagggtga tccaagcatc    900
gcggcgaacg aaatcattcg cagcatgaaa taagtcgacg c                          941
```

<210> SEQ ID NO 48
<211> LENGTH: 310
<212> TYPE: PRT
<213> ORGANISM: Artificial Sequence
<220> FEATURE:
<223> OTHER INFORMATION: Protein sequence of Adenylate kinase from Sulfolobus acidcaldarius fused at the N-terminus with Sup35 N-terminal domain from Saccharomyces cerevisiae

<400> SEQUENCE: 48

```
Met Asp Ser Asn Gln Gly Asn Asn Gln Gln Asn Tyr Gln Gln Tyr Ser
1               5                   10                  15

Gln Asn Gly Asn Gln Gln Gln Gly Asn Asn Arg Tyr Gln Gly Tyr Gln
            20                  25                  30

Ala Tyr Asn Ala Gln Ala Gln Pro Gly Gly Gly Tyr Tyr Gln Asn Tyr
        35                  40                  45

Gln Gly Tyr Ser Gly Tyr Gln Gln Gly Gly Tyr Gln Gln Tyr Asn Pro
    50                  55                  60

Asp Ala Gly Tyr Gln Gln Gln Tyr Asn Pro Gln Gly Gly Tyr Gln Gln
65                  70                  75                  80

Tyr Asn Pro Gln Gly Gly Tyr Gln His Gln Phe Asn Pro Gln Gly Gly
                85                  90                  95

Arg Gly Asn Tyr Lys Asn Phe Asn Tyr Asn Asn Asn Leu Gln Gly Tyr
            100                 105                 110

Gln Ala Gly Ile Met Lys Ile Gly Ile Val Thr Gly Ile Pro Gly Val
        115                 120                 125

Gly Lys Ser Thr Val Leu Ala Lys Val Lys Glu Ile Leu Asp Asn Gln
    130                 135                 140

Gly Ile Asn Asn Lys Ile Ile Asn Tyr Gly Asp Phe Met Leu Ala Thr
145                 150                 155                 160

Ala Leu Lys Leu Gly Tyr Ala Lys Asp Arg Asp Glu Met Arg Lys Leu
                165                 170                 175
```

```
Ser Val Glu Lys Gln Lys Lys Leu Gln Ile Asp Ala Ala Lys Gly Ile
            180                 185                 190

Ala Glu Glu Ala Arg Ala Gly Gly Glu Gly Tyr Leu Phe Ile Asp Thr
        195                 200                 205

His Ala Val Ile Arg Thr Pro Ser Gly Tyr Leu Pro Gly Leu Pro Ser
    210                 215                 220

Tyr Val Ile Thr Glu Ile Asn Pro Ser Val Ile Phe Leu Leu Glu Ala
225                 230                 235                 240

Asp Pro Lys Ile Ile Leu Ser Arg Gln Lys Arg Asp Thr Thr Arg Asn
                245                 250                 255

Arg Asn Asp Tyr Ser Asp Glu Ser Val Ile Leu Glu Thr Ile Asn Phe
            260                 265                 270

Ala Arg Tyr Ala Ala Thr Ala Ser Ala Val Leu Ala Gly Ser Thr Val
        275                 280                 285

Lys Val Ile Val Asn Val Glu Gly Asp Pro Ser Ile Ala Ala Asn Glu
    290                 295                 300

Ile Ile Arg Ser Met Lys
305                 310
```

<210> SEQ ID NO 49
<211> LENGTH: 947
<212> TYPE: DNA
<213> ORGANISM: Artificial Sequence
<220> FEATURE:
<223> OTHER INFORMATION: DNA sequence of E. coli codon biased Adenylate kinase from Sulfolobus acidcaldarius fused at the C-terminus with Sup35 N-terminal domain from Saccharomyces cerevisiae

<400> SEQUENCE: 49

```
atgaagatcg gcattgtgac cggcattccg ggcgttggca aaagcaccgt tctggcaaag     60

gtgaaggaga tcctggacaa ccagggcatt aataacaaaa ttattaatta tggtgatttt    120

atgctggcga ccgcgctgaa gctgggctac gcaaaagatc gtgacgaaat gcgcaaactg    180

agcgtggaaa aacagaagaa gctgcagatt gatgcggcga agggcattgc ggaagaggca    240

cgcgcgggcg gcgaaggcta cctgtttatc gatacccatg cggtgatccg caccccgagc    300

ggttatctgc cgggcctgcc gtcttacgtg attacggaaa tcaacccgag cgttattttt    360

ctgctggagg cagatccgaa gattattctg agccgccaga agcgcgatac cacccgcaac    420

cgcaacgatt atagcgacga aagcgttatc ctggagacca tcaactttgc gcgctatgcg    480

gcaaccgcga gcgcggttct ggcaggctct accgttaaag tgatcgtgaa cgtggagggt    540

gatccaagca tcgcggcgaa cgaaatcatt cgcagcatga aacagtcgag tatggactct    600

aaccagggta acaaccagca gaactaccag cagtactctc agaacggtaa ccagcagcag    660

ggtaacaacc gttaccaggg ttaccaggct tacaacgctc aggctcagcc gggtggtggt    720

tactaccaga actaccaggg ttactccggt tatcagcaag gtggctacca acaatataat    780

ccagacgctg gctatcaaca gcaatataat cctcagggtg gttaccagca gtacaacccg    840

caaggcggtt atcaacacca gttcaatccg cagggtggtc gtggtaacta caaaaacttc    900

aactacaaca acaacctgca gggttaccag gctggttaag tcgacgc                  947
```

<210> SEQ ID NO 50
<211> LENGTH: 312
<212> TYPE: PRT
<213> ORGANISM: Artificial Sequence
<220> FEATURE:
<223> OTHER INFORMATION: Protein sequence of Adenylate kinase from Sulfolobus acidcaldarius fused at the C-terminus with Sup35 N-terminal domain from Saccharomyces cerevisiae

<400> SEQUENCE: 50

```
Met Lys Ile Gly Ile Val Thr Gly Ile Pro Gly Val Gly Lys Ser Thr
1               5                   10                  15

Val Leu Ala Lys Val Lys Glu Ile Leu Asp Asn Gln Gly Ile Asn Asn
            20                  25                  30

Lys Ile Ile Asn Tyr Gly Asp Phe Met Leu Ala Thr Ala Leu Lys Leu
        35                  40                  45

Gly Tyr Ala Lys Asp Arg Asp Glu Met Arg Lys Leu Ser Val Glu Lys
    50                  55                  60

Gln Lys Lys Leu Gln Ile Asp Ala Ala Lys Gly Ile Ala Glu Glu Ala
65                  70                  75                  80

Arg Ala Gly Gly Glu Gly Tyr Leu Phe Ile Asp Thr His Ala Val Ile
                85                  90                  95

Arg Thr Pro Ser Gly Tyr Leu Pro Gly Leu Pro Ser Tyr Val Ile Thr
            100                 105                 110

Glu Ile Asn Pro Ser Val Ile Phe Leu Leu Glu Ala Asp Pro Lys Ile
        115                 120                 125

Ile Leu Ser Arg Gln Lys Arg Asp Thr Thr Arg Asn Arg Asn Asp Tyr
    130                 135                 140

Ser Asp Glu Ser Val Ile Leu Glu Thr Ile Asn Phe Ala Arg Tyr Ala
145                 150                 155                 160

Ala Thr Ala Ser Ala Val Leu Ala Gly Ser Thr Val Lys Val Ile Val
                165                 170                 175

Asn Val Glu Gly Asp Pro Ser Ile Ala Ala Asn Glu Ile Ile Arg Ser
            180                 185                 190

Met Lys Gln Ser Ser Met Asp Ser Asn Gln Gly Asn Asn Gln Gln Asn
        195                 200                 205

Tyr Gln Gln Tyr Ser Gln Asn Gly Asn Gln Gln Gln Gly Asn Asn Arg
    210                 215                 220

Tyr Gln Gly Tyr Gln Ala Tyr Asn Ala Gln Ala Gln Pro Gly Gly Gly
225                 230                 235                 240

Tyr Tyr Gln Asn Tyr Gln Gly Tyr Ser Gly Tyr Gln Gln Gly Gly Tyr
                245                 250                 255

Gln Gln Tyr Asn Pro Asp Ala Gly Tyr Gln Gln Gln Tyr Asn Pro Gln
            260                 265                 270

Gly Gly Tyr Gln Gln Tyr Asn Pro Gln Gly Gly Tyr Gln His Gln Phe
        275                 280                 285

Asn Pro Gln Gly Gly Arg Gly Asn Tyr Lys Asn Phe Asn Tyr Asn Asn
    290                 295                 300

Asn Leu Gln Gly Tyr Gln Ala Gly
305                 310
```

<210> SEQ ID NO 51
<211> LENGTH: 1011
<212> TYPE: DNA
<213> ORGANISM: Artificial Sequence
<220> FEATURE:
<223> OTHER INFORMATION: DNA sequence of Sup35N fused at the 5' end of adenylate kinase from Thermotoga maritima.

<400> SEQUENCE: 51

```
atggactcta accagggtaa caaccagcag aactaccagc agtactctca gaacggtaac      60

cagcagcagg gtaacaaccg ttaccagggt taccaggctt acaacgctca ggctcagccg     120
```

```
ggtggtggtt actaccagaa ctaccagggt tactccggtt atcagcaagg tggctaccaa    180

caatataatc cagacgctgg ctatcaacag caatataatc ctcagggtgg ttaccagcag    240

tacaacccgc aaggcggtta tcaacaccag ttcaatccgc agggtggtcg tggtaactac    300

aaaaacttca actacaacaa caacctgcag ggttaccagg ctggaattat gatggcctat    360

ctggtttttc ttggtccacc gggggcaggc aaaggtacct atgcgaaacg tttacaggaa    420

atcaccggca tcccgcacat tagcacgggc gacatttttc gtgatattgt caaaaaggaa    480

aatgacgaat taggtaagaa aattaaagaa attatggagc gcggcgagtt ggtgccggac    540

gaactggtga atgaagttgt caaacgtcgg ctgtctgaaa aggattgcga acgtggcttt    600

attttggacg gttacccgcg tacagtagct caggcagagt ttctcgacgg cttcctgaag    660

actcagaata aggagttaac ggctgcggtc ctgttcgagg tgcctgaaga ggtggtcgtt    720

cagcgtctga ccgcgcggcg tatctgcccg aagtgtggtc gtatttacaa cctgatttca    780

cttcctccaa aagaagatga actgtgtgat gactgcaaag taaaactggt gcaacgcgaa    840

gatgataaag aggaaactgt gcgccatcgc tacaaagtat atctggaaaa aacccaaccg    900

gttatcgatt attatgataa aaaaggcatt ttgaaacgcg ttgatgggac catcggcatc    960

gataacgtga ttgccgaagt tctcaaaatc attgggtgga gtgataaata g            1011
```

```
<210> SEQ ID NO 52
<211> LENGTH: 336
<212> TYPE: PRT
<213> ORGANISM: Artificial Sequence
<220> FEATURE:
<223> OTHER INFORMATION: Protein sequence of adenylate kinase from
      Thermotoga maritima fused at the N-terminal with Sup35N.

<400> SEQUENCE: 52

Met Asp Ser Asn Gln Gly Asn Asn Gln Gln Asn Tyr Gln Gln Tyr Ser
1               5                   10                  15

Gln Asn Gly Asn Gln Gln Gln Gly Asn Asn Arg Tyr Gln Gly Tyr Gln
            20                  25                  30

Ala Tyr Asn Ala Gln Ala Gln Pro Gly Gly Gly Tyr Tyr Gln Asn Tyr
        35                  40                  45

Gln Gly Tyr Ser Gly Tyr Gln Gln Gly Gly Tyr Gln Gln Tyr Asn Pro
    50                  55                  60

Asp Ala Gly Tyr Gln Gln Gln Tyr Asn Pro Gln Gly Gly Tyr Gln Gln
65                  70                  75                  80

Tyr Asn Pro Gln Gly Gly Tyr Gln His Gln Phe Asn Pro Gln Gly Gly
                85                  90                  95

Arg Gly Asn Tyr Lys Asn Phe Asn Tyr Asn Asn Asn Leu Gln Gly Tyr
            100                 105                 110

Gln Ala Gly Ile Met Met Ala Tyr Leu Val Phe Leu Gly Pro Pro Gly
        115                 120                 125

Ala Gly Lys Gly Thr Tyr Ala Lys Arg Leu Gln Glu Ile Thr Gly Ile
    130                 135                 140

Pro His Ile Ser Thr Gly Asp Ile Phe Arg Asp Ile Val Lys Lys Glu
145                 150                 155                 160

Asn Asp Glu Leu Gly Lys Lys Ile Lys Glu Ile Met Glu Arg Gly Glu
                165                 170                 175

Leu Val Pro Asp Glu Leu Val Asn Glu Val Val Lys Arg Arg Leu Ser
            180                 185                 190

Glu Lys Asp Cys Glu Arg Gly Phe Ile Leu Asp Gly Tyr Pro Arg Thr
```

```
        195                 200                 205

Val Ala Gln Ala Glu Phe Leu Asp Gly Phe Leu Lys Thr Gln Asn Lys
    210                 215                 220

Glu Leu Thr Ala Ala Val Leu Phe Glu Val Pro Glu Glu Val Val Val
225                 230                 235                 240

Gln Arg Leu Thr Ala Arg Arg Ile Cys Pro Lys Cys Gly Arg Ile Tyr
                245                 250                 255

Asn Leu Ile Ser Leu Pro Pro Lys Glu Asp Glu Leu Cys Asp Asp Cys
            260                 265                 270

Lys Val Lys Leu Val Gln Arg Glu Asp Asp Lys Glu Glu Thr Val Arg
        275                 280                 285

His Arg Tyr Lys Val Tyr Leu Glu Lys Thr Gln Pro Val Ile Asp Tyr
    290                 295                 300

Tyr Asp Lys Lys Gly Ile Leu Lys Arg Val Asp Gly Thr Ile Gly Ile
305                 310                 315                 320

Asp Asn Val Ile Ala Glu Val Leu Lys Ile Ile Gly Trp Ser Asp Lys
                325                 330                 335


<210> SEQ ID NO 53
<211> LENGTH: 1025
<212> TYPE: PRT
<213> ORGANISM: Artificial Sequence
<220> FEATURE:
<223> OTHER INFORMATION: DNA sequence of Sup35N fused at the 3' end of
      adenylate kinase from Thermotoga maritima.

<400> SEQUENCE: 53

Ala Thr Gly Ala Thr Gly Gly Cys Cys Thr Ala Thr Cys Thr Gly Gly
1               5                   10                  15

Thr Thr Thr Thr Thr Cys Thr Thr Gly Gly Thr Cys Cys Ala Cys Cys
            20                  25                  30

Gly Gly Gly Gly Gly Cys Ala Gly Gly Cys Ala Ala Ala Gly Gly Thr
        35                  40                  45

Ala Cys Cys Thr Ala Thr Gly Cys Gly Ala Ala Ala Cys Gly Thr Thr
    50                  55                  60

Thr Ala Cys Ala Gly Gly Ala Ala Ala Thr Cys Ala Cys Cys Gly Gly
65                  70                  75                  80

Cys Ala Thr Cys Cys Cys Gly Cys Ala Cys Ala Thr Thr Ala Gly Cys
                85                  90                  95

Ala Cys Gly Gly Gly Cys Gly Ala Cys Ala Thr Thr Thr Thr Thr Cys
            100                 105                 110

Gly Thr Gly Ala Thr Ala Thr Thr Gly Thr Cys Ala Ala Ala Ala Ala
        115                 120                 125

Gly Gly Ala Ala Ala Ala Thr Gly Ala Cys Gly Ala Ala Thr Thr Ala
    130                 135                 140

Gly Gly Thr Ala Ala Gly Ala Ala Ala Ala Thr Thr Ala Ala Ala Gly
145                 150                 155                 160

Ala Ala Ala Thr Thr Ala Thr Gly Gly Ala Gly Cys Gly Cys Gly Gly
                165                 170                 175

Cys Gly Ala Gly Thr Thr Gly Gly Thr Gly Cys Cys Gly Gly Ala Cys
            180                 185                 190

Gly Ala Ala Cys Thr Gly Gly Thr Gly Ala Ala Thr Gly Ala Ala Gly
        195                 200                 205

Thr Thr Gly Thr Cys Ala Ala Ala Cys Gly Thr Cys Gly Gly Cys Thr
    210                 215                 220
```

-continued

```
Gly Thr Cys Thr Gly Ala Ala Ala Ala Gly Gly Ala Thr Thr Gly Cys
225                 230                 235                 240

Gly Ala Ala Cys Gly Thr Gly Gly Cys Thr Thr Thr Ala Thr Thr Thr
                245                 250                 255

Thr Gly Gly Ala Cys Gly Gly Thr Thr Ala Cys Cys Cys Gly Cys Gly
            260                 265                 270

Thr Ala Cys Ala Gly Thr Ala Gly Cys Thr Cys Ala Gly Gly Cys Ala
        275                 280                 285

Gly Ala Gly Thr Thr Thr Cys Thr Cys Gly Ala Cys Gly Gly Cys Thr
    290                 295                 300

Thr Cys Cys Thr Gly Ala Ala Gly Ala Cys Thr Cys Ala Gly Ala Ala
305                 310                 315                 320

Thr Ala Ala Gly Gly Ala Gly Thr Thr Ala Ala Cys Gly Gly Cys Thr
                325                 330                 335

Gly Cys Gly Gly Thr Cys Cys Thr Gly Thr Thr Cys Gly Ala Gly Gly
            340                 345                 350

Thr Gly Cys Cys Thr Gly Ala Ala Gly Ala Gly Gly Thr Gly Gly Thr
        355                 360                 365

Cys Gly Thr Thr Cys Ala Gly Cys Gly Thr Cys Thr Gly Ala Cys Cys
    370                 375                 380

Gly Cys Gly Cys Gly Gly Cys Gly Thr Ala Thr Cys Thr Gly Cys Cys
385                 390                 395                 400

Cys Gly Ala Ala Gly Thr Gly Thr Gly Gly Thr Cys Gly Thr Ala Thr
                405                 410                 415

Thr Thr Ala Cys Ala Ala Cys Cys Thr Gly Ala Thr Thr Thr Cys Ala
            420                 425                 430

Cys Thr Thr Cys Cys Thr Cys Cys Ala Ala Ala Ala Gly Ala Ala Gly
        435                 440                 445

Ala Thr Gly Ala Ala Cys Thr Gly Thr Gly Thr Gly Ala Thr Gly Ala
    450                 455                 460

Cys Thr Gly Cys Ala Ala Ala Gly Thr Ala Ala Ala Ala Cys Thr Gly
465                 470                 475                 480

Gly Thr Gly Cys Ala Ala Cys Gly Cys Gly Ala Ala Gly Ala Thr Gly
                485                 490                 495

Ala Thr Ala Ala Ala Gly Ala Gly Gly Ala Ala Ala Cys Thr Gly Thr
            500                 505                 510

Gly Cys Gly Cys Cys Ala Thr Cys Gly Cys Thr Ala Cys Ala Ala Ala
        515                 520                 525

Gly Thr Ala Thr Ala Thr Cys Thr Gly Gly Ala Ala Ala Ala Ala Ala
    530                 535                 540

Cys Cys Cys Ala Ala Cys Cys Gly Gly Thr Thr Ala Thr Cys Gly Ala
545                 550                 555                 560

Thr Thr Ala Thr Thr Ala Thr Gly Ala Thr Ala Ala Ala Ala Ala Ala
                565                 570                 575

Gly Gly Cys Ala Thr Thr Thr Thr Gly Ala Ala Ala Cys Gly Cys Gly
            580                 585                 590

Thr Thr Gly Ala Thr Gly Gly Gly Ala Cys Cys Ala Thr Cys Gly Gly
        595                 600                 605

Cys Ala Thr Cys Gly Ala Thr Ala Ala Cys Gly Thr Gly Ala Thr Thr
    610                 615                 620

Gly Cys Cys Gly Ala Ala Gly Thr Thr Cys Thr Cys Ala Ala Ala Ala
625                 630                 635                 640

Thr Cys Ala Thr Thr Gly Gly Gly Thr Gly Gly Ala Gly Thr Gly Ala
```

```
                645                 650                 655

Thr Ala Ala Ala Cys Thr Gly Thr Cys Gly Ala Gly Thr Ala Thr Gly
            660                 665                 670

Gly Ala Cys Thr Cys Thr Ala Ala Cys Cys Ala Gly Gly Gly Thr Ala
        675                 680                 685

Ala Cys Ala Ala Cys Cys Ala Gly Cys Ala Gly Ala Ala Cys Thr Ala
    690                 695                 700

Cys Cys Ala Gly Cys Ala Gly Thr Ala Cys Thr Cys Thr Cys Ala Gly
705                 710                 715                 720

Ala Ala Cys Gly Gly Thr Ala Ala Cys Cys Ala Gly Cys Ala Gly Cys
                725                 730                 735

Ala Gly Gly Gly Thr Ala Ala Cys Ala Ala Cys Cys Gly Thr Thr Ala
            740                 745                 750

Cys Cys Ala Gly Gly Gly Thr Thr Ala Cys Cys Ala Gly Gly Cys Thr
        755                 760                 765

Thr Ala Cys Ala Ala Cys Gly Cys Thr Cys Ala Gly Gly Cys Thr Cys
    770                 775                 780

Ala Gly Cys Cys Gly Gly Gly Thr Gly Gly Thr Gly Gly Thr Thr Ala
785                 790                 795                 800

Cys Thr Ala Cys Cys Ala Gly Ala Ala Cys Thr Ala Cys Cys Ala Gly
                805                 810                 815

Gly Gly Thr Thr Ala Cys Thr Cys Cys Gly Gly Thr Thr Ala Thr Cys
            820                 825                 830

Ala Gly Cys Ala Ala Gly Gly Thr Gly Gly Cys Thr Ala Cys Cys Ala
        835                 840                 845

Ala Cys Ala Ala Thr Ala Thr Ala Ala Thr Cys Cys Ala Gly Ala Cys
    850                 855                 860

Gly Cys Thr Gly Gly Cys Thr Ala Thr Cys Ala Ala Cys Ala Gly Cys
865                 870                 875                 880

Ala Ala Thr Ala Thr Ala Ala Thr Cys Cys Thr Cys Ala Gly Gly Gly
                885                 890                 895

Thr Gly Gly Thr Thr Ala Cys Cys Ala Gly Cys Ala Gly Thr Ala Cys
            900                 905                 910

Ala Ala Cys Cys Cys Gly Cys Ala Ala Gly Gly Cys Gly Gly Thr Thr
        915                 920                 925

Ala Thr Cys Ala Ala Cys Ala Cys Cys Ala Gly Thr Thr Cys Ala Ala
    930                 935                 940

Thr Cys Cys Gly Cys Ala Gly Gly Gly Thr Gly Gly Thr Cys Gly Thr
945                 950                 955                 960

Gly Gly Thr Ala Ala Cys Thr Ala Cys Ala Ala Ala Ala Ala Cys Thr
                965                 970                 975

Thr Cys Ala Ala Cys Thr Ala Cys Ala Ala Cys Ala Ala Cys Ala Ala
            980                 985                 990

Cys Cys Thr Gly Cys Ala Gly Gly  Gly Thr Thr Ala Cys  Cys Ala Gly
        995                 1000                1005

Gly Cys  Thr Gly Gly Thr Thr  Ala Ala Gly Thr Cys  Gly Ala Cys
    1010                1015                1020

Gly Cys
    1025
```

<210> SEQ ID NO 54
<211> LENGTH: 338
<212> TYPE: PRT
<213> ORGANISM: Artificial Sequence
<220> FEATURE:
<223> OTHER INFORMATION: Protein sequence of adenylate kinase from Thermotoga maritima fused at the C-terminal fusion with Sup35N

<400> SEQUENCE: 54

```
Met Met Ala Tyr Leu Val Phe Leu Gly Pro Pro Gly Ala Gly Lys Gly
1               5                   10                  15

Thr Tyr Ala Lys Arg Leu Gln Glu Ile Thr Gly Ile Pro His Ile Ser
            20                  25                  30

Thr Gly Asp Ile Phe Arg Asp Ile Val Lys Lys Glu Asn Asp Glu Leu
        35                  40                  45

Gly Lys Lys Ile Lys Glu Ile Met Glu Arg Gly Glu Leu Val Pro Asp
    50                  55                  60

Glu Leu Val Asn Glu Val Val Lys Arg Arg Leu Ser Glu Lys Asp Cys
65                  70                  75                  80

Glu Arg Gly Phe Ile Leu Asp Gly Tyr Pro Arg Thr Val Ala Gln Ala
                85                  90                  95

Glu Phe Leu Asp Gly Phe Leu Lys Thr Gln Asn Lys Glu Leu Thr Ala
            100                 105                 110

Ala Val Leu Phe Glu Val Pro Glu Glu Val Val Val Gln Arg Leu Thr
        115                 120                 125

Ala Arg Arg Ile Cys Pro Lys Cys Gly Arg Ile Tyr Asn Leu Ile Ser
    130                 135                 140

Leu Pro Pro Lys Glu Asp Glu Leu Cys Asp Asp Cys Lys Val Lys Leu
145                 150                 155                 160

Val Gln Arg Glu Asp Asp Lys Glu Glu Thr Val Arg His Arg Tyr Lys
                165                 170                 175

Val Tyr Leu Glu Lys Thr Gln Pro Val Ile Asp Tyr Tyr Asp Lys Lys
            180                 185                 190

Gly Ile Leu Lys Arg Val Asp Gly Thr Ile Gly Ile Asp Asn Val Ile
        195                 200                 205

Ala Glu Val Leu Lys Ile Ile Gly Trp Ser Asp Lys Leu Ser Ser Met
    210                 215                 220

Asp Ser Asn Gln Gly Asn Asn Gln Gln Asn Tyr Gln Gln Tyr Ser Gln
225                 230                 235                 240

Asn Gly Asn Gln Gln Gln Gly Asn Asn Arg Tyr Gln Gly Tyr Gln Ala
                245                 250                 255

Tyr Asn Ala Gln Ala Gln Pro Gly Gly Gly Tyr Tyr Gln Asn Tyr Gln
            260                 265                 270

Gly Tyr Ser Gly Tyr Gln Gln Gly Gly Tyr Gln Gln Tyr Asn Pro Asp
        275                 280                 285

Ala Gly Tyr Gln Gln Gln Tyr Asn Pro Gln Gly Gly Tyr Gln Gln Tyr
    290                 295                 300

Asn Pro Gln Gly Gly Tyr Gln His Gln Phe Asn Pro Gln Gly Gly Arg
305                 310                 315                 320

Gly Asn Tyr Lys Asn Phe Asn Tyr Asn Asn Asn Leu Gln Gly Tyr Gln
                325                 330                 335

Ala Gly
```

<210> SEQ ID NO 55
<211> LENGTH: 21
<212> TYPE: DNA
<213> ORGANISM: Artificial Sequence
<220> FEATURE:
<223> OTHER INFORMATION: DNA sequence encoding a short Sup35 peptide capable of aggregating to form amyloid fibrils; for use as a fusion peptide with tAK genes.

<400> SEQUENCE: 55
ggtaacaacc agcagaacta c 21

<210> SEQ ID NO 56
<211> LENGTH: 7
<212> TYPE: PRT
<213> ORGANISM: Artificial Sequence
<220> FEATURE:
<223> OTHER INFORMATION: Sup35 derived amyloid peptide

<400> SEQUENCE: 56

Gly Asn Asn Gln Gln Asn Tyr
1 5

<210> SEQ ID NO 57
<211> LENGTH: 1593
<212> TYPE: DNA
<213> ORGANISM: Artificial Sequence
<220> FEATURE:
<223> OTHER INFORMATION: DNA sequence encoding a Norovirus capsid protein (58kDa)

<400> SEQUENCE: 57
atgatgatgg cgtctaagga cgctacatca agcgtggatg gcgctagtgg cgctggtcag 60
ttggtaccgg aggttaatgc ttctgaccct cttgcaatgg atcctgtagc aggttcttcg 120
acagcagtcg cgactgctgg acaagttaat cctattgatc cctggataat taataatttt 180
gtgcaagccc cccaaggtga atttactatt tccccaaata atacccccgg tgatgttttg 240
tttgatttga gtttgggtcc ccatcttaat cctttcttgc tccatctatc acaaatgtat 300
aatggttggg ttggtaacat gagagtcagg attatgctag ctggtaatgc ctttactgcg 360
gggaagataa tagtttcctg cataccccct ggttttggtt cacataatct tactatagca 420
caagcaactc tctttccaca tgtgattgct gatgttagga ctctagaccc cattgaggtg 480
cctttggaag atgttaggaa tgttctcttt cataataatg atagaaatca acaaaccatg 540
cgccttgtgt gcatgctgta caccccccctc cgcactggtg gtggtactgg tgattctttt 600
gtagttgcag ggcgagttat gacttgcccc agtcctgatt ttaatttctt gtttttagtc 660
cctcctacgg tggagcagaa aaccaggccc ttcacactcc caaatctgcc attgagttct 720
ctgtctaact cacgtgcccc tctcccaatc agtagtatgg gcatttcccc agacaatgtc 780
cagagtgtgc agttccaaaa tggtcggtgt actctggatg gccgcctggt tggcaccacc 840
ccagtttcat tgtcacatgt tgccaagata agagggacct ccaatggcac tgtaatcaac 900
cttactgaat tggatggcac accctttcac ccttttgagg gccctgcccc cattgggttt 960
ccagacctcg gtggttgtga ttggcatatc aatatgacac agtttggcca ttctagccag 1020
acccagtatg atgtagacac caccccctgac acttttgtcc cccatcttgg ttcaattcag 1080
gcaaatggca ttggcagtgg taattatgtt ggtgttctta gctggatttc ccccccatca 1140
cacccgtctg gctcccaagt tgacctttgg aagatcccca attatgggtc aagtattacg 1200
gaggcaacac atctagcccc ttctgtatac ccccctggtt tcggagaggt attggtcttt 1260
ttcatgtcaa aaatgccagg tcctggtgct tataatttgc cctgtctatt accacaagag 1320
tacatttcac atcttgctag tgaacaagcc cctactgtag gtgaggctgc cctgctccac 1380
tatgttgacc ctgataccgg tcggaatctt ggggaattca aagcataccc tgatggtttc 1440
ctcacttgtg tccccaatgg ggctagctcg ggtccacaac agctgccgat caatggggtc 1500
tttgtctttg tttcatgggt gtccagattt tatcaattaa agcctgtggg aactgccagc 1560
tcggcaagag gtaggcttgg tctgcgccga taa 1593

<210> SEQ ID NO 58
<211> LENGTH: 530
<212> TYPE: PRT
<213> ORGANISM: Artificial Sequence
<220> FEATURE:
<223> OTHER INFORMATION: Protein sequence of Norovirus capsid protein (58kDa)

<400> SEQUENCE: 58

```
Met Met Met Ala Ser Lys Asp Ala Thr Ser Ser Val Asp Gly Ala Ser
1               5                   10                  15

Gly Ala Gly Gln Leu Val Pro Glu Val Asn Ala Ser Asp Pro Leu Ala
            20                  25                  30

Met Asp Pro Val Ala Gly Ser Ser Thr Ala Val Ala Thr Ala Gly Gln
        35                  40                  45

Val Asn Pro Ile Asp Pro Trp Ile Ile Asn Asn Phe Val Gln Ala Pro
    50                  55                  60

Gln Gly Glu Phe Thr Ile Ser Pro Asn Asn Thr Pro Gly Asp Val Leu
65                  70                  75                  80

Phe Asp Leu Ser Leu Gly Pro His Leu Asn Pro Phe Leu Leu His Leu
                85                  90                  95

Ser Gln Met Tyr Asn Gly Trp Val Gly Asn Met Arg Val Arg Ile Met
            100                 105                 110

Leu Ala Gly Asn Ala Phe Thr Ala Gly Lys Ile Ile Val Ser Cys Ile
        115                 120                 125

Pro Pro Gly Phe Gly Ser His Asn Leu Thr Ile Ala Gln Ala Thr Leu
    130                 135                 140

Phe Pro His Val Ile Ala Asp Val Arg Thr Leu Asp Pro Ile Glu Val
145                 150                 155                 160

Pro Leu Glu Asp Val Arg Asn Val Leu Phe His Asn Asn Asp Arg Asn
                165                 170                 175

Gln Gln Thr Met Arg Leu Val Cys Met Leu Tyr Thr Pro Leu Arg Thr
            180                 185                 190

Gly Gly Gly Thr Gly Asp Ser Phe Val Val Ala Gly Arg Val Met Thr
        195                 200                 205

Cys Pro Ser Pro Asp Phe Asn Phe Leu Phe Leu Val Pro Pro Thr Val
    210                 215                 220

Glu Gln Lys Thr Arg Pro Phe Thr Leu Pro Asn Leu Pro Leu Ser Ser
225                 230                 235                 240

Leu Ser Asn Ser Arg Ala Pro Leu Pro Ile Ser Ser Met Gly Ile Ser
                245                 250                 255

Pro Asp Asn Val Gln Ser Val Gln Phe Gln Asn Gly Arg Cys Thr Leu
            260                 265                 270

Asp Gly Arg Leu Val Gly Thr Thr Pro Val Ser Leu Ser His Val Ala
        275                 280                 285

Lys Ile Arg Gly Thr Ser Asn Gly Thr Val Ile Asn Leu Thr Glu Leu
    290                 295                 300

Asp Gly Thr Pro Phe His Pro Phe Glu Gly Pro Ala Pro Ile Gly Phe
305                 310                 315                 320

Pro Asp Leu Gly Gly Cys Asp Trp His Ile Asn Met Thr Gln Phe Gly
                325                 330                 335
```

```
His Ser Ser Gln Thr Gln Tyr Asp Val Asp Thr Thr Pro Asp Thr Phe
            340                 345                 350

Val Pro His Leu Gly Ser Ile Gln Ala Asn Gly Ile Gly Ser Gly Asn
        355                 360                 365

Tyr Val Gly Val Leu Ser Trp Ile Ser Pro Pro Ser His Pro Ser Gly
    370                 375                 380

Ser Gln Val Asp Leu Trp Lys Ile Pro Asn Tyr Gly Ser Ser Ile Thr
385                 390                 395                 400

Glu Ala Thr His Leu Ala Pro Ser Val Tyr Pro Pro Gly Phe Gly Glu
                405                 410                 415

Val Leu Val Phe Phe Met Ser Lys Met Pro Gly Pro Gly Ala Tyr Asn
            420                 425                 430

Leu Pro Cys Leu Leu Pro Gln Glu Tyr Ile Ser His Leu Ala Ser Glu
        435                 440                 445

Gln Ala Pro Thr Val Gly Glu Ala Ala Leu Leu His Tyr Val Asp Pro
    450                 455                 460

Asp Thr Gly Arg Asn Leu Gly Glu Phe Lys Ala Tyr Pro Asp Gly Phe
465                 470                 475                 480

Leu Thr Cys Val Pro Asn Gly Ala Ser Ser Gly Pro Gln Gln Leu Pro
                485                 490                 495

Ile Asn Gly Val Phe Val Phe Val Ser Trp Val Ser Arg Phe Tyr Gln
            500                 505                 510

Leu Lys Pro Val Gly Thr Ala Ser Ser Ala Arg Gly Arg Leu Gly Leu
        515                 520                 525

Arg Arg
    530
```

<210> SEQ ID NO 59
<211> LENGTH: 1593
<212> TYPE: DNA
<213> ORGANISM: Artificial Sequence
<220> FEATURE:
<223> OTHER INFORMATION: DNA sequence for a synthetic gene encoding a Norovirus capsid protein (58kDa) optimised for expression in E.coli

<400> SEQUENCE: 59

```
atgatgatgg cttctaaaga cgctacctct tctgttgacg gtgcttctgg tgctggtcag      60

ctggttccgg aagttaacgc ttctgacccg ctggctatgg acccggttgc tggttcttct     120

accgctgttg ctaccgctgg tcaggttaac ccgatcgacc cgtggatcat caacaacttc     180

gttcaggctc cgcagggtga attcaccatc tctccgaaca acaccccggg tgacgttctg     240

ttcgacctgt ctctgggtcc gcacctgaac ccgttcctgc tgcacctgtc tcagatgtac     300

aacggttggg ttggtaacat gcgtgttcgt atcatgctgg ctggtaacgc tttcaccgct     360

ggtaaaatca tcgtttcttg catcccgccg ggtttcggtt ctcacaacct gaccatcgct     420

caggctaccc tgttcccgca cgttatcgct gacgttcgta ccctggaccc gatcgaagtt     480

ccgctggaag acgttcgtaa cgttctgttc cacaacaacg accgtaacca gcagaccatg     540

cgtctggttt gcatgctgta caccccgctg cgtaccggtg gtggtaccgg tgactctttc     600

gttgttgctg gtcgtgttat gacctgcccg tctccggact tcaacttcct gttcctggtt     660

ccgccgaccg ttgaacagaa aacccgtccg ttcaccctgc cgaacctgcc gctgtcttct     720

ctgtctaact ctcgtgctcc gctgccgatc tcttctatgg gtatctctcc ggacaacgtt     780

cagtctgttc agttccagaa cggtcgttgc accctggacg gtcgtctggt tggtaccacc     840
```

-continued ccggtttctc tgtctcacgt tgctaaaatc cgtggtacct ctaacggtac cgttatcaac 900
ctgaccgaac tggacggtac cccgttccac ccgttcgaag gtccggctcc gatcggtttc 960
ccggacctgg gtggttgcga ctggcacatc aacatgaccc agttcggtca ctcttctcag 1020
acccagtacg acgttgacac caccccggac accttcgttc cgcacctggg ttctatccag 1080
gctaacggta tcggttctgg taactacgtt ggtgttctgt cttggatctc tccgccgtct 1140
cacccgtctg gttctcaggt tgacctgtgg aaaatcccga actacggttc ttctatcacc 1200
gaagctaccc acctggctcc gtctgtttac ccgccgggtt tcggtgaagt tctggttttc 1260
ttcatgtcta aaatgccggg tccgggtgct tacaacctgc cgtgcctgct gccgcaggaa 1320
tacatctctc acctggcttc tgaacaggct ccgaccgttg gtgaagctgc tctgctgcac 1380
tacgttgacc cggacaccgg tcgtaacctg ggtgaattca aagcttaccc ggacggtttc 1440
ctgacctgcg ttccgaacgg tgcttcttct ggtccgcagc agctgccgat caacggtgtt 1500
ttcgttttcg tttcttgggt ttctcgtttc taccagctga aaccggttgg taccgcttct 1560
tctgctcgtg gtcgtctggg tctgcgtcgt tag 1593

<210> SEQ ID NO 60
<211> LENGTH: 2250
<212> TYPE: DNA
<213> ORGANISM: Artificial Sequence
<220> FEATURE:
<223> OTHER INFORMATION: DNA sequence for a synthetic gene encoding a Norovirus capsid protein (58kDa) optimised for expression in E.coli fused at the 5' end of a gene encoding the tAK from Thermotoga maritima.

<400> SEQUENCE: 60
atgatgatgg cttctaaaga cgctacctct tctgttgacg gtgcttctgg tgctggtcag 60
ctggttccgg aagttaacgc ttctgacccg ctggctatgg acccggttgc tggttcttct 120
accgctgttg ctaccgctgg tcaggttaac ccgatcgacc cgtggatcat caacaacttc 180
gttcaggctc cgcagggtga attcaccatc tctccgaaca acaccccggg tgacgttctg 240
ttcgacctgt ctctgggtcc gcacctgaac ccgttcctgc tgcacctgtc tcagatgtac 300
aacggttggg ttggtaacat gcgtgttcgt atcatgctgg ctggtaacgc tttcaccgct 360
ggtaaaatca tcgtttcttg catcccgccg ggtttcggtt ctcacaacct gaccatcgct 420
caggctaccc tgttcccgca cgttatcgct gacgttcgta ccctggaccc gatcgaagtt 480
ccgctggaag acgttcgtaa cgttctgttc cacaacaacg accgtaacca gcagaccatg 540
cgtctggttt gcatgctgta caccccgctg cgtaccggtg gtggtaccgg tgactctttc 600
gttgttgctg gtcgtgttat gacctgcccg tctccggact tcaacttcct gttcctggtt 660
ccgccgaccg ttgaacagaa aacccgtccg ttcaccctgc cgaacctgcc gctgtcttct 720
ctgtctaact ctcgtgctcc gctgccgatc tcttctatgg gtatctctcc ggacaacgtt 780
cagtctgttc agttccagaa cggtcgttgc accctggacg gtcgtctggt tggtaccacc 840
ccggtttctc tgtctcacgt tgctaaaatc cgtggtacct ctaacggtac cgttatcaac 900
ctgaccgaac tggacggtac cccgttccac ccgttcgaag gtccggctcc gatcggtttc 960
ccggacctgg gtggttgcga ctggcacatc aacatgaccc agttcggtca ctcttctcag 1020
acccagtacg acgttgacac caccccggac accttcgttc cgcacctggg ttctatccag 1080
gctaacggta tcggttctgg taactacgtt ggtgttctgt cttggatctc tccgccgtct 1140
cacccgtctg gttctcaggt tgacctgtgg aaaatcccga actacggttc ttctatcacc 1200

-continued gaagctaccc acctggctcc gtctgtttac ccgccgggtt tcggtgaagt tctggttttc 1260
ttcatgtcta aaatgccggg tccgggtgct tacaacctgc cgtgcctgct gccgcaggaa 1320
tacatctctc acctggcttc tgaacaggct ccgaccgttg gtgaagctgc tctgctgcac 1380
tacgttgacc cggacaccgg tcgtaacctg ggtgaattca aagcttaccc ggacggtttc 1440
ctgacctgcg ttccgaacgg tgcttcttct ggtccgcagc agctgccgat caacggtgtt 1500
ttcgttttcg tttcttgggt ttctcgtttc taccagctga aaccggttgg taccgcttct 1560
tctgctcgtg gtcgtctggg tctgcgtcgt atgatggcct atctggtttt tcttggtcca 1620
ccgggggcag gcaaaggtac ctatgcgaaa cgtttacagg aaatcaccgg catcccgcac 1680
attagcacgg gcgacatttt tcgtgatatt gtcaaaaagg aaaatgacga attaggtaag 1740
aaaattaaag aaattatgga gcgcggcgag ttggtgccgg acgaactggt gaatgaagtt 1800
gtcaaacgtc ggctgtctga aaaggattgc gaacgtggct ttattttgga cggttacccg 1860
cgtacagtag ctcaggcaga gtttctcgac ggcttcctga agactcagaa taaggagtta 1920
acggctgcgg tcctgttcga ggtgcctgaa gaggtggtcg ttcagcgtct gaccgcgcgg 1980
cgtatctgcc cgaagtgtgg tcgtatttac aacctgattt cacttcctcc aaaagaagat 2040
gaactgtgtg atgactgcaa agtaaaactg gtgcaacgcg aagatgataa agaggaaact 2100
gtgcgccatc gctacaaagt atatctggaa aaaacccaac cggttatcga ttattatgat 2160
aaaaaaggca ttttgaaacg cgttgatggg accatcggca tcgataacgt gattgccgaa 2220
gttctcaaaa tcattgggtg gagtgataaa 2250

<210> SEQ ID NO 61
<211> LENGTH: 750
<212> TYPE: PRT
<213> ORGANISM: Artificial Sequence
<220> FEATURE:
<223> OTHER INFORMATION: Protein sequence of a Norovirus capsid protein (58kDa) fused at the N-terminus of the adenylate kinase from Thermotoga maritima

<400> SEQUENCE: 61

Met Met Met Ala Ser Lys Asp Ala Thr Ser Ser Val Asp Gly Ala Ser
1 5 10 15

Gly Ala Gly Gln Leu Val Pro Glu Val Asn Ala Ser Asp Pro Leu Ala
20 25 30

Met Asp Pro Val Ala Gly Ser Ser Thr Ala Val Ala Thr Ala Gly Gln
35 40 45

Val Asn Pro Ile Asp Pro Trp Ile Ile Asn Asn Phe Val Gln Ala Pro
50 55 60

Gln Gly Glu Phe Thr Ile Ser Pro Asn Asn Thr Pro Gly Asp Val Leu
65 70 75 80

Phe Asp Leu Ser Leu Gly Pro His Leu Asn Pro Phe Leu Leu His Leu
85 90 95

Ser Gln Met Tyr Asn Gly Trp Val Gly Asn Met Arg Val Arg Ile Met
100 105 110

Leu Ala Gly Asn Ala Phe Thr Ala Gly Lys Ile Ile Val Ser Cys Ile
115 120 125

Pro Pro Gly Phe Gly Ser His Asn Leu Thr Ile Ala Gln Ala Thr Leu
130 135 140

Phe Pro His Val Ile Ala Asp Val Arg Thr Leu Asp Pro Ile Glu Val
145 150 155 160

Pro Leu Glu Asp Val Arg Asn Val Leu Phe His Asn Asn Asp Arg Asn

-continued

```
                165                 170                 175

Gln Gln Thr Met Arg Leu Val Cys Met Leu Tyr Thr Pro Leu Arg Thr
            180                 185                 190

Gly Gly Gly Thr Gly Asp Ser Phe Val Val Ala Gly Arg Val Met Thr
        195                 200                 205

Cys Pro Ser Pro Asp Phe Asn Phe Leu Phe Leu Val Pro Pro Thr Val
    210                 215                 220

Glu Gln Lys Thr Arg Pro Phe Thr Leu Pro Asn Leu Pro Leu Ser Ser
225                 230                 235                 240

Leu Ser Asn Ser Arg Ala Pro Leu Pro Ile Ser Ser Met Gly Ile Ser
                245                 250                 255

Pro Asp Asn Val Gln Ser Val Gln Phe Gln Asn Gly Arg Cys Thr Leu
            260                 265                 270

Asp Gly Arg Leu Val Gly Thr Thr Pro Val Ser Leu Ser His Val Ala
        275                 280                 285

Lys Ile Arg Gly Thr Ser Asn Gly Thr Val Ile Asn Leu Thr Glu Leu
    290                 295                 300

Asp Gly Thr Pro Phe His Pro Phe Glu Gly Pro Ala Pro Ile Gly Phe
305                 310                 315                 320

Pro Asp Leu Gly Gly Cys Asp Trp His Ile Asn Met Thr Gln Phe Gly
                325                 330                 335

His Ser Ser Gln Thr Gln Tyr Asp Val Asp Thr Thr Pro Asp Thr Phe
            340                 345                 350

Val Pro His Leu Gly Ser Ile Gln Ala Asn Gly Ile Gly Ser Gly Asn
        355                 360                 365

Tyr Val Gly Val Leu Ser Trp Ile Ser Pro Pro Ser His Pro Ser Gly
    370                 375                 380

Ser Gln Val Asp Leu Trp Lys Ile Pro Asn Tyr Gly Ser Ser Ile Thr
385                 390                 395                 400

Glu Ala Thr His Leu Ala Pro Ser Val Tyr Pro Pro Gly Phe Gly Glu
                405                 410                 415

Val Leu Val Phe Phe Met Ser Lys Met Pro Gly Pro Gly Ala Tyr Asn
            420                 425                 430

Leu Pro Cys Leu Leu Pro Gln Glu Tyr Ile Ser His Leu Ala Ser Glu
        435                 440                 445

Gln Ala Pro Thr Val Gly Glu Ala Ala Leu Leu His Tyr Val Asp Pro
    450                 455                 460

Asp Thr Gly Arg Asn Leu Gly Glu Phe Lys Ala Tyr Pro Asp Gly Phe
465                 470                 475                 480

Leu Thr Cys Val Pro Asn Gly Ala Ser Ser Gly Pro Gln Gln Leu Pro
                485                 490                 495

Ile Asn Gly Val Phe Val Phe Val Ser Trp Val Ser Arg Phe Tyr Gln
            500                 505                 510

Leu Lys Pro Val Gly Thr Ala Ser Ser Ala Arg Gly Arg Leu Gly Leu
        515                 520                 525

Arg Arg Met Met Ala Tyr Leu Val Phe Leu Gly Pro Pro Gly Ala Gly
    530                 535                 540

Lys Gly Thr Tyr Ala Lys Arg Leu Gln Glu Ile Thr Gly Ile Pro His
545                 550                 555                 560

Ile Ser Thr Gly Asp Ile Phe Arg Asp Ile Val Lys Lys Glu Asn Asp
                565                 570                 575

Glu Leu Gly Lys Lys Ile Lys Glu Ile Met Glu Arg Gly Glu Leu Val
            580                 585                 590
```

-continued

```
Pro Asp Glu Leu Val Asn Glu Val Val Lys Arg Arg Leu Ser Glu Lys
        595                 600                 605

Asp Cys Glu Arg Gly Phe Ile Leu Asp Gly Tyr Pro Arg Thr Val Ala
    610                 615                 620

Gln Ala Glu Phe Leu Asp Gly Phe Leu Lys Thr Gln Asn Lys Glu Leu
625                 630                 635                 640

Thr Ala Ala Val Leu Phe Glu Val Pro Glu Glu Val Val Val Gln Arg
                645                 650                 655

Leu Thr Ala Arg Arg Ile Cys Pro Lys Cys Gly Arg Ile Tyr Asn Leu
            660                 665                 670

Ile Ser Leu Pro Pro Lys Glu Asp Glu Leu Cys Asp Asp Cys Lys Val
        675                 680                 685

Lys Leu Val Gln Arg Glu Asp Asp Lys Glu Glu Thr Val Arg His Arg
    690                 695                 700

Tyr Lys Val Tyr Leu Glu Lys Thr Gln Pro Val Ile Asp Tyr Tyr Asp
705                 710                 715                 720

Lys Lys Gly Ile Leu Lys Arg Val Asp Gly Thr Ile Gly Ile Asp Asn
                725                 730                 735

Val Ile Ala Glu Val Leu Lys Ile Ile Gly Trp Ser Asp Lys
            740                 745                 750
```

<210> SEQ ID NO 62
<211> LENGTH: 130
<212> TYPE: PRT
<213> ORGANISM: Bacteriophage MS2

<400> SEQUENCE: 62

```
Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Val Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Gln Asn Arg Lys Tyr Thr Ile Lys Val Glu
    50                  55                  60

Val Pro Lys Val Ala Thr Gln Thr Val Gly Gly Val Glu Leu Pro Val
65                  70                  75                  80

Ala Ala Trp Arg Ser Tyr Leu Asn Met Glu Leu Thr Ile Pro Ile Phe
                85                  90                  95

Ala Thr Asn Ser Asp Cys Glu Leu Ile Val Lys Ala Met Gln Gly Leu
            100                 105                 110

Leu Lys Asp Gly Asn Pro Ile Pro Ser Ala Ile Ala Ala Asn Ser Gly
        115                 120                 125

Ile Tyr
    130
```

<210> SEQ ID NO 63
<211> LENGTH: 127
<212> TYPE: PRT
<213> ORGANISM: Bacteriophage PP7

<400> SEQUENCE: 63

```
Ser Lys Thr Ile Val Leu Ser Val Gly Glu Ala Thr Arg Thr Leu Thr
1               5                   10                  15

Glu Ile Gln Ser Thr Ala Asp Arg Gln Ile Phe Glu Glu Lys Val Gly
            20                  25                  30
```

```
Pro Leu Val Gly Arg Leu Arg Leu Thr Ala Ser Leu Arg Gln Asn Gly
        35                  40                  45

Ala Lys Thr Ala Tyr Arg Val Asn Leu Lys Leu Asp Gln Ala Asp Val
    50                  55                  60

Val Asp Cys Ser Thr Ser Val Cys Gly Glu Leu Pro Lys Val Arg Tyr
65                  70                  75                  80

Thr Gln Val Trp Ser His Asp Val Thr Ile Val Ala Asn Ser Thr Glu
                85                  90                  95

Ala Ser Arg Lys Ser Leu Tyr Asp Leu Thr Lys Ser Leu Val Val Gln
            100                 105                 110

Ala Thr Ser Glu Asp Leu Val Val Asn Leu Val Pro Leu Gly Arg
        115                 120                 125


<210> SEQ ID NO 64
<211> LENGTH: 245
<212> TYPE: PRT
<213> ORGANISM: Bacteriophage PP7

<400> SEQUENCE: 64

Met Ser Lys Thr Ile Val Leu Ser Val Gly Glu Ala Thr Arg Thr Leu
1               5                   10                  15

Thr Glu Ile Gln Ser Thr Ala Asp Arg Gln Ile Phe Glu Glu Lys Val
            20                  25                  30

Gly Pro Leu Val Gly Arg Leu Arg Leu Thr Ala Ser Leu Arg Gln Asn
        35                  40                  45

Gly Ala Lys Thr Ala Tyr Arg Val Asn Leu Lys Leu Asp Gln Ala Asp
    50                  55                  60

Val Val Asp Ser Gly Leu Pro Lys Val Arg Tyr Thr Gln Val Trp Ser
65                  70                  75                  80

His Asp Val Thr Ile Val Ala Asn Ser Thr Glu Ala Ser Arg Lys Ser
                85                  90                  95

Leu Tyr Asp Leu Thr Lys Ser Leu Val Ala Thr Ser Gln Val Glu Asp
            100                 105                 110

Leu Val Val Asn Leu Val Pro Leu Gly Arg Tyr Gly Ser Lys Thr Ile
        115                 120                 125

Val Leu Ser Val Gly Glu Ala Thr Arg Thr Leu Thr Glu Ile Gln Ser
    130                 135                 140

Thr Ala Asp Arg Gln Ile Phe Glu Glu Lys Val Gly Pro Leu Val Gly
145                 150                 155                 160

Arg Leu Arg Leu Thr Ala Ser Leu Arg Gln Asn Gly Ala Lys Thr Ala
                165                 170                 175

Tyr Arg Val Asn Leu Lys Leu Asp Gln Ala Asp Val Val Asp Ser Gly
            180                 185                 190

Leu Pro Lys Val Arg Tyr Thr Gln Val Trp Ser His Asp Val Thr Ile
        195                 200                 205

Val Ala Asn Ser Thr Glu Ala Ser Arg Lys Ser Leu Tyr Asp Leu Thr
    210                 215                 220

Lys Ser Leu Val Ala Thr Ser Gln Val Glu Asp Leu Val Val Asn Leu
225                 230                 235                 240

Val Pro Leu Gly Arg
                245


<210> SEQ ID NO 65
<211> LENGTH: 151
<212> TYPE: PRT
```

<213> ORGANISM: Escherichia coli

<400> SEQUENCE: 65

Met Lys Leu Leu Lys Val Ala Ala Ile Ala Ala Ile Val Phe Ser Gly
1               5                   10                  15

Ser Ala Leu Ala Gly Val Val Pro Gln Tyr Gly Gly Gly Gly Asn His
            20                  25                  30

Gly Gly Gly Gly Asn Asn Ser Gly Pro Asn Ser Glu Leu Asn Ile Tyr
        35                  40                  45

Gln Tyr Gly Gly Gly Asn Ser Ala Leu Ala Leu Gln Thr Asp Ala Arg
    50                  55                  60

Asn Ser Asp Leu Thr Ile Thr Gln His Gly Gly Gly Asn Gly Ala Asp
65                  70                  75                  80

Val Gly Gln Gly Ser Asp Asp Ser Ser Ile Asp Leu Thr Gln Arg Gly
                85                  90                  95

Phe Gly Asn Ser Ala Thr Leu Asp Gln Trp Asn Gly Lys Asn Ser Glu
            100                 105                 110

Met Thr Val Lys Gln Phe Gly Gly Gly Asn Gly Ala Ala Val Asp Gln
        115                 120                 125

Thr Ala Ser Asn Ser Ser Val Asn Val Thr Gln Val Gly Phe Gly Asn
    130                 135                 140

Asn Ala Thr Ala His Gln Tyr
145                 150

<210> SEQ ID NO 66
<211> LENGTH: 151
<212> TYPE: PRT
<213> ORGANISM: Artificial Sequence
<220> FEATURE:
<223> OTHER INFORMATION: Protein sequence of AgfA protein from Salmonella

<400> SEQUENCE: 66

Met Lys Leu Leu Lys Val Ala Ala Phe Ala Ala Ile Val Val Ser Gly
1               5                   10                  15

Ser Ala Leu Ala Gly Val Val Pro Gln Trp Gly Gly Gly Gly Asn His
            20                  25                  30

Asn Gly Gly Gly Asn Ser Ser Gly Pro Asp Ser Thr Leu Ser Ile Tyr
        35                  40                  45

Gln Tyr Gly Ser Ala Asn Ala Ala Leu Ala Leu Gln Ser Asp Ala Arg
    50                  55                  60

Lys Ser Glu Thr Thr Ile Thr Gln Ser Gly Tyr Gly Asn Gly Ala Asp
65                  70                  75                  80

Val Gly Gln Gly Ala Asp Asn Ser Thr Ile Glu Leu Thr Gln Asn Gly
                85                  90                  95

Phe Arg Asn Asn Ala Thr Ile Asp Gln Trp Asn Ala Lys Asn Ser Asp
            100                 105                 110

Ile Thr Val Gly Gln Tyr Gly Gly Asn Asn Ala Ala Leu Val Asn Gln
        115                 120                 125

Thr Ala Ser Asp Ser Ser Val Met Val Arg Gln Val Gly Phe Gly Asn
    130                 135                 140

Asn Ala Thr Ala Asn Gln Tyr
145                 150

<210> SEQ ID NO 67
<211> LENGTH: 353
<212> TYPE: PRT

<213> ORGANISM: Artificial Sequence
<220> FEATURE:
<223> OTHER INFORMATION: Protein sequence of adenylate kinase from
Thermotoga maritima fused to the N terminus of E.coli CsgA

<400> SEQUENCE: 67

```
Met Met Ala Tyr Leu Val Phe Leu Gly Pro Pro Gly Ala Gly Lys Gly
1               5                   10                  15

Thr Tyr Ala Lys Arg Ile Gln Glu Lys Thr Gly Ile Pro His Ile Ser
            20                  25                  30

Thr Gly Asp Ile Phe Arg Asp Ile Val Lys Lys Glu Asn Asp Glu Leu
        35                  40                  45

Gly Lys Lys Ile Lys Glu Ile Met Glu Lys Gly Glu Leu Val Pro Asp
    50                  55                  60

Glu Leu Val Asn Glu Val Val Lys Arg Arg Leu Ser Glu Lys Asp Cys
65                  70                  75                  80

Glu Lys Gly Phe Ile Leu Asp Gly Tyr Pro Arg Thr Val Ala Gln Ala
                85                  90                  95

Glu Phe Leu Asp Ser Phe Leu Glu Ser Gln Asn Lys Gln Leu Thr Ala
            100                 105                 110

Ala Val Leu Phe Asp Val Pro Glu Asp Val Val Val Gln Arg Leu Thr
        115                 120                 125

Ser Arg Arg Ile Cys Pro Lys Cys Gly Arg Ile Tyr Asn Met Ile Ser
    130                 135                 140

Leu Pro Pro Lys Glu Asp Glu Leu Cys Asp Asp Cys Lys Val Lys Leu
145                 150                 155                 160

Val Gln Arg Asp Asp Asp Lys Glu Glu Thr Val Arg His Arg Tyr Lys
                165                 170                 175

Val Tyr Leu Glu Lys Thr Gln Pro Val Ile Asp Tyr Tyr Gly Lys Lys
            180                 185                 190

Gly Ile Leu Lys Arg Val Asp Gly Thr Ile Gly Ile Asp Asn Val Val
        195                 200                 205

Ala Glu Val Leu Lys Ile Ile Gly Trp Ser Asp Lys Gly Ser Gly Val
    210                 215                 220

Val Pro Gln Tyr Gly Gly Gly Gly Asn His Gly Gly Gly Gly Asn Asn
225                 230                 235                 240

Ser Gly Pro Asn Ser Glu Leu Asn Ile Tyr Gln Tyr Gly Gly Gly Asn
                245                 250                 255

Ser Ala Leu Ala Leu Gln Thr Asp Ala Arg Asn Ser Asp Leu Thr Ile
            260                 265                 270

Thr Gln His Gly Gly Gly Asn Gly Ala Asp Val Gly Gln Gly Ser Asp
        275                 280                 285

Asp Ser Ser Ile Asp Leu Thr Gln Arg Gly Phe Gly Asn Ser Ala Thr
    290                 295                 300

Leu Asp Gln Trp Asn Gly Lys Asn Ser Glu Met Thr Val Lys Gln Phe
305                 310                 315                 320

Gly Gly Gly Asn Gly Ala Ala Val Asp Gln Thr Ala Ser Asn Ser Ser
                325                 330                 335

Val Asn Val Thr Gln Val Gly Phe Gly Asn Asn Ala Thr Ala His Gln
            340                 345                 350

Tyr
```

<210> SEQ ID NO 68
<211> LENGTH: 83
<212> TYPE: PRT

```
<213> ORGANISM: Artificial Sequence
<220> FEATURE:
<223> OTHER INFORMATION: Protein sequence of hydrophobin 3 protein from
      Fusarium species

<400> SEQUENCE: 68

Met Gln Phe Ser Thr Leu Thr Thr Val Phe Ala Leu Val Ala Ala Ala
1               5                   10                  15

Val Ala Ala Pro His Gly Ser Ser Gly Gly Asn Asn Pro Val Cys Ser
            20                  25                  30

Ala Gln Asn Asn Gln Val Cys Cys Asn Gly Leu Leu Ser Cys Ala Val
        35                  40                  45

Gln Val Leu Gly Ser Asn Cys Asn Gly Asn Ala Tyr Cys Cys Asn Thr
    50                  55                  60

Glu Ala Pro Thr Gly Thr Leu Ile Asn Val Ala Leu Leu Asn Cys Val
65                  70                  75                  80

Lys Leu Leu


<210> SEQ ID NO 69
<211> LENGTH: 98
<212> TYPE: PRT
<213> ORGANISM: Artificial Sequence
<220> FEATURE:
<223> OTHER INFORMATION: Protein sequence of hydrophobin 5 protein from
      Fusarium species

<400> SEQUENCE: 69

Met Lys Phe Ser Leu Ala Ala Val Ala Leu Leu Gly Ala Val Val Ser
1               5                   10                  15

Ala Leu Pro Ala Asn Glu Lys Arg Gln Ala Tyr Ile Pro Cys Ser Gly
            20                  25                  30

Leu Tyr Gly Thr Ser Gln Cys Cys Ala Thr Asp Val Leu Gly Val Ala
        35                  40                  45

Asp Leu Asp Cys Gly Asn Pro Pro Ser Ser Pro Thr Asp Ala Asp Asn
    50                  55                  60

Phe Ser Ala Val Cys Ala Glu Ile Gly Gln Arg Ala Arg Cys Cys Val
65                  70                  75                  80

Leu Pro Ile Leu Asp Gln Gly Ile Leu Cys Asn Thr Pro Thr Gly Val
                85                  90                  95

Gln Asp


<210> SEQ ID NO 70
<211> LENGTH: 173
<212> TYPE: PRT
<213> ORGANISM: Balanus albicostatus

<400> SEQUENCE: 70

Val Pro Pro Pro Cys Asp Leu Ser Ile Lys Ser Lys Leu Lys Gln Val
1               5                   10                  15

Gly Ala Thr Ala Gly Asn Ala Ala Val Thr Thr Thr Gly Thr Thr Ser
            20                  25                  30

Gly Ser Gly Val Val Lys Cys Val Val Arg Thr Pro Thr Ser Val Glu
        35                  40                  45

Lys Lys Ala Ala Val Gly Asn Thr Gly Leu Ser Ala Val Ser Ala Ser
    50                  55                  60

Ala Ala Asn Gly Phe Phe Lys Asn Leu Gly Lys Ala Thr Thr Glu Val
65                  70                  75                  80

Lys Thr Thr Lys Asp Gly Thr Lys Val Lys Thr Lys Thr Ala Gly Lys
```

```
                85                  90                  95

Gly Lys Thr Gly Gly Thr Ala Thr Thr Ile Gln Ile Ala Asp Ala Asn
            100                 105                 110

Gly Gly Val Ser Glu Lys Ser Leu Lys Leu Asp Leu Leu Thr Asp Gly
        115                 120                 125

Leu Lys Phe Val Lys Val Thr Glu Lys Lys Gln Gly Thr Ala Thr Ser
    130                 135                 140

Ser Ser Gly His Lys Ala Ser Gly Val Gly His Ser Val Phe Lys Val
145                 150                 155                 160

Leu Asn Glu Ala Glu Thr Glu Leu Glu Leu Lys Gly Leu
                165                 170


<210> SEQ ID NO 71
<211> LENGTH: 202
<212> TYPE: PRT
<213> ORGANISM: Megabalanus rosa

<400> SEQUENCE: 71

Met Lys Trp Phe Leu Phe Leu Leu Thr Thr Ala Val Leu Ala Ala Val
1               5                   10                  15

Val Ser Ala His Glu Glu Asp Gly Val Cys Asn Ser Asn Ala Pro Cys
            20                  25                  30

Tyr His Cys Asp Ala Asn Gly Glu Asn Cys Ser Cys Asn Cys Glu Leu
        35                  40                  45

Phe Asp Cys Glu Ala Lys Lys Pro Asp Gly Ser Tyr Ala His Pro Cys
    50                  55                  60

Arg Arg Cys Asp Ala Asn Asn Ile Cys Lys Cys Ser Cys Thr Ala Ile
65                  70                  75                  80

Pro Cys Asn Glu Asp His Pro Cys His His Cys His Glu Glu Asp Asp
                85                  90                  95

Gly Asp Thr His Cys His Cys Ser Cys Glu His Ser His Asp His His
            100                 105                 110

Asp Asp Asp Thr His Gly Glu Cys Thr Lys Lys Ala Pro Cys Trp Arg
        115                 120                 125

Cys Glu Tyr Asn Ala Asp Leu Lys His Asp Val Cys Gly Cys Glu Cys
    130                 135                 140

Ser Lys Leu Pro Cys Asn Asp Glu His Pro Cys Tyr Arg Lys Glu Gly
145                 150                 155                 160

Gly Val Val Ser Cys Asp Cys Lys Thr Ile Thr Cys Asn Glu Asp His
                165                 170                 175

Pro Cys Tyr His Ser Tyr Glu Glu Asp Gly Val Thr Lys Ser Asp Cys
            180                 185                 190

Asp Cys Glu His Ser Pro Gly Pro Ser Glu
        195                 200


<210> SEQ ID NO 72
<211> LENGTH: 576
<212> TYPE: PRT
<213> ORGANISM: Artificial Sequence
<220> FEATURE:
<223> OTHER INFORMATION: Protein sequence of fusion of the barnacle
      protein from Balanus albicostatus with the adenylate kinase from
      Thermotgoa maritima; N-terminal fusion

<400> SEQUENCE: 72

Met Arg Val Leu Val Ile Asn Ser Gly Ser Ser Ser Ile Lys Tyr Gln
1               5                   10                  15
```

-continued

```
Leu Ile Glu Met Glu Gly Glu Lys Val Leu Cys Lys Gly Ile Ala Glu
            20                  25                  30

Arg Ile Gly Ile Glu Gly Ser Arg Leu Val His Arg Val Gly Asp Glu
        35                  40                  45

Lys His Val Ile Glu Arg Glu Leu Pro Asp His Glu Glu Ala Leu Lys
    50                  55                  60

Leu Ile Leu Asn Thr Leu Val Asp Glu Lys Leu Gly Val Ile Lys Asp
65                  70                  75                  80

Leu Lys Glu Ile Asp Ala Val Gly His Arg Val Val His Gly Gly Glu
                85                  90                  95

Arg Phe Lys Glu Ser Val Leu Val Asp Glu Glu Val Leu Lys Ala Ile
            100                 105                 110

Glu Glu Val Ser Pro Leu Ala Pro Leu His Asn Pro Ala Asn Leu Met
        115                 120                 125

Gly Ile Lys Ala Ala Met Lys Leu Leu Pro Gly Val Pro Asn Val Ala
    130                 135                 140

Val Phe Asp Thr Ala Phe His Gln Thr Ile Pro Gln Lys Ala Tyr Leu
145                 150                 155                 160

Tyr Ala Ile Pro Tyr Glu Tyr Tyr Glu Lys Tyr Lys Ile Arg Arg Tyr
                165                 170                 175

Gly Phe His Gly Thr Ser His Arg Tyr Val Ser Lys Arg Ala Ala Glu
            180                 185                 190

Ile Leu Gly Lys Lys Leu Glu Glu Leu Lys Ile Ile Thr Cys His Ile
        195                 200                 205

Gly Asn Gly Ala Ser Val Ala Ala Val Lys Tyr Gly Lys Cys Val Asp
    210                 215                 220

Thr Ser Met Gly Phe Thr Pro Leu Glu Gly Leu Val Met Gly Thr Arg
225                 230                 235                 240

Ser Gly Asp Leu Asp Pro Ala Ile Pro Phe Phe Ile Met Glu Lys Glu
                245                 250                 255

Gly Ile Ser Pro Gln Glu Met Tyr Asp Ile Leu Asn Lys Lys Ser Gly
            260                 265                 270

Val Tyr Gly Leu Ser Lys Gly Phe Ser Ser Asp Met Arg Asp Ile Glu
        275                 280                 285

Glu Ala Ala Leu Lys Gly Asp Glu Trp Cys Lys Leu Val Leu Glu Ile
    290                 295                 300

Tyr Asp Tyr Arg Ile Ala Lys Tyr Ile Gly Ala Tyr Ala Ala Ala Met
305                 310                 315                 320

Asn Gly Val Asp Ala Ile Val Phe Thr Ala Gly Val Gly Glu Asn Ser
                325                 330                 335

Pro Ile Thr Arg Glu Asp Val Cys Ser Tyr Leu Glu Phe Leu Gly Val
            340                 345                 350

Lys Leu Asp Lys Gln Lys Asn Glu Glu Thr Ile Arg Gly Lys Glu Gly
        355                 360                 365

Ile Ile Ser Thr Pro Asp Ser Arg Val Lys Val Leu Val Val Pro Thr
    370                 375                 380

Asn Glu Glu Leu Met Ile Ala Arg Asp Thr Lys Glu Ile Val Glu Lys
385                 390                 395                 400

Ile Gly Arg Val Pro Pro Pro Cys Asp Leu Ser Ile Lys Ser Lys Leu
                405                 410                 415

Lys Gln Val Gly Ala Thr Ala Gly Asn Ala Ala Val Thr Thr Thr Gly
            420                 425                 430

Thr Thr Ser Gly Ser Gly Val Val Lys Cys Val Val Arg Thr Pro Thr
```

```
        435                 440                 445

Ser Val Glu Lys Lys Ala Ala Val Gly Asn Thr Gly Leu Ser Ala Val
    450                 455                 460

Ser Ala Ser Ala Ala Asn Gly Phe Phe Lys Asn Leu Gly Lys Ala Thr
465                 470                 475                 480

Thr Glu Val Lys Thr Thr Lys Asp Gly Thr Lys Val Lys Thr Lys Thr
                485                 490                 495

Ala Gly Lys Gly Lys Thr Gly Gly Thr Ala Thr Thr Ile Gln Ile Ala
            500                 505                 510

Asp Ala Asn Gly Gly Val Ser Glu Lys Ser Leu Lys Leu Asp Leu Leu
        515                 520                 525

Thr Asp Gly Leu Lys Phe Val Lys Val Thr Glu Lys Lys Gln Gly Thr
    530                 535                 540

Ala Thr Ser Ser Ser Gly His Lys Ala Ser Gly Val Gly His Ser Val
545                 550                 555                 560

Phe Lys Val Leu Asn Glu Ala Glu Thr Glu Leu Glu Leu Lys Gly Leu
                565                 570                 575


<210> SEQ ID NO 73
<211> LENGTH: 575
<212> TYPE: PRT
<213> ORGANISM: Artificial Sequence
<220> FEATURE:
<223> OTHER INFORMATION: Protein sequence of fusion of barnacle protein
      from Balanus albicostatus with the adenylate kinase from
      Thermotoga maritima; C-terminal fusion

<400> SEQUENCE: 73

Val Pro Pro Pro Cys Asp Leu Ser Ile Lys Ser Lys Leu Lys Gln Val
1               5                   10                  15

Gly Ala Thr Ala Gly Asn Ala Ala Val Thr Thr Thr Gly Thr Thr Ser
            20                  25                  30

Gly Ser Gly Val Val Lys Cys Val Val Arg Thr Pro Thr Ser Val Glu
        35                  40                  45

Lys Lys Ala Ala Val Gly Asn Thr Gly Leu Ser Ala Val Ser Ala Ser
    50                  55                  60

Ala Ala Asn Gly Phe Phe Lys Asn Leu Gly Lys Ala Thr Thr Glu Val
65                  70                  75                  80

Lys Thr Thr Lys Asp Gly Thr Lys Val Lys Thr Lys Thr Ala Gly Lys
                85                  90                  95

Gly Lys Thr Gly Gly Thr Ala Thr Thr Ile Gln Ile Ala Asp Ala Asn
            100                 105                 110

Gly Gly Val Ser Glu Lys Ser Leu Lys Leu Asp Leu Leu Thr Asp Gly
        115                 120                 125

Leu Lys Phe Val Lys Val Thr Glu Lys Lys Gln Gly Thr Ala Thr Ser
    130                 135                 140

Ser Ser Gly His Lys Ala Ser Gly Val Gly His Ser Val Phe Lys Val
145                 150                 155                 160

Leu Glu Ala Glu Thr Glu Leu Glu Leu Lys Gly Leu Met Arg Val Leu
                165                 170                 175

Val Ile Asn Ser Gly Ser Ser Ser Ile Lys Tyr Gln Leu Ile Glu Met
            180                 185                 190

Glu Gly Glu Lys Val Leu Cys Lys Gly Ile Ala Glu Arg Ile Gly Ile
        195                 200                 205

Glu Gly Ser Arg Leu Val His Arg Val Gly Asp Glu Lys His Val Ile
    210                 215                 220
```

Glu Arg Glu Leu Pro Asp His Glu Glu Ala Leu Lys Leu Ile Leu Asn
225 230 235 240

Thr Leu Val Asp Glu Lys Leu Gly Val Ile Lys Asp Leu Lys Glu Ile
245 250 255

Asp Ala Val Gly His Arg Val Val His Gly Gly Glu Arg Phe Lys Glu
260 265 270

Ser Val Leu Val Asp Glu Glu Val Leu Lys Ala Ile Glu Glu Val Ser
275 280 285

Pro Leu Ala Pro Leu His Asn Pro Ala Asn Leu Met Gly Ile Lys Ala
290 295 300

Ala Met Lys Leu Leu Pro Gly Val Pro Asn Val Ala Val Phe Asp Thr
305 310 315 320

Ala Phe His Gln Thr Ile Pro Gln Lys Ala Tyr Leu Tyr Ala Ile Pro
325 330 335

Tyr Glu Tyr Tyr Glu Lys Tyr Lys Ile Arg Arg Tyr Gly Phe His Gly
340 345 350

Thr Ser His Arg Tyr Val Ser Lys Arg Ala Ala Glu Ile Leu Gly Lys
355 360 365

Lys Leu Glu Glu Leu Lys Ile Ile Thr Cys His Ile Gly Asn Gly Ala
370 375 380

Ser Val Ala Ala Val Lys Tyr Gly Lys Cys Val Asp Thr Ser Met Gly
385 390 395 400

Phe Thr Pro Leu Glu Gly Leu Val Met Gly Thr Arg Ser Gly Asp Leu
405 410 415

Asp Pro Ala Ile Pro Phe Phe Ile Met Glu Lys Glu Gly Ile Ser Pro
420 425 430

Gln Glu Met Tyr Asp Ile Leu Asn Lys Lys Ser Gly Val Tyr Gly Leu
435 440 445

Ser Lys Gly Phe Ser Ser Asp Met Arg Asp Ile Glu Glu Ala Ala Leu
450 455 460

Lys Gly Asp Glu Trp Cys Lys Leu Val Leu Glu Ile Tyr Asp Tyr Arg
465 470 475 480

Ile Ala Lys Tyr Ile Gly Ala Tyr Ala Ala Ala Met Asn Gly Val Asp
485 490 495

Ala Ile Val Phe Thr Ala Gly Val Gly Glu Asn Ser Pro Ile Thr Arg
500 505 510

Glu Asp Val Cys Ser Tyr Leu Glu Phe Leu Gly Val Lys Leu Asp Lys
515 520 525

Gln Lys Asn Glu Glu Thr Ile Arg Gly Lys Glu Gly Ile Ile Ser Thr
530 535 540

Pro Asp Ser Arg Val Lys Val Leu Val Val Pro Thr Asn Glu Glu Leu
545 550 555 560

Met Ile Ala Arg Asp Thr Lys Glu Ile Val Glu Lys Ile Gly Arg
565 570 575

<210> SEQ ID NO 74
<211> LENGTH: 125
<212> TYPE: PRT
<213> ORGANISM: Balanus albicostatus

<400> SEQUENCE: 74

Met Lys Tyr Thr Leu Ala Leu Leu Phe Leu Thr Ala Ile Ile Ala Thr
1 5 10 15

Phe Val Ala Ala His Lys His His Asp His Gly Lys Ser Cys Ser Lys

-continued 20 25 30

Ser His Pro Cys Tyr His Cys His Thr Asp Cys Glu Cys Asn His His
35 40 45

His Asp Asp Cys Asn Arg Ser His Arg Cys Trp His Lys Val His Gly
50 55 60

Val Val Ser Gly Asn Cys Asn Cys Asn Leu Leu Thr Pro Cys Asn Gln
65 70 75 80

Lys His Pro Cys Trp Arg Arg His Gly Lys Lys His Gly Leu His Arg
85 90 95

Lys Phe His Gly Asn Ala Cys Asn Cys Asp Arg Leu Val Cys Asn Ala
100 105 110

Lys His Pro Cys Trp His Lys His Cys Asp Cys Phe Cys
115 120 125

<210> SEQ ID NO 75
<211> LENGTH: 24
<212> TYPE: PRT
<213> ORGANISM: Artificial Sequence
<220> FEATURE:
<223> OTHER INFORMATION: Protein sequence of a peptide derived from a barnacle cement protein

<400> SEQUENCE: 75

Ser Lys Leu Pro Cys Asn Asp Glu His Pro Cys Tyr Arg Lys Glu Gly
1 5 10 15

Gly Val Val Ser Cys Asp Cys Lys
20

<210> SEQ ID NO 76
<211> LENGTH: 24
<212> TYPE: PRT
<213> ORGANISM: Artificial Sequence
<220> FEATURE:
<223> OTHER INFORMATION: Protein sequence of a peptide derived from a barnacle cement protein

<400> SEQUENCE: 76

Ser Lys Leu Pro Ser Asn Asp Glu His Pro Ser Tyr Arg Lys Glu Gly
1 5 10 15

Gly Val Val Ser Ser Asp Ser Lys
20

<210> SEQ ID NO 77
<211> LENGTH: 28
<212> TYPE: PRT
<213> ORGANISM: Artificial Sequence
<220> FEATURE:
<223> OTHER INFORMATION: Protein sequence of a peptide derived from a barnacle cement protein

<400> SEQUENCE: 77

Lys Thr Ile Thr Cys Asn Glu Asp His Pro Cys Tyr His Ser Tyr Glu
1 5 10 15

Glu Asp Gly Val Thr Lys Ser Asp Cys Asp Cys Glu
20 25